US011053494B2

(12) United States Patent
Flanigan et al.

(10) Patent No.: US 11,053,494 B2
(45) Date of Patent: Jul. 6, 2021

(54) METHODS AND MATERIALS FOR ACTIVATING AN INTERNAL RIBOSOME ENTRY SITE IN EXON 5 OF THE DMD GENE

(71) Applicants: The Research Institute at Nationwide Children's Hospital, Columbus, OH (US); The University of Western Australia, Crawley (AU)

(72) Inventors: Kevin Flanigan, Columbus, OH (US); Nicolas Wein, Columbus, OH (US); Stephen Wilton, Perth (AU)

(73) Assignees: RESEARCH INSTITUTE AT NATIONWIDE CHILDREN'S HOSPITAL, Columbus, OH (US); THE UNIVERSITY OF WESTERN AUSTRALIA, Nedlands (AU)

( * ) Notice: Subject to any disclaimer, the term of this patent is extended or adjusted under 35 U.S.C. 154(b) by 0 days.

(21) Appl. No.: 15/502,702

(22) PCT Filed: Aug. 7, 2015

(86) PCT No.: PCT/US2015/044366
§ 371 (c)(1),
(2) Date: Feb. 8, 2017

(87) PCT Pub. No.: WO2016/025339
PCT Pub. Date: Feb. 18, 2016

(65) Prior Publication Data
US 2017/0218366 A1 Aug. 3, 2017

Related U.S. Application Data

(60) Provisional application No. 62/035,395, filed on Aug. 9, 2014.

(51) Int. Cl.
*C12N 15/113* (2010.01)
*A61K 9/00* (2006.01)
*A61K 31/573* (2006.01)
*A61K 31/58* (2006.01)
*A61K 31/712* (2006.01)

(52) U.S. Cl.
CPC .......... *C12N 15/113* (2013.01); *A61K 9/0019* (2013.01); *A61K 31/573* (2013.01); *A61K 31/58* (2013.01); *A61K 31/712* (2013.01); *C12N 2310/11* (2013.01); *C12N 2310/315* (2013.01); *C12N 2310/3231* (2013.01); *C12N 2310/3233* (2013.01); *C12N 2310/346* (2013.01); *C12N 2310/3513* (2013.01); *C12N 2310/3519* (2013.01); *C12N 2320/31* (2013.01); *C12N 2320/33* (2013.01); *C12N 2330/51* (2013.01); *C12N 2750/14143* (2013.01); *C12N 2840/203* (2013.01)

(58) Field of Classification Search
CPC ............ C12N 15/113; C12N 2840/203; C12N 2310/11
See application file for complete search history.

(56) References Cited

U.S. PATENT DOCUMENTS

| 5,173,414 | A | 12/1992 | Lebkowski et al. |
| 5,658,776 | A | 8/1997 | Flotte et al. |
| 5,786,211 | A | 7/1998 | Johnson |
| 5,871,982 | A | 2/1999 | Wilson et al. |
| 6,258,595 | B1 | 7/2001 | Gao et al. |
| 6,566,118 | B1 | 5/2003 | Atkinson et al. |
| 7,282,199 | B2 | 10/2007 | Gao et al. |
| 7,790,449 | B2 | 9/2010 | Gao et al. |
| 9,862,945 | B2 | 1/2018 | Flanigan et al. |
| 2006/0099616 | A1 | 5/2006 | Van et al. |
| 2012/0077860 | A1 | 3/2012 | Garcia |
| 2012/0270925 | A1* | 10/2012 | Wilton .................. C12N 15/111 514/44 A |
| 2013/0045538 | A1 | 2/2013 | Garcia et al. |
| 2013/0072541 | A1 | 3/2013 | Garcia |

FOREIGN PATENT DOCUMENTS

| EP | 2986632 B1 | 9/2018 |
| WO | 1995/13392 A1 | 5/1995 |
| WO | WO-1995/013365 A1 | 5/1995 |
| WO | WO-1996/017947 A1 | 6/1996 |
| WO | WO-1997/006243 A1 | 2/1997 |
| WO | WO-1997/008298 A1 | 3/1997 |
| WO | WO-1997/009441 A2 | 3/1997 |

(Continued)

OTHER PUBLICATIONS

Van Deutekom et al (Hum. Mol. Gen. 10(15): 1547-1554, 2001) (Year: 2001).*
Aartsma-Rus et al (Neuromuscular Disorders 12: S71-S77, 2002) (Year: 2002).*
Mann et al (J. Gene Med. 4(6):644-54, 2002) (Year: 2002).*
Aartsma-Rus et al (Mol. Ther. 17(3): 548-553, 2009) (Year: 2009).*
Wu et al (PLoS One 6(5): 12 pages, 2011) (Year: 2011).*
Arechavala-Gomeza et al (Hum. Gene Ther. Sep. 2007; 18(9):798-810) (Year: 2007).*
Wein et al., (Supplementary Information for Wein et al., (Nature Medicine 20(9) :992-100, 2014), 10 pages) (Year: 2014).*

(Continued)

*Primary Examiner* — Richard A Schnizer
(74) *Attorney, Agent, or Firm* — Marshall, Gerstein & Borun LLP

(57) ABSTRACT

The present invention relates to the delivery of oligomers for treating patients with a 5' mutation in their DMD gene other than a DMD exon 2 duplication. The invention provides methods and materials for activating an internal ribosome entry site in exon 5 of the DMD gene resulting in translation of a functional truncated isoform of dystrophin. The methods and materials can be used for the treatment of muscular dystrophies arising from 5' mutations in the DMD gene such as Duchenne Muscular Dystrophy or Becker Muscular Dystrophy.

27 Claims, 51 Drawing Sheets

Specification includes a Sequence Listing.

(56) References Cited

FOREIGN PATENT DOCUMENTS

| WO | WO-1997/021825 A1 | 6/1997 |
|---|---|---|
| WO | WO-1998/009657 A2 | 3/1998 |
| WO | WO-1999/011764 A2 | 3/1999 |
| WO | 2001/83692 A2 | 11/2001 |
| WO | 2003/74654 A2 | 9/2003 |
| WO | 2004/083432 A1 | 9/2004 |
| WO | 2010/108126 A2 | 9/2010 |
| WO | WO-2011057350 A1 | 5/2011 |
| WO | 2011/113889 A1 | 9/2011 |
| WO | WO-2011078797 A3 | 11/2011 |
| WO | 2014/172669 A1 | 10/2014 |

OTHER PUBLICATIONS

Vulin et al., "A New Mouse Model of DMD: A Tool for Therapeutic Development at Exon Duplications," Molecular Therapy, 16th Annual Meeting of the American Society of Gene and Cell Therapy, Salt Lake City, UT, USA; Academic Press, US, vol. 21, Suppl. 1, p. S71 (2013).
Ameur et al., Total RNA sequencing reveals nascent transcription and widespread co-transcriptional splicing in the human brain, Nat. Struct. Mol. Biol., 18(12):1435-40 (2011).
Beggs et al., Exploring the molecular basis for variability among patients with Becker muscular dystrophy: dystrophin gene and protein studies, Am. J. Hum. Genet., 49(1):54-67 (1991).
Betts et al., Prevention of exercised induced cardiomyopathy following Pip-PMO treatment in dystrophic mdx mice, Sci. Rep., 5:8986 (2015).
Biggar et al., Deflazacort treatment of Duchenne muscular dystrophy, J. Pediatr., 138(1):45-50 (2001).
Chaouch et al., Immortalized skin fibroblasts expressing conditional MyoD as a renewable and reliable source of converted human muscle cells to assess therapeutic strategies for muscular dystrophies: validation of an exon-skipping approach to restore dystrophin in Duchenne muscular dystrophy cells, Hum. Gene Ther., 20(7):784-90 (2009).
Cirak et al., Exon skipping and dystrophin restoration in patients with Duchenne muscular dystrophy after systemic phosphorodiamidate morpholino oligomer treatment: an open-label, phase 2, dose-escalation study, Lancet, 378(9791):595-605 (2011).
Clark et al., Highly purified recombinant adeno-associated virus vectors are biologically active and free of detectable helper and wild-type viruses, Hum. Gene Ther., 10(6)1031-9 (1999).
De et al., High levels of persistent expression of alpha1-antitrypsin mediated by the nonhuman primate serotype rh.10 adeno-associated virus despite preexisting immunity to common human adeno-associated viruses, Mol. Ther., 13(1):67-76 (2006).
Dent et al., Improved molecular diagnosis of dystrophinopathies in an unselected clinical cohort, Am. J. Med. Genet. A, 134(3):295-8 (2005).
Flanigan et al., Becker muscular dystrophy with widespread muscle hypertrophy and a non-sense mutation of exon 2, Neuromuscul. Disord., 23(2):192 (2013).
Flanigan et al., DMD Trp3X nonsense mutation associated with a founder effect in North American families with mild Becker muscular dystrophy, Neuromuscul. Disord., 19(11):743-8 (2009).
Flanigan et al., Mutational spectrum of DMD mutations in dystrophinopathy patients: application of modern diagnostic techniques to a large cohort, Hum. Mutat., 30(12):1657-66 (2009).
Gao et al., Clades of Adeno-associated viruses are widely disseminated in human tissues, J. Virol., 78(12):6381-8 (2004).
Gimona et al., Functional plasticity of CH domains, FEBS Lett., 513(1):98-106 (2002).
Goemans et al., Systemic administration of PRO051 in Duchenne's muscular dystrophy, N. Engl. J. Med., 364(16):1513-22 (2011).
Goyenvalle et al., Engineering multiple U7snRNA constructs to induce single and multiexon-skipping for Duchenne muscular dystrophy, Mol. Ther., 20(6):1212-21 (2012).
Goyenvalle et al., Functional correction in mouse models of muscular dystrophy using exon-skipping tricyclo-DNA oligomers, Nat. Med., 21(3):270-5 (2015).
Goyenvalle et al., Rescue of dystrophic muscle through U7 snRNA-mediated exon skipping, Science, 306(5702):1796-9 (2004).
Greer et al., Targeted exon skipping to correct exon duplications in the dystrophin gene, Mol. Ther. Nucleic Acids, 3:e155 (2014).
Gurvich et al., DMD exon 1 truncating point mutations: amelioration of phenotype by alternative translation initiation in exon 6, Hum. Mutat., 30(4):633-40 (2009).
Heald et al., Becker muscular dystrophy with onset after 60 years, Neurology, 44912):2388-90 (1994).
Hermonat et al., Use of adeno-associated virus as a mammalian DNA cloning vector: transduction of neomycin resistance into mammalian tissue culture cells, Proc. Natl. Acad. Sci. USA, 81(20):6466-70 (1984).
International Search Report and Written Opinion, International Application No. PCT/US15/44366, dated Feb. 1, 2016.
Kinali et al., Local restoration of dystrophin expression with the morpholino oligomer AVI-4658 in Duchenne muscular dystrophy: a single-blind, placebo-controlled, dose-escalation, proof-of-concept study, Lancet Neurol., 8(10):918-28 (2009).
Laughlin et al., Cloning of infectious adeno-associated virus genomes in bacterial plasmids, Gene, 23(1):65-73 (1983).
Mader et al., A steroid-inducible promoter for the controlled overexpression of cloned genes in eukaryotic cells, Proc. Natl. Acad. Sci. USA, 90(12):5603-7 (1993).
McLaughlin et al., Adeno-associated virus general transduction vectors: analysis of proviral structures, J. Virol., 62(6):1963-7 (1988).
Mendell et al., Eteplirsen for the treatment of Duchenne muscular dystrophy, Ann. Neurol., 74(5):637-47 (2013).
Mendell et al., Randomized, double-blind six-month trial of prednisone in Duchenne's muscular dystrophy, N. Engl. J. Med., 320(24):1592-7 (1989).
Miura et al., IRES-mediated translation of utrophin A is enhanced by glucocorticoid treatment in skeletal muscle cells, PLoS One, 3(6):e2309 (2008).
Miura et al., The utrophin a 5'-untranslated region confers internal ribosome entry site-mediated translational control during regeneration of skeletal muscle fibers, J. Biol. Chem., 280(38):32997-3005 (2005).
Monaco et al., Dystrophin, the protein product of the Duchenne/Becker muscular dystrophy gene, Trends Biochem. Sci., 14910):412-5 (1989).
Mori et al., Two novel adeno-associated viruses from cynomolgus monkey: pseudotyping characterization of capsid protein, Virology, 330(2):375-83 (2004).
Muzyczka, Use of adeno-associated virus as a general transduction vector for mammalian cells, Curr. Top Microbiol. Immunol., 158:97-129 (1992).
Paul et al., Increased viral titer through concentration of viral harvests from retroviral packaging lines, Hum. Gene Ther., 4(5):609-15 (1993).
Perrin et al., An experimental rabies vaccine produced with a new BHK-21 suspension cell culture process: use of serum-free medium and perfusion-reactor system, Vaccine, 13(13):1244-50 (1995).
Samulski et al., Cloning of adeno-associated virus into pBR322: rescue of intact virus from the recombinant plasmid in human cells, Proc. Natl. Acad. Sci. USA, 79(6):2077-81 (1982).
Samulski et al., Helper-free stocks of recombinant adeno-associated viruses: normal integration does not require viral gene expression, J. Virol., 63(9):3822-8 (1989).
Schnepp et al., Highly purified recombinant adeno-associated virus vectors. Preparation and quantitation, Methods Mol. Med., 69:427-43 (2002).
Semenza et al., Hypoxia-inducible nuclear factors bind to an enhancer element located 3' to the human erythropoietin gene, Proc. Natl. Acad. Sci. USA, 88(13):5680-4 (1991).
Senapathy et al., Molecular cloning of adeno-associated virus variant genomes and generation of infectious virus by recombination in mammalian cells, J. Biol. Chem., 259(7):4661-6 (1984).

(56) References Cited

OTHER PUBLICATIONS

Srivastava et al., Nucleotide sequence and organization of the adeno-associated virus 2 genome, J. Virol., 45(2):555-64 (1983).
Tennyson et al., Stability of the human dystrophin transcript in muscle, Nucleic Acids Res., 24(15):3059-64 (1996).
Tratschin et al., A human parvovirus, adeno-associated virus, as a eucaryotic vector: transient expression and encapsidation of the procaryotic gene for chloramphenicol acetyltransferase, Mol. Cell Biol., 4(10):2072-81 (1984).
Van Deutekom et al., Local dystrophin restoration with antisense oligonucleotide PRO051, N. Engl. J. Med., 357(26):2677-86 (2007).
Vulin et al., Muscle function recovery in golden retriever muscular dystrophy after AAV1-U7 exon skipping, Mol. Ther., 20(11):2120-33 (2012).
Wein et al., Successful use of out-of-frame exon 2 skipping induces IRES-driven expression of the N-truncated dystrophin isoform: promising approach for treating other 5' dystrophin mutations, Mol. Ther., 22(Suppl. 1):S294-S295 (2014).
Wein et al., Translation from a DMD exon 5 IRES results in a functional dystrophin isoform that attenuates dystrophinopathy in humans and mice, Nat. Med., 20(9):992-1000 (2014).
White et al., Duplications in the DMD gene, Hum. Mutat., 27(9):938-45 (2006).
Winnard et al., Characterization of translational frame exception patients in Duchenne/Becker muscular dystrophy, Hum. Mol. Genet., 2(6):737-44 (1993).
Winnard et al., Frameshift deletions of exons 3-7 and revertant fibers in Duchenne muscular dystrophy: mechanisms of dystrophin production, Am. J. Hum. Genet., 5691):158-66 (1995).
Witting et al., Becker muscular dystrophy with widespread muscle hypertrophy and a non-sense mutation of exon 2, Neuromuscul. Disord., 23(1):25-8 (2013).
Wood et al., RNA-targeted splice-correction therapy for neuromuscular disease, Brain, 133(Pt. 4):957-72 (2010).
Aartsma-Rus et al: Antisense-induced exon skipping for duplications in Duchenne muscular dystrophy, BMC Medical Genetics, 8(1):43 (2007).
Carter, Adeno-associated virus vectors, Curr. Opin. Biotechnol., 3(5):533-9 (1992).
Clark et al., A stable cell line carrying adenovirus-inducible rep and cap genes allows for infectivity titration of adeno-associated virus vectors, Gene Therapy, 3:1124-32 (1996).
Cserjesi et al., Myogenin induces the myocyte-specific enhancer binding factor MEF-2 independently of other muscle-specific gene products, Mol. Cell. Biol., 11:4854-62 (1991).
Exon Skipping Strategies for the Treatment of Duplication Mutations in Duchenne Muscular Dystrophy,<http://support.cureduchenne.org/site/P>Cure Duchenne (2012).
Galland et al., Multi-confocal fluorescence correlation spectroscopy, Am. J. Physiol. Cell. Physiol., 296:476-88 (2009).
GenBank Accession No. AF085716, Adena-associated virus 5 DNA binding trs helicase (Rep22) and capsid protein (VP1) genes, complete cds, dated Feb. 9, 1999.
GenBank Accession No. NC_001401, Adena-associated virus-2, complete genome, dated Dec. 2, 2014.
GenBank Accession No. NC_001829, Adena-associated virus-4, complete genome, dated Jan. 28, 2010.
Genbank Accession No. NC_001862, Adena-associated virus 6, complete genome, dated Jan. 12, 2004.
GenBank Accession No. NC_002077, Adena-associated virus-1, complete genome, dated Mar. 11, 2010.
GenBank Accession Nos. AX753246, Sequence 1 from Patent EP1310571, dated Jun. 23, 2003.
GenBank Accession Nos. AX753249, Sequence 4 from Patent EP1310571, dated Jun. 23, 2003.
Goyenvalle et al., Engineering Exon-Skipping Vectors Expressing U7 snRNA Constructs for Duchenne Muscular Dystrophy Gene Therapy, Mus. Gene Ther., 306(5702):179-96 (2011).
Goyenvalle et al., Rescue of severely affected dystrophin/utrophin-deficient mice through scAAV-U7snRNA-mediated exon skipping, Hum. Molec. Gen., 21(11):2559-71 (2012).
Goyenvalle et al., Therapeutic approaches to muscular dystrophy, Hum. Molec. Gen., 20(R1):R69-78 (2011).
Greer et al., Targeted Exon Skipping to Correct Duplicated Exons in the Dystrophin Gene, 8th Australasian Gene Therapy Society Meeting, J. Gene Med., 15:311-40 (2013).
Hakim et al., The passive mechanical properties of the extensor digitorum longus muscle are compromised in 2- to 20-mo-old mdx mice, J. Appl. Physiol., 110:1656-63 (1985).
International Preliminary Report on Patentability received for PCT Patent Application No. PCT/US2014/034702, dated Oct. 29, 2015, 7 pages.
International Preliminary Report on Patentability received for PCT Patent Application No. PCT/US2015/044366, dated Feb. 23, 2017, 10 pages.
International Search Report and Written Opinion received for PCT Patent Application No. PCT/US2014/034702, dated Sep. 1, 2014, 10 pages.
International Search Report and Written Opinion received for PCT Patent Application No. PCT/US2015/044366, dated Feb. 1, 2016, 13 pages.
Janssen et al., Utrophin deficiency worsens cardiac contractile dysfunction present in dystrophin-deficient mdx mice, Am. J. Physiol. Heart Circ. Physiol., 289(6):H2373-8 (2005).
Johnson et al., Muscle creatine kinase sequence elements regulating skeletal and cardiac muscle expression in transgenic mice, Mol. Cell. Biol., 9:3393-9 (1989).
Lebkowski et al., Adeno-associated virus: a vector system for efficient introduction and integration of DNA into a variety of mammalian cell types, Mol. Cell. Biol., 7:3988-96-(1988).
Muscat et al., Multiple 5'-flanking regions of the human alpha-skeletal actin gene synergistically modulate muscle-specific expression, Mol. Cell. Biol., 7:4089-99 (1987).
Rabinowitz et al., Cross-packaging of a single adeno-associated virus (AAV) type 2 vector genome into multiple AAV serotypes enables transduction with broad specificity, J. Virol., 76:791-801 (2002).
Rodino-Klapac et al., Persistent expression of FLAG-tagged micro dystrophin in nonhuman primates following intramuscular and vascular delivery, Mol. Ther., 18(1):109-17 (2010).
Spurney et al, Preclinical drug trials in the mdx mouse: assessment of reliable and sensitive outcome measures, Muscle & Nerve, 39:591-602 (2009).
Tratschin et al., Adeno-associated virus vector for high-frequency integration, expression, and rescue of genes in mammalian cells, Mol. Cell. Biol., 5:3251 (1985).
Wang et al., Recombinant AAV serotype 1 transduction efficiency and tropism in the murine brain, Gene. Ther., 10:1528-34 (2003).
Weintraub et al., The myoD gene family: nodal point during specification of the muscle cell lineage, Science, 251:761-6 (1991).
Xu et al., Postnatal overexpression of the CT GalNAc transferase inhibits muscular dystrophy in mdx mice without altering muscle growth or neuromuscular development: evidence for a utrophin-independent mechanism, Neuromusc. Dis., 17:209-20 (2007).
Internet material, Cure Duchenne Supports Duchenne Duplication Mutation Research with Dr. Kevin Flanigan, 1-4 (2012).

* cited by examiner

```
                             Exon1              Exon2
Dystrophin ref seq  MLWWEEVEDCYEREDVQKKTFTKWVNAQFSKFGKQHIENLFSDLQDGRRLLDLLEGLTGQ   60
DEL2 subject        ----------------------------WVNAQFSKFGKQHIENLFSDLQDGRRLLDLLEGLTGQ   37
Control Exon4                        Exon5
Dystrophin ref seq  KLPKEKGSTRVHALNVNKALRVLQNNNVDLVNIGSTDIVDGNHKLTLGLIWNIILHWQV   120
DEL2 subject        -------------------------VLQNNNVDLVNIGSTDIVDGNH------------
Control             K Exon6
Dystrophin ref seq  KNIMKNIMAGLQQTNSEKILLSWVRQSTRNYPQVNVINFTTSWSDGLALNALIHSRPDL   180
DEL2 subject        ------KNIMAGLQQTNSEKILL-------------------------------------
Control Exon7                        Exon8
Dystrophin ref seq  FDWNSVVCQQSATQRLEHAFNIARYQLGIEKLLDPEDVDTTYPDKKSILMYITSLFQVLP   240
DEL2 subject        ----------------------YQLGIEKLLDPEDVDTTYPDKK---------------
Control             --------LEHAFNIARYQLGIEKLLDPEDVDTTYPDKK---------------
```

FIGURE 1B

DYS3

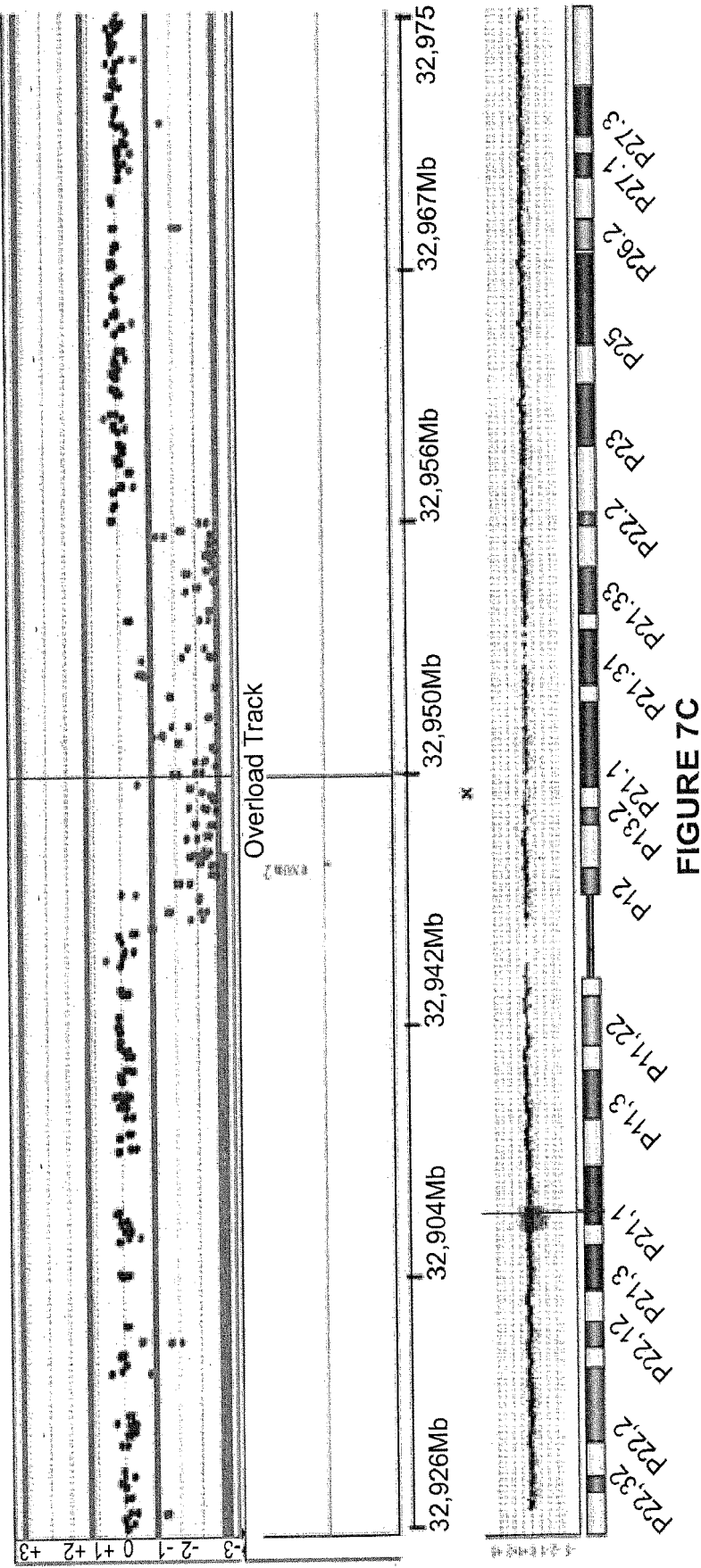

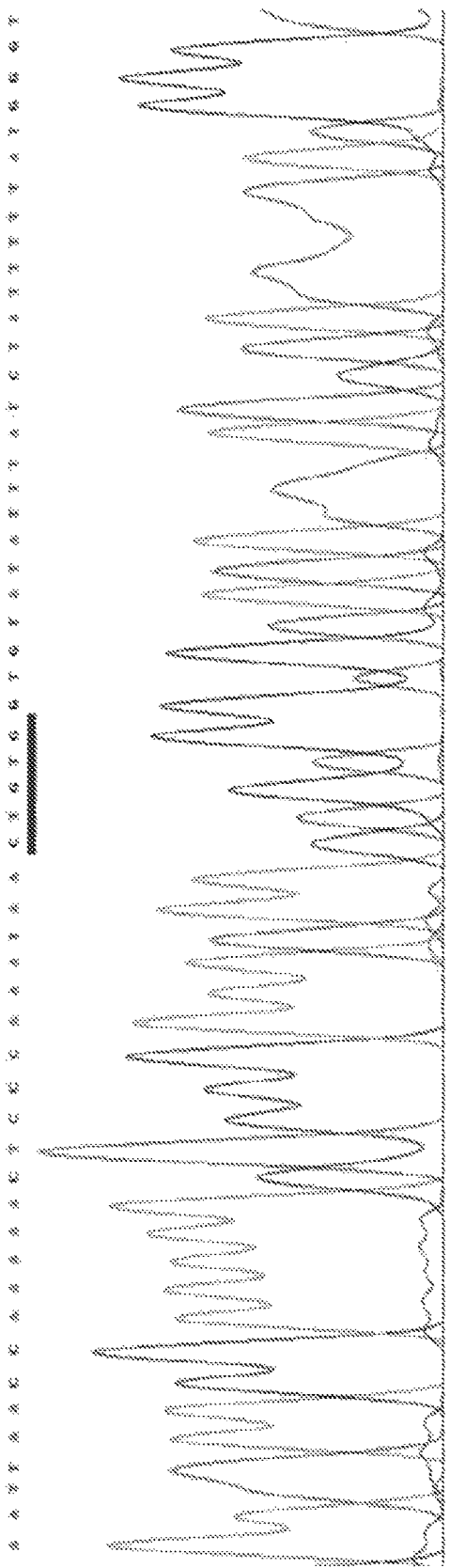
FIGURE 7E
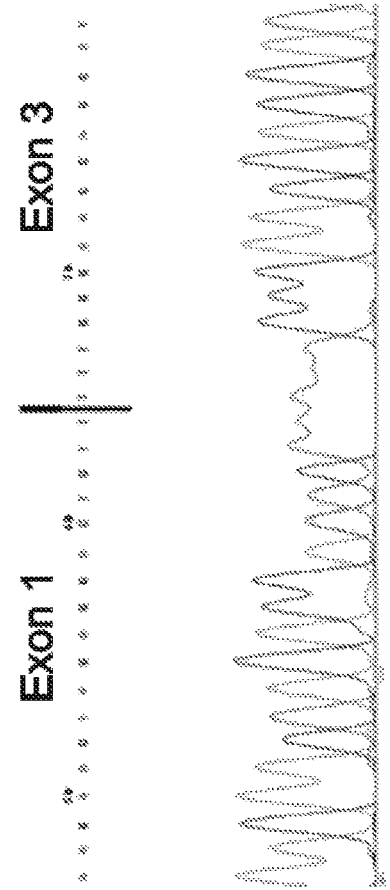
FIGURE 7F
FIGURE 7G

Figure 13

```
5'  CTCCATCACTAGGGGTAACCGCGAAGCGCCTCCCACGCTGCCGCGTCAGC
    +--+--+--+--+--+--+--+--+--+--+--+--+--+--+--+--+--+--+--+--+  50
        •————D————•

5'  GCTGACGTAAATTACGTCATAGGGGAGTGGTCCTGTATTAGCTGTCACGT
    +--+--+--+--+--+--+--+--+--+--+--+--+--+--+--+--+--+--+--+--+  100

5'  GAGTGCTTTTGCGACATTTTGCGACACCACGTGGCCATTCATGGTATATA
    +--+--+--+--+--+--+--+--+--+--+--+--+--+--+--+--+--+--+--+--+  150
                                                  TAT..box 5'  TGGCCGAGTGAGCGAGCAGGATCTCCATTTTGACCGCGAAATTTGAACGA
    +--+--+--+--+--+--+--+--+--+--+--+--+--+--+--+--+--+--+--+--+  200
    ▪                        p...oter 5'  GCAGCAGCCATGCCGGGCTTCTACGAGATCGTGCTTAAGGTGCCGAGCGA
    +--+--+--+--+--+--+--+--+--+--+--+--+--+--+--+--+--+--+--+--+  250
        |_____Rep_____|

5'  CCTGGACGAGCACCTGCCGGGCATTTCTGACTCGTTTGTGAACTGGGTGG
    +--+--+--+--+--+--+--+--+--+--+--+--+--+--+--+--+--+--+--+--+  300
    _____Rep_____

5'  CAGAGAAGGAATGGGAGCTGCCCCCGGATTCTGACATGGATCGGAATCTG
    +--+--+--+--+--+--+--+--+--+--+--+--+--+--+--+--+--+--+--+--+  350
    _____Rep_____

5'  ATTGAGCAGGCACCCCTGACCGTGGCCGAGAAGCTACAGCGCGACTTCCT
    +--+--+--+--+--+--+--+--+--+--+--+--+--+--+--+--+--+--+--+--+  400
    _____Rep_____

5'  GGTCCAATGGCGCCGCGTGAGTAAGGCCCCGGAGGCCCTCTTCTTTGTTC
    +--+--+--+--+--+--+--+--+--+--+--+--+--+--+--+--+--+--+--+--+  450
    _____Rep_____

5'  AGTTCGAGAAGGGCGAGTCCTACTTCCACCTCCATATTCTGGTAGAGACC
    +--+--+--+--+--+--+--+--+--+--+--+--+--+--+--+--+--+--+--+--+  500
    _____Rep_____
```

Figure 13 Continued

```
5'  ACGGGGGTCAAATCCATGGTGCTGGGCCGCTTCCTGAGTCAGATTCGGGA
                                                              550
            Rep

5'  CAAGCTGGTGCAGACCATCTACCGCGGGATCGAGCCGACCCTGCCCAACT
                                                              600
            Rep

5'  GGTTCGCGGTGACAAAGACGCGTAATGGCGCCGGAGGGGGGAACAAGGTG
                                                              650
            Rep

5'  GTGGACGAGTGCTACATCCCCAACTACCTGCTGCCCAAGACTCAGCCCGA
                                                              700
            Rep

5'  GCTGCAGTGGGCGTGGACTAACATGGAGGAGTATATAAGCGCGTGCTTGA
                                                              750
            Rep
                                    TATA Box

5'  ACCTGGCCGAGCGCAAACGGCTCGTGGCGCAGCACCTGACCCACGTCAGC
                                                              800
            Rep
        p1...1

5'  CAGACCCAGGAGCAGAACAAGGAGAATCTGAACCCGAATTCTGACGCGCC
                                                              850
            Rep

5'  TGTCATCCGGTCAAAAACCTCCGCGCGCTACATGGAGCTGGTCGGGTGGC
                                                              900
            Rep
                                        Rep 52 ORF
```

Figure 13 Continued

```
5'  TGGTGGACCGGGGCATCACCTCCGAGAAGCAGTGGATCCAGGAGGACCAG
                                                      950
            Rep
            Rep 52 ORF

5'  GCCTCGTACATCTCCTTCAACGCCGCCTCCAACTCGCGGTCTCAGATCAA
                                                      1000
            Rep
            Rep 52 ORF

5'  GGCCGCGCTGGACAATGCCGGCAAGATCATGGCGCTGACCAAATCCGCGC
                                                      1050
            Rep
            Rep 52 ORF

5'  CCGACTACCTGGTAGGCCCCGCTCTGCCCGCGGACATTAAATCCAACCGC
                                                      1100
            Rep
            Rep 52 ORF

5'  ATCTACCGCATCCTGGAGCTGAATGGCTACGACCCTGCCTACGCCGGTTC
                                                      1150
            Rep
            Rep 52 ORF

5'  CGTCTTTCTCGGCTGGGCCCAGAAAAAGTTTGGCAAAAGGAACACCATCT
                                                      1200
            Rep
            Rep 52 ORF

5'  GGCTGTTTGGGCCGGCCACCACGGGCAAGACCAACATCGCGGAAGCCATC
                                                      1250
            Rep
            Rep 52 ORF
```

Figure 13 Continued

```
5'  GCCCACGCCGTGCCCTTCTACGGCTGCGTCAACTGGACCAATGAGAACTT
                                                        1300
                        Rep
                      Rep 52 ORF

5'  TCCCTTCAACGATTGCGTCGACAAGATGGTGATCTGGTGGGAGGAGGGCA
                                                        1350
                        Rep
                      Rep 52 ORF

5'  AGATGACGGCCAAGGTCGTGGAGTCCGCCAAGGCCATTCTCGGCGGCAGC
                                                        1400
                        Rep
                      Rep 52 ORF

5'  AAGGTGCGCGTGGACCAAAAGTGCAAGTCGTCCGCCCAGATCGATCCCAC
                                                        1450
                        Rep
                      Rep 52 ORF

5'  CCCCGTGATCGTCACCTCCAACACCAACATGTGCGCCGTGATTGACGGGA
                                                        1500
                        Rep
                      Rep 52 ORF

5'  ACAGCACCACCTTCGAGCACCAGCAGCCGTTGCAGGACCGGATGTTCAAA
                                                        1550
                        Rep
                      Rep 52 ORF

5'  TTTGAACTTACCCGCCGTCTGGAGCACGACTTTGGCAAGGTGACAAAGCA
                                                        1600
                        Rep
                      Rep 52 ORF
```

Figure 13 Continued

```
5'  GGAAGTCAAAGAGTTCTTCCGCTGGGCGCAGGATCACGTGACCGAGGTGG
                                                          1650
                        Rep
                     Rep 52 ORF

5'  CGCATGAGTTCTACGTCAGAAAGGGTGGAGCTAACAAAAGACCCGCCCCC
                                                          1700
                        Rep
                     Rep 52 ORF

5'  GATGACGCGGATATAAGCGAGCCCAAGCGGGCCTGCCCCTCAGTCGCGGA
                                                          1750
                        Rep
                     Rep 52 ORF
           p40...ox

5'  TCCATCGACGTCAGACGCGGAAGGAGCTCCGGTGGACTTTGCCGACAGGT
                                                          1800
                        Rep
                     Rep 52 ORF
                                                   Sp...r

5'  ACCAAAACAAATGTTCTCGTCACGCGGGCATGCTTCAGATGCTGTTTCCC
                                                          1850
                        Rep
                     Rep 52 ORF

5'  TGCAAAACATGCGAGAGAATGAATCAGAATTTCAACATTTGCTTCACGCA
                                                          1900
                        Rep
                     Rep 52 ORF

5'  CGGGACCAGAGACTGTTCAGAATGTTTCCCTGGCGTGTCAGAATCTCAAC
                                                          1950
                        Rep
                     Rep 52 ORF
```

Figure 13 Continued

```
5'  CGGTCGTCAGAAAAAAGACGTATCGGAAACTCTGTGCGATTCATCATCTG
                                                            2000
                         Rep
                       Rep 52 ORF

5'  CTGGGGCGGGCACCCGAGATTGCTTGCTCGGCCTGCGACCTGGTCAACGT
                                                            2050
                         Rep
                       Rep 52 ORF

5'  GGACCTGGATGACTGTGTTTCTGAGCAATAAATGACTTAAACCAGGTATG
                                                            2100
                         Rep
                                                    Cap
               Rep 52 ORF
                              R...
                                          sp...r

5'  GCTGCCGATGGTTATCTTCCAGATTGGCTCGAGGACAACCTCTCTGAGGG
                                                            2150
                         Rep
                         Cap
                    sp...r
                                          R...

5'  CATTCGCGAGTGGTGGGACCTGAAACCTGGAGCCCCGAAACCCAAAGCCA
                                                            2200
                         Cap

5'  ACCAGCAAAAGCAGGACAACGGCCGGGGTCTGGTGCTTCCTGGCTACAAG
                                                            2250
                         Cap

5'  TACCTCGGACCCTTCAACGGACTCGACAAGGGGGAGCCCGTCAACGCGGC
                                                            2300
                         Cap
```

Figure 13 Continued

```
5'  GGACGCAGCGGCCCTCGAGCACGACAAGGCCTACGACCAGCAGCTCCAAG
                                                              2350
                          Cap

5'  CGGGTGACAATCCGTACCTGCGGTATAATCACGCCGACGCCGAGTTTCAG
                                                              2400
                          Cap

5'  GAGCGTCTGCAAGAAGATACGTCTTTTGGGGGCAACCTCGGGCGCGCAGT
                                                              2450
                          Cap

5'  CTTCCAGGCCAAAAAGCGGGTTCTCGAACCTCTGGGCCTGGTTGAATCGC
                                                              2500
                          Cap

5'  CGGTTAAGACGGCTCCTGGAAAGAAGAGACCGGTAGAGCCATCACCCCAG
                                                              2550
                          Cap
      V..1

5'  CGCTCTCCAGACTCCTCTACGGGCATCGGCAAGAAAGGCCAGCAGCCCGC
                                                              2600
                          Cap

5'  AAAAAAGAGACTCAATTTTGGGCAGACTGGCGACTCAGAGTCAGTCCCCG
                                                              2650
                          Cap

5'  ACCCTCAACCAATCGGAGAACCACCAGCAGGCCCCTCTGGTCTGGGATCT
                                                              2700
                          Cap

5'  GGTACAATGGCTGCAGGCGGTGGCGCTCCAATGGCAGACAATAACGAAGG
                                                              2750
                          Cap
      VP3
```

Figure 13 Continued

```
5'  CGCCGACGGAGTGGGTAGTTCCTCAGGAAATTGGCATTGCGATTCCACAT
                                                          2800
                          Cap

5'  GGCTGGGCGACAGAGTCATCACCACCAGCACCCGCACCTGGGCCCTGCCC
                                                          2850
                          Cap

5'  ACCTACAACAACCACCTCTACAAGCAAATCTCCAACGGGACCTCGGGAGG
                                                          2900
                          Cap

5'  AAGCACCAACGACAACACCTACTTCGGCTACAGCACCCCTGGGGGTATT
                                                          2950
                          Cap

5'  TTGACTTCAACAGATTCCACTGCCACTTTTCACCACGTGACTGGCAGCGA
                                                          3000
                          Cap

5'  CTCATCAACAACAACTGGGGATTCCGGCCCAAGAGGCTCAACTTCAAGCT
                                                          3050
                          Cap

5'  CTTCAACATCCAAGTCAAGGAGGTCACGCAGAATGAAGGCACCAAGACCA
                                                          3100
                          Cap

5'  TCGCCAATAACCTTACCAGCACGATTCAGGTCTTTACGGACTCGGAATAC
                                                          3150
                          Cap

5'  CAGCTCCCGTACGTGCTCGGCTCGGCGCACCAGGGCTGCCTGCCTCCGTT
                                                          3200
                          Cap
```

Figure 13 Continued

```
5'  CCCGGCGGACGTCTTCATGATTCCTCAGTACGGGTACCTGACTCTGAACA
                                                          3250
                          Cap

5'  ATGGCAGTCAGGCTGTGGCCGGTCGTCCTTCTACTGCCTGGAGTACTTT
                                                          3300
                          Cap

5'  CCTTCTCAAATGCTGAGAACGGGCAACAACTTTGAATTCAGCTACAACTT
                                                          3350
                          Cap

5'  CGAGGACGTGCCCTTCCACAGCAGCTACGCGCACAGCCAGAGCCTGGACC
                                                          3400
                          Cap

5'  GGCTGATGAACCCTCTCATCGACCAGTACTTGTACTACCTGTCCCGGACT
                                                          3450
                          Cap

5'  CAAAGCACGGGCGGTACTGCAGGAACTCAGCAGTTGCTATTTTCTCAGGC
                                                          3500
                          Cap

5'  CGGGCCTAACAACATGTCGGCTCAGGCCAAGAACTGGCTACCCGGTCCCT
                                                          3550
                          Cap

5'  GCTACCGGCAGCAACGCGTCTCCACGACACTGTCGCAGAACAACAACAGC
                                                          3600
                          Cap

5'  AACTTTGCCTGGACGGGTGCCACCAAGTATCATCTGAATGGCAGAGACTC
                                                          3650
                          Cap
```

Figure 13 Continued

```
5'  TCTGGTGAATCCTGGCGTTGCCATGGCTACCCACAAGGACGACGAAGAGC
                                                        3700
                         Cap

5'  GATTTTTTTCCATCCAGCGGAGTCTTAATGTTTGGGAAACAGGGAGCTGGA
                                                        3750
                         Cap

5'  AAAGACAACGTGGACTATAGCAGCGTGATGCTAACCAGCGAGGAAGAAAT
                                                        3800
                         Cap

5'  AAAGACCACCAACCCAGTGGCCACAGAACAGTACGGCGTGGTGGCCGATA
                                                        3850
                         Cap

5'  ACCTGCAACAGCAAAACGCCGCTCCTATTGTAGGGGCCGTCAATAGTCAA
                                                        3900
                         Cap

5'  GGAGCCTTACCTGGCATGGTGTGGCAGAACCGGGACGTGTACCTGCAGGG
                                                        3950
                         Cap

5'  TCCCATCTGGGCCAAGATTCCTCATACGGACGGCAACTTTCATCCCTCGC
                                                        4000
                         Cap

5'  CGCTGATGGGAGGCTTTGGACTGAAGCATCCGCCTCCTCAGATCCTGATT
                                                        4050
                         Cap

5'  AAAAACACACCTGTTCCCGCGGATCCTCCGACCACCTTCAATCAGGCCAA
                                                        4100
                         Cap
```

Figure 13 Continued

```
5'  GCTGGCTTCTTTCATCACGCAGTACAGTACCGGCCAGGTCAGCGTGGAGA
                                                              4150
                          Cap

5'  TCGAGTGGGAGCTGCAGAAGGAGAACAGCAAACGCTGGAACCCAGAGATT
                                                              4200
                          Cap

5'  CAGTACACTTCCAACTACTACAAATCTACAAATGTGGACTTTGCTGTCAA
                                                              4250
                          Cap

5'  TACTGAGGGTACTTATTCCGAGCCTCGCCCCATTGGCACCCGTTACCTCA
                                                              4300
                          Cap

5'  CCCGTAATCTGTAATTACATGTTAATCAATAAACCGGTTAATTCGTTTCA
                                                              4350
         Cap
           c...        poly...nal 5'  GTTGAACTTTGGTCTCCTGTCCTTCTTATCTTATCGGTTACCATAGAAAC
                                                              4400

5'  TGGTTACTTATTAACTGCTTGGTGCGCTTCGCGATAAAAGACTTACGTCA
                                                              4450

5'  TCGGGTTACCCCTAGTGATGGA
                                                              4472
              D
```

Legend:

ATCG: inverted terminal sequence (ITR)

ATCG U7-Along (antisense sequence in capital letters (first copy)

ATCG U7-C (antisense sequence in capital letters)(first copy)

ATCG U7-C (antisense sequence in capital letters) (second copy)

ATCG U7-Along (antisense sequence in capital letters) (second copy)

ATCG: inverted terminal sequence 3' (ITR)

3'–
ctgcgcgctcgctcgctcactgaggccgcccgggcaaagcccggtcgggcgacctttggtcgcccggcctcagtgagcgagcgag
cgcgcagagagggagtggggttgtacacatacgcgttcctaggaaaccagagaaggatcaaagcccctctcacacaccggggagcgg
ggaagagaactgttttgctttcattgtagaccagtgaaattgggagggttttccgaccgaagtcagaaaacctgCTCCAAAAATTt
agATGAAAGAGAAGATCTTCAAAAGAAAACttgcggaagtgcgtctgtagcgagccagggAaggacatcaa
ctccactttcgatgagggtgagatcaaggtgccatttccacacccctccactgatatgtgaatcacaaagcacagttccttattcggttcgataa
acaatattctaaaagactattaaaaccgctcgtttcttgagtttgtgaccgcttgtaaaggctatgcaaatgagTcagtgctgattggctgaaaa
cagccaatcacagctcctatgttgttaTCTAGCcacatacgcgtttcctaggaaaccagagaaggatcaaagcccctctcacacaccg
gggagcggggaagagaactgttttgctttcattgtagaccagtgaaattgggagggttttccgaccgaagtcagaaaacctgCTCCA
AAAATTGCACAATTTTCTAAGGTAAGAATTTgcggaagtgcgtctgtagcgagccagggAaggacatcaa
ctccactttcgatgagggtgagatcaaggtgccatttccacacccctccactgatatgtgaatcacaaagcacagttccttattcggttcgataa
acaatattctaaaagactattaaaaccgctcgtttcttgagtttgtgaccgcttgtaaaggctatgcaaatgagTcagtgctgattggctgaaaa
cagccaatcacagctcctatgttgttaTCTAGCcacatacgcgtttcctaggaaaccagagaaggatcaaagcccctctcacacaccg
gggagcggggaagagaactgttttgctttcattgtagaccagtgaaattgggagggttttccgaccgaagtcagaaaacctgCTCCA
AAAATTGCACAATTTTCTAAGGTAAGAATTTgcggaagtgcgtctgtagcgagccagggAaggacatcaa
ctccactttcgatgagggtgagatcaaggtgccatttccacacccctccactgatatgtgaatcacaaagcacagttccttattcggttcgataa
acaatattctaaaagactattaaaaccgctcgtttcttgagtttgtgaccgcttgtaaaggctatgcaaatgagTcagtgctgattggctgaaaa
cagccaatcacagctcctatgttgttaTCTAGCcacatacgcgtttcctaggaaaccagagaaggatcaaagcccctctcacacaccg
gggagcggggaagagaactgttttgctttcattgtagaccagtgaaattgggagggttttccgaccgaagtcagaaaacctgCTCCA
AAAATTtagATGAAAGAGAAGATCTTCAAAAGAAAACttgcggaagtgcgtctgtagcgagccagggA
aggacatcaactccactttcgatgagggtgagatcaaggtgccatttccacacccctccactgatatgtgaatcacaaagcacagttccttatt
cggttcgataaacaatattctaaaagactattaaaaccgctcgtttcttgagtttgtgaccgcttgtaaaggctatgcaaatgagTcagtgctga
ttggctgaaaacagccaatcacagctcctatgttgttatctagagcatggctacgtagataagtagcatggcgggttaatcattaactacaagg
aaccctagtgatggagttgccactccctctctgcgcgctcgctcgctcactgaggccgggcgaccaaaggtcgcccgacgcccgggct
tgcccgggcggcctcagtgagcgagcgagcgcgccagc – 5' (SEQ ID NO: 15)

FIGURE 15A

| Group Number | Viral Titer Delivered (vg) | Age at Injection (months) | | Necropsy @ 3 months |
|---|---|---|---|---|
| 1 | 1.10E+12 | 2 months | N= | 5 (10 TAs) |
| 2 | 3.10E+11 | 2 months | N= | 5 (10 TAs) |
| 3 | 1.10E+11 | 2 months | N= | 5 (10 TAs) |
| 4 | 3.10E+10 | 2 months | N= | 5 (10 TAs) |
| 5 | 1.10E+10 | 2 months | N= | 5 (10 TAs) |
FIGURE 18A
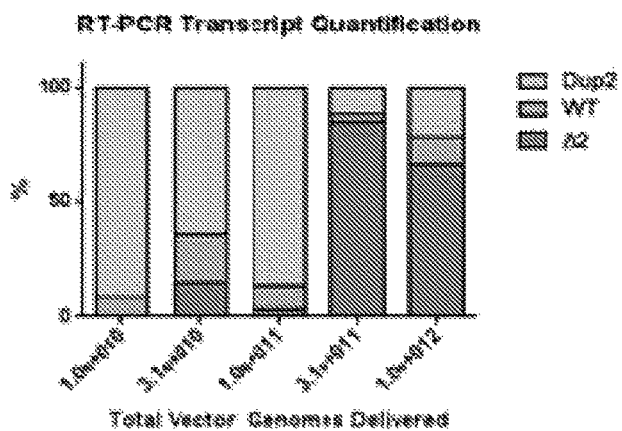
FIGURE 18B
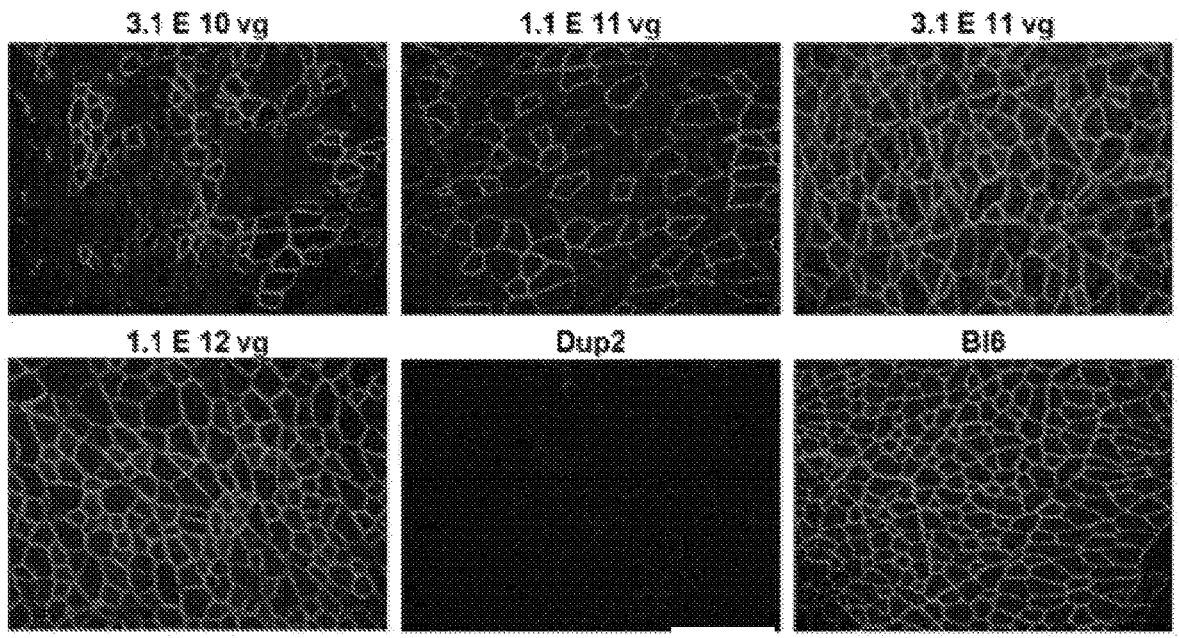
FIGURE 18C

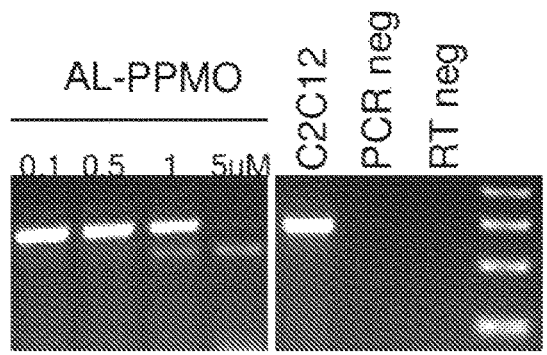
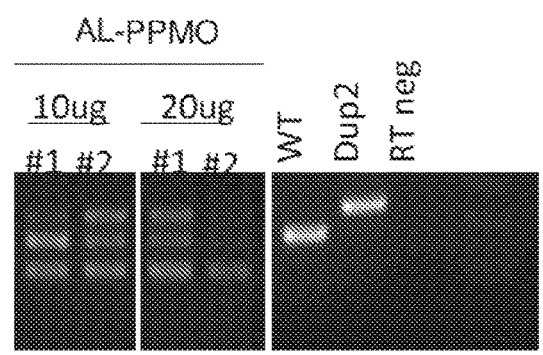
FIGURE 22A
FIGURE 22B
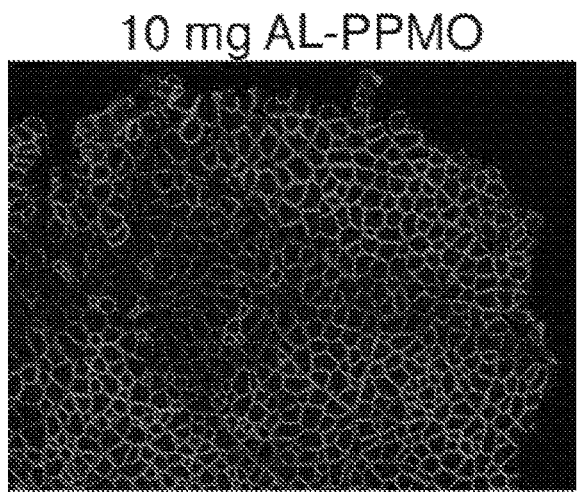
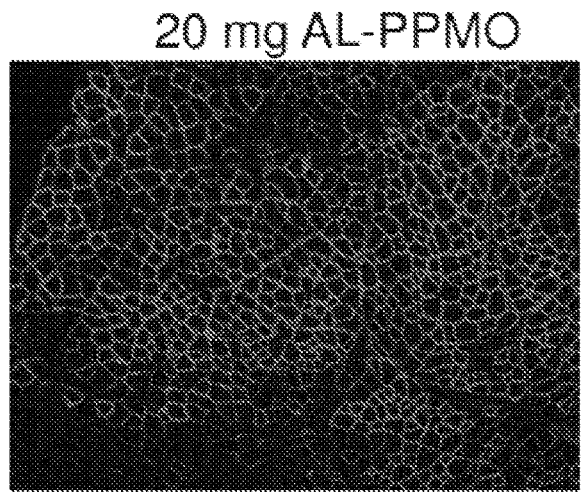
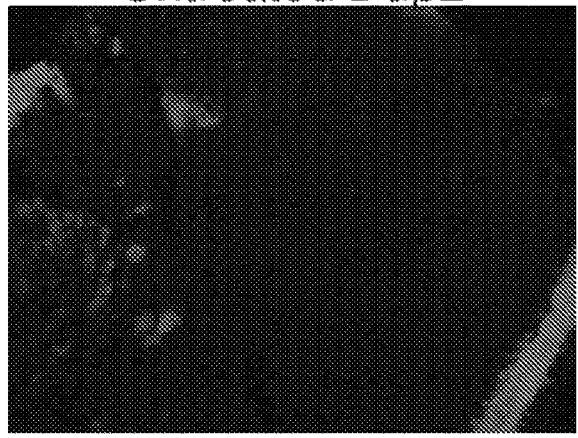
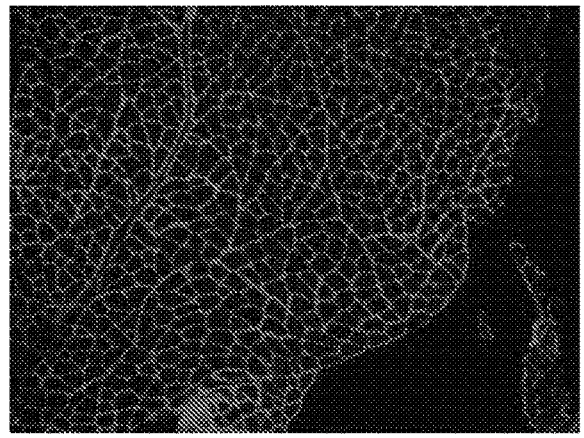
FIGURE 22C / METHODS AND MATERIALS FOR ACTIVATING AN INTERNAL RIBOSOME ENTRY SITE IN EXON 5 OF THE DMD GENE This application claims the benefit of the filing date of U.S. Provisional Patent Application No. 62/035,395 filed Aug. 9, 2014, which is incorporated by reference herein in its entirety.

STATEMENT OF GOVERNMENT INTEREST

This invention was made with Government support under NS043264 awarded by the National Institutes of Health. The government has certain rights in the invention.

INCORPORATION BY REFERENCE OF THE SEQUENCE LISTING

This application contains, as a separate part of disclosure, a Sequence Listing in computer-readable form (filename: 48873 PCT_SeqListing.txt; 20,279 bytes—ASCII text file; created Aug. 6, 2015) which is incorporated by reference herein in its entirety.

FIELD OF THE INVENTION

The present invention relates to the delivery of oligomers for treating patients with a 5' mutation in their DMD gene other than a DMD exon 2 duplication. The invention provides methods and materials for activating an internal ribosome entry site in exon 5 of the DMD gene resulting in a functional truncated isoform of dystrophin. The methods and materials can be used for the treatment of muscular dystrophies arising from 5' mutations in the DMD gene such as Duchenne Muscular Dystrophy or Becker Muscular Dystrophy.

BACKGROUND

Muscular dystrophies (MDs) are a group of genetic diseases. The group is characterized by progressive weakness and degeneration of the skeletal muscles that control movement. Some forms of MD develop in infancy or childhood, while others may not appear until middle age or later. The disorders differ in terms of the distribution and extent of muscle weakness (some forms of MD also affect cardiac muscle), the age of onset, the rate of progression, and the pattern of inheritance.

One form of MD is Duchenne Muscular Dystrophy (DMD). It is the most common severe childhood form of muscular dystrophy affecting 1 in 5000 newborn males. DMD is caused by mutations in the DMD gene leading to absence of dystrophin protein (427 KDa) in skeletal and cardiac muscles, as well as GI tract and retina. Dystrophin not only protects the sarcolemma from eccentric contractions, but also anchors a number of signaling proteins in close proximity to sarcolemma. Many clinical cases of DMD are linked to deletion mutations in the DMD gene. Despite many lines of research following the identification of the DMD gene, treatment options are limited. Corticosteroids are clearly beneficial but even with added years of ambulation the benefits are offset by long-term side effects. The original controlled, randomized, double-blind study reported more than 20 years ago showed benefits using prednisone [Mendell et al., *N. Engl. J. Med.*, 320: 1592-1597 (1989)]. Subsequent reports showed equal efficacy using deflazacort, a sodium-sparing steroid [Biggar et al., *J. Pediatr.*, 138: 45-50 (2001)]. Recent studies also demonstrate efficacy by exon skipping, prolonging walking distance on the 6MWT. Thus far, published clinical studies have reported benefit for only mutations where the reading frame is restored by skipping exon 51 [Cirak et al., *Lancet*, 378: 595-605 (2011) and Goemans et al., *New Engl. J. Med.* 364: 1513-1522 (2011)]. In the only report of a double blind, randomized treatment trial promising results were demonstrated with eteplirsen, a phosphorodiamidate morpholino oligomer (PMO) [Mendell et al., *Annals Neurology*, 74(5): 637-647 (2013)]. In all of these exon-skipping trials, the common denominator of findings has been a plateau in walking ability after an initial modest improvement. Another exon-skipping article is Greer et al., *Molecular Therapy—Nucleic Acids*, 3: 3155 (2014).

See also, U.S. Patent Application Publication Nos. 2012/0077860 published Mar. 29, 2012; 2013/0072541 published Mar. 21, 2013; and 2013/0045538 published Feb. 21, 2013.

In contrast to the deletion mutations, DMD exon duplications account for around 5% of disease-causing mutations in unbiased samples of dystrophinopathy patients [Dent et al., *Am. J. Med. Genet.*, 134(3): 295-298 (2005)], although in some catalogues of mutations the number of duplications is higher [including that published by the United Dystrophinopathy Project in Flanigan et al., *Hum. Mutat.*, 30(12): 1657-1666 (2009), in which it was 11%].

Mutations in the DMD gene result in either the more severe DMD or the milder Becker muscular dystrophy (BMD). The phenotype generally depends upon whether the mutation results in the complete absence of the protein product dystrophin (in DMD) or preserves a reading frame that allows translation of a partially functional dystrophin protein (in BMD) [Monaco, *Trends in Biochemical Sciences*, 14: 412-415 (1989)]. We previously identified a particular BMD founder allele (c.9T>G; p.Trp3X) that did not follow this reading frame rule [Flanigan et al., *Neuromuscular Disorders: NMD*, 19: 743-748 (2009) and Flanigan et al., *Human Mutation*, 30: 1657-1666 (2009)]. Although this nonsense mutation is predicted to result in no protein translation, muscle biopsy revealed significant amounts (~21%) of dystrophin expression of minimally decreased size and the clinical phenotype is one of a very mild dystrophinopathy [Flanigan et al., *Neuromuscular Disorders: NMD*, 19: 743-748 (2009)]. In cellulo and in vitro translation studies demonstrated that in p.Trp3X patients translation is initiated from AUGs in exon 6, suggesting alternate translation initiation as a mechanism of phenotypic amelioration [Gurvich et al., *Human Mutation*, 30: 633-640 (2009)]. Noting that most truncating mutations reported in 5' exons were in fact associated with BMD rather than DMD, we proposed that altered translation initiation may be a general mechanism of phenotypic rescue for 5' mutations in this gene, a prediction supported by subsequent reports [Witting and Vissing, *Neuromuscular Disorders: NMD*, 23: 25-28 (2013) and Flanigan et al., *Neuromuscular Disorders: NMD*, 23: 192 (2013)]. The canonical actin-binding domain 1 (ABD1) was previously proposed to be essential for protein function [Gimona et al., *FEBS Letters*, 513: 98-106 (2002).

Translation initiation is commonly understood to occur by cap-dependent initiation. Internal ribosome entry sites (IRESs) are RNA regulatory sequences that govern cap-independent translation initiation in eukaryotic cells, which is activated when cap-dependent translation is compromised (e.g., during cell stress). Ribosomes are recruited directly to these IRESs on the mRNA and can then continue scanning in a 5' to 3' direction for alternative initiation codons. They were first described in viruses, and among the earliest characterized was the encephalomyocarditis virus (EMCV) IRES. Almost 85 cellular IRESs have been described to date and are mainly located in 5'UTR regions; for example, the 5'UTR of utrophin A, an autosomal homologue of dystrophin, contains an IRES that is both particularly active in regenerating muscle and inducible by exposure to glucocorticoid (the mainstay of therapy for DMD) [Miura et al., *J. Biol. Chem.*, 280: 32997-33005 (2005) and Miura et al., *PloS One*, 3: e2309 (2008)]. However, other eukaryotic IRESs have been described within coding sequences, and some have also been implicated in the modulation of pathology. These include an IRES in the APC gene linked to a mild version of familial adenomatous polyposis coli in which patients with certain 5' mutations still produce a partially functional protein through the use of a downstream initiation codon.

Adeno-associated virus (AAV) is a replication-deficient parvovirus, the single-stranded DNA genome of which is about 4.7 kb in length including 145 nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., *J. Virol.*, 45: 555-564 (1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively (see also U.S. Pat. Nos. 7,282,199 and 7,790, 449 relating to AAV-8); the AAV-9 genome is provided in Gao et al., *J. Virol.*, 78: 6381-6388 (2004); the AAV-10 genome is provided in *Mol. Ther.*, 13(1): 67-76 (2006); and the AAV-11 genome is provided in Virology, 330(2): 375-383 (2004). The sequence of the AAV rh.74 genome is provided herein. Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

There remains a need in the art for treatments for muscular dystrophies including DMD and BMD.

SUMMARY

The present disclosure contemplates methods and products for preventing disease, delaying the progression of disease, and/or treating patients with one or more 5' mutations of the DMD gene. The methods are based on the identification of a glucocorticoid-inducible IRES in exon 5 of the DMD gene, the activation of which can generate a functional N-terminally truncated dystrophin isoform The disclosure contemplates methods of ameliorating Duchenne Muscular Dystrophy or Becker Muscular Dystrophy in a patient with a 5' mutation in the DMD gene comprising the step of administering a DMD exon 5 IRES-activating oligomer construct to the patient, wherein the patient does not have a DMD exon 2 duplication.

In some embodiments of the methods, the DMD exon 5 IRES-activating oligomer construct targets one of the following portions of exon 2 of the DMD gene:

```
                                              (SEQ ID NO: 1)
        5' TCAAAAGAAAACATTCACAAAATGGGTA 3', (SEQ ID NO: 2)
        5' GCACAATTTTCTAAGGTAAGAAT 3', (SEQ ID NO: 3)
        5' TAGATGAAAGAGAAGATGTTCAAAAGAAAAC 3',
        or (SEQ ID NO: 4)
        5' TAGATGAAAGAGAAGATGTTC 3'.
```

In some embodiments of the methods, the DMD exon 5 IRES-activating oligomer construct is a U7snRNA polynucleotide construct in the genome of a recombinant adeno-associated virus. In some of these embodiments, the genome of the recombinant adeno-associated virus lacks adeno-associated virus rep and cap DNA. In some of these embodiments, the virus genome is a self-complementary genome. In some of these embodiments the recombinant adeno-associated virus is a recombinant AAV1 virus, a recombinant AAV6 virus, a recombinant AAV9 virus or a recombinant AAV rh74 virus. In some embodiments, the U7snRNA polynucleotide construct comprises: the U7-B antisense polynucleotide TACCCAT-TTTGCGAATGTTTTCTTTTGA (SEQ ID NO: 5), the U7-C antisense polynucleotide ATTCTTACCT- TAGAAAATTGTGC (SEQ ID NO: 6), the U7-AL antisense polynucleotide GTTTTCTTTTGAAGATCTTCTCTTT-CATCTA (SEQ ID NO: 7), or the U7-AS antisense polynucleotide GAAGATCTTCTCTTTCATCTA (SEQ ID NO: 8).

In some embodiments of the methods, the DMD exon 5 IRES-activating oligomer construct is an antisense oligomer. In some embodiments, the antisense oligomer is an exon 2-targeting antisense oligomer: B antisense oligomer UACCCAUUUUGCGAAUGUUUUCUUUUGA (SEQ ID NO: 9), C antisense oligomer AUUCUUACCUUA-GAAAAUUGUGC (SEQ ID NO: 10), AL antisense oligomer GUUUUCUUUUGAACAUCUUCUCUUU-CAUCUA (SEQ ID NO: 11) or AS antisense oligomer GAACAUCUUCUCUUUCAUCUA (SEQ ID NO:12). In some of these embodiments, the exon 2-targeting antisense oligomer: is a phosphorodiamidate morpholino oligomer (PMO), is a cell penetrating peptide-conjugated PMO (PPMO), is a PMO internalizing peptide (PIP), comprises tricyclo-DNA (tcDNA) or comprises 2'O-methyl-phosphorothioate modifications.

In some embodiments of the methods, the progression of a dystrophic pathology is inhibited in the patient.

In some embodiments of the methods, muscle function is improved in the patient. The improvement in muscle function can be an improvement in muscle strength or an improvement in stability in standing and walking.

In some embodiments, the contemplated methods further comprise administering a glucocorticoid to the patient.

The disclosure contemplates a recombinant adeno-associated virus (AAV) comprising a DMD exon 5 IRES-activating oligomer construct, wherein the DMD exon 5 IRES-activating oligomer construct is a U7snRNA polynucleotide construct comprising: U7-B antisense sequence TACCCATTTTGCGAATGTTTTCTTTTGA (SEQ ID NO: 5), U7-C antisense sequence ATTCTTACCTTAGAAAAT-TGTGC (SEQ ID NO: 6), U7-AL antisense polynucleotide GTTTTCTTTTGAAGATCTTCTCTTTCATCTA (SEQ ID NO: 7), or U7-AS antisense polynucleotide GAA-GATCTTCTCTTTCATCTA (SEQ ID NO: 8). In some embodiments, the genome of the recombinant AAV lacks AAV rep and cap DNA. In some embodiments, the recombinant AAV genome is a self-complementary genome. In some embodiments, the recombinant adeno-associated virus is a recombinant AAV1 virus, a recombinant AAV6 virus, a recombinant AAV9 virus or a recombinant AAV rh74 virus. In some embodiments, the self-complementary genome comprises the DMD exon 5 IRES-activating U7 snRNA polynucleotide construct U7_ACCA (FIG. 15A shows the genome insert 3' to 5' while FIG. 15B shows the reverse complement of the sequence of FIG. 15A).

The disclosure contemplates a DMD exon 5 IRES-activating oligomer construct, wherein the DMD exon 5 IRES-activating oligomer construct is an exon 2-targeting antisense oligomer: B antisense oligomer UACCCAUUUUGCGAAUGUUUUCUUUUGA (SEQ ID NO: 9), C antisense oligomer AUUCUUACCUUA-GAAAAUUGUGC (SEQ ID NO: 10), AL antisense oligomer GUUUUCUUUUGAACAUCUUCUCUUU-CAUCUA (SEQ ID NO: 11) or AS antisense oligomer GAACAUCUUCUCUUUCAUCUA (SEQ ID NO:12). In some embodiments, the exon 2-targeting antisense oligomer: is a phosphorodiamidate morpholino oligomer (PMO), is a cell penetrating peptide-conjugated PMO (PPMO), is a PMO internalizing peptide (PIP), comprises tricyclo-DNA (tcDNA) or comprises 2'O-methyl-phosphorothioate modifications.

BRIEF DESCRIPTION OF THE DRAWING

FIG. 1A-F. Human biopsy samples corroborate translation from exon 6. FIG. 1A shows immunoblot analysis of muscle from an asymptomatic individual with a deletion of exon 2 (DEL2) resulting in a frameshift and premature stop codon p.Tyr11PhefsX7) demonstrates expression of dystrophin of minimally decreased size. Antibodies: NCLDYS1 (rod domain), NCL-DYS2 (C-terminal). FIG. 1B shows sequences from mass spectrometric analysis of dystrophin peptides from muscle biopsy of the deletion exon 2 individual (SEQ ID NO: 28) results in the identification of no peptides encoded prior to M124 (in exon 6), whereas peptides encoded within exon 2, 3, 4 were readily identified in control muscle (Control) (SEQ ID NO: 29). These control peptides of FIG. 1B are found at positions 24-61, 83-104, 125-141, and 196-226 of the dystrophin reference sequence, i.e. UniProt accession number P11532, set out in SEQ ID NO: 27. FIG. 1C shows immunoblot analysis of dystrophin expression of muscle from a BMD patient with a truncating frameshift (FS) mutation in exon 2 (c.40_41del), from a normal control (WT), and from a DMD patient with a duplication of exon 2 (DUP2). In the presence of the premature stop codon induced by the frameshifting mutation, a dystrophin protein of diminished size and amount can be detected using a C-terminal antibody (PA1-21011, Thermo, Inc.; red) but not using an antibody detected to epitopes encoded within exon 1 (Manex1A, green). In contrast, dystrophin is entirely absent in the Dup2 patient. FIG. 1D shows ribosome profiling data was used to compute a translation efficiency (TE) metric for each of the 1000 most abundant transcripts (by mRNA mass) from patient FS (c.40_41del) and normal control muscle. TE value for each gene was calculated from the normalized number of ribosome footprint sequence reads divided by the number of RNA-Seq reads mapped within the coding (CDS) sequence. The rank transcript abundance of the top 1000 genes was computed from the total number of mapped reads per transcript. The subset of genes classified as 'sarcomeric' by Gene Ontology annotation are colored red and the location of the DMD gene is circled. FIG. 1E shows RNA-Seq read depth from muscle total RNA mapped to the 5' region of the DMD gene (hg19, chrX:32,737,599-33,487,390). Read depth for Dp427m exons 1 through 7 was truncated at 40 reads per nucleotide; the exonic read depth ranged from 67 to 91 (FS, c.40_41del) and 58 to 89 (normal) reads per nucleotide. FIG. 1F shows ribosome footprints mapped to the 5' region (nt. 1 to 1500) of the Dp427m (NM_004006.2) transcript. The locations of the exon 1 Dp427m start codon and the c.40_41del mutations are shown, with the short ORF (p.Glu14Argfs*17) as the first CDS segment (green) separated from the remainder of the CDS (green) beginning at the exon 6 alternate AUG (green) initiation codons. Asterisks show the locations of the 9 out-of-frame AUG codons in exons 1 through 5.

FIG. 13 is the rh74 genome sequence (SEQ ID NO: 14) wherein nucleotides 210-2147 are the Rep 78 gene open reading frame, 882-208 are the Rep52 open reading frame, 2079-2081 are the Rep78 stop, 2145-2147 are the Rep78 stop, 1797-1800 are a splice donor site, 2094-2097 are a splice acceptor site, 2121-2124 are a splice acceptor site, 174-181 are the p5 promoter +1 predicted, 145-151 are the p5 TATA box, 758-761 are the p19 promoter +1 predicted, 732-738 are the p19 TATA box, 1711-1716 are the p40 TATA box, 2098-4314 are the VP1 Cap gene open reading frame, 2509-2511 are the VP2 start, 2707-2709 are the VP3 start and 4328-4333 are a polyA signal.

FIG. 15 (b) shows the reverse complement (SEQ ID NO: 26) of the sequence in FIG. 15 (a).

U7 encode for a U7snRNP that share some features with spliceosomal snRNPs. Although it is not involved in pre-mRNA splicing, it processes the 3' ends of histone mRNA (Müller and Schümperli 1997; Dominski and Marzluff 1999). Nucleotides 1-113 of SEQ ID NO: 15 correspond to the 3' ITR, nucleotides 114-220 of SEQ ID NO: 15 correspond to the 3' untranslated region (UTR) (reverse orientation sequence). Nucleotides 221-251 of SEQ ID NO: 15 correspond to SmOPT (reverse orientation sequence). SmOPT is a modification of the original Sm-binding site of U7 snRNA with a consensus sequence derived from spliceosomal snRNAs (Grimm et al. 1993; Stefanovic et al. 1995a). Nucleotides 252-262 of SEQ ID NO: 15 correspond to a loop (reverse orientation sequence). Nucleotides 263-295 correspond to U7-Along (reverse orientation sequence), which is an antisense sequence that targets the acceptor site of exon 2. Nucleotides 296-551 of SEQ ID NO: 15 correspond to U7 (reverse orientation sequence), nucleotides 558-664 of SEQ ID NO: 15 correspond to 3' UTR (reverse orientation sequence), nucleotides 665-695 of SEQ ID NO: 15 correspond to SmOPT (reverse orientation sequence), and nucleotides 696-706 of SEQ ID NO: 15 correspond to a loop (reverse orientation sequence). Nucleotides 707-731 of SEQ ID NO: 15 correspond to U7-C (reverse orientation sequence), which is an antisense sequence that targets the donor site of exon 2. Nucleotides 732-987 of SEQ ID NO: 15 correspond to U7 (reverse orientation sequence), nucleotides 994-1100 of SEQ ID NO: 15 correspond to 3' UTR (reverse orientation sequence), nucleotides 1111-1131 of SEQ ID NO: 15 correspond to SmOPT (reverse orientation sequence), nucleotides 1132-1142 of SEQ ID NO: 15 correspond to a loop (reverse orientation sequence), nucleotides 1143-1167 of SEQ ID NO: 15 correspond to U7-C (reverse orientation sequence), nucleotides 1168-1423 of SEQ ID NO: 15 correspond to U7 (reverse orientation sequence), nucleotides 1430-1536 of SEQ ID NO: 15 correspond to 3' UTR (reverse orientation sequence), nucleotides 1537-1567 of SEQ ID NO: 15 correspond to SmOPT (reverse orientation sequence), nucleotides 1568-1578 of SEQ ID NO: 15 correspond to a loop (reverse orientation sequence), nucleotides 1579-1611 of SEQ ID NO: 15 correspond to U7-Along (reverse orientation sequence), nucleotides 1612-1867 of SEQ ID NO: 15 correspond to U7 (reverse orientation sequence) and nucleotides 1920-2052 of SEQ ID NO: 15 correspond to the ITR.

Figure 16:
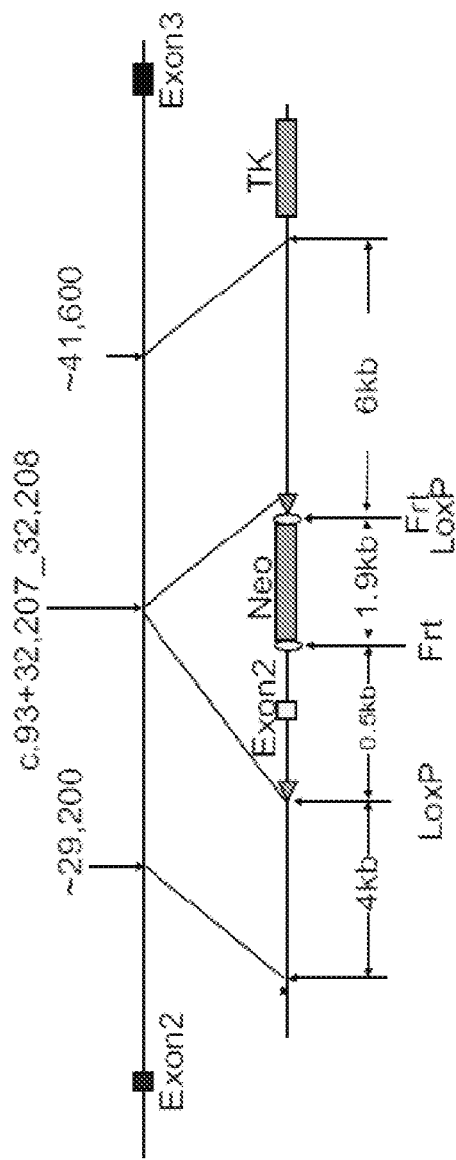
Figure 17B:
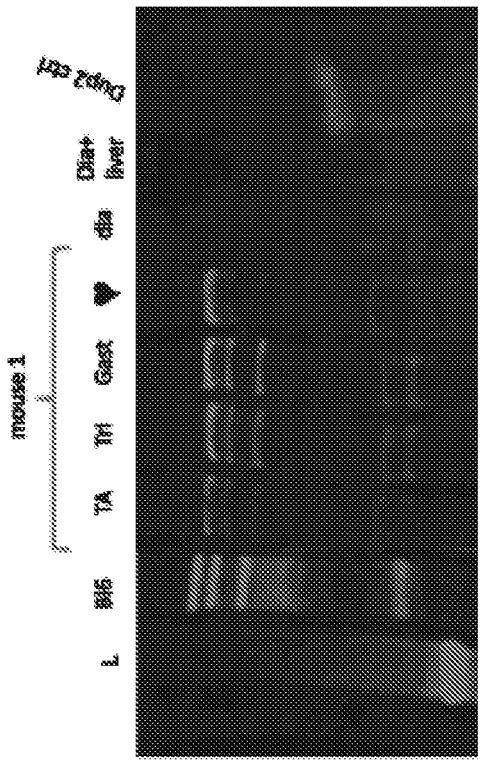
Figure 17A:
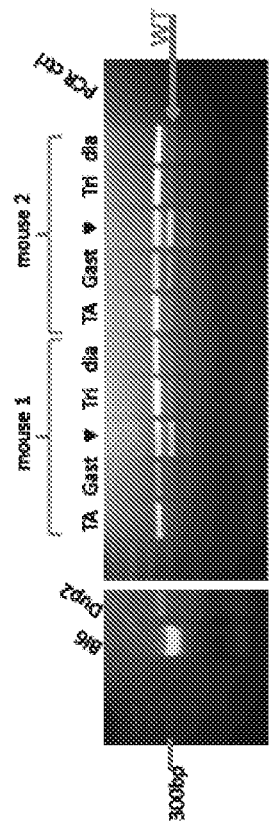
Figure 17C:
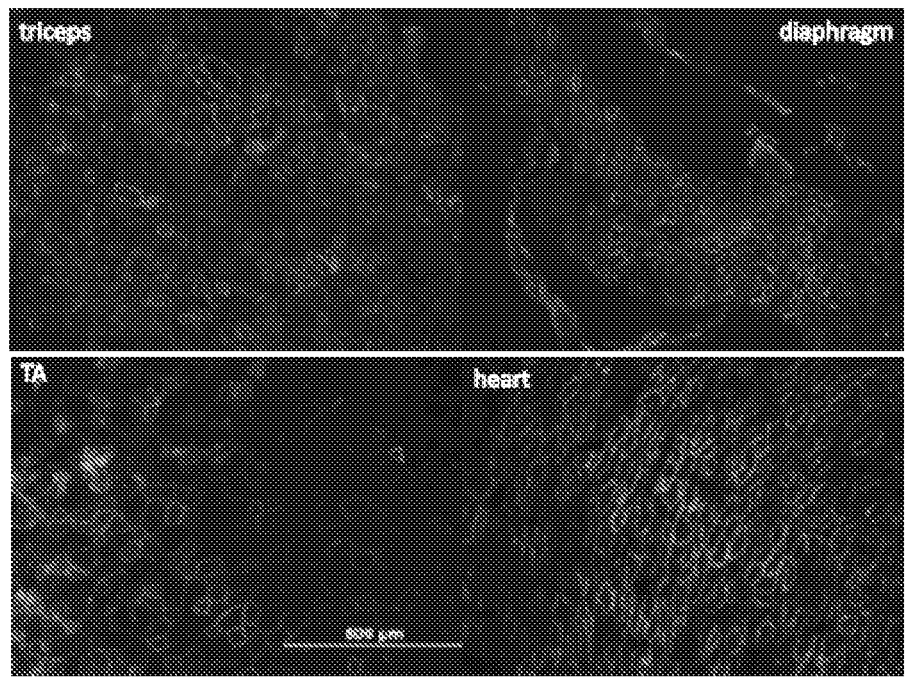
Figure 17D:
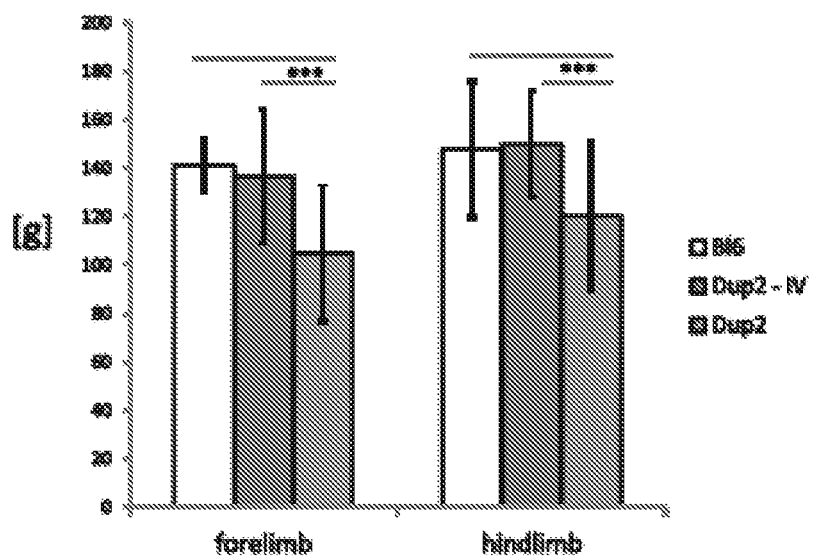
Figure 17E:
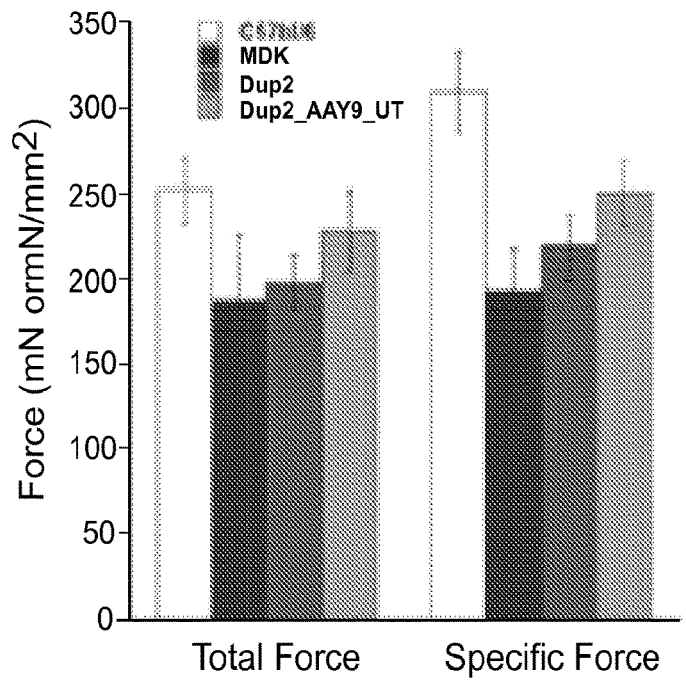
Figure 17F:
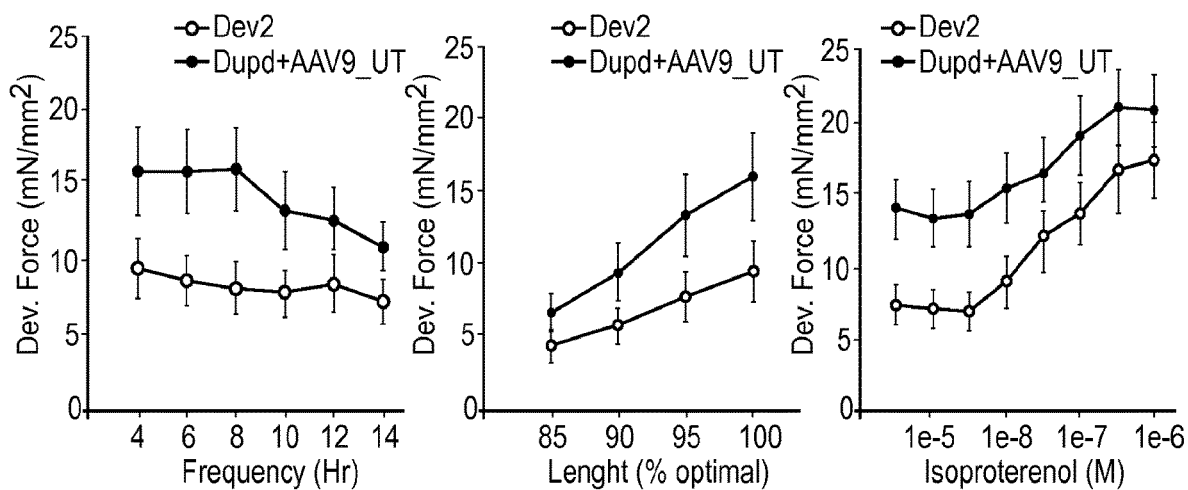

FIG. 16 shows a schematic of a vector used in creation of a mdx$^{dup2}$ (Dup2) mouse.

FIG. 17 shows (a) RT-PCR performed on 5 different Dup2 mouse muscles one month after tail vein injection of AAV9.U7-ACCA (3.3E12 vg/kg). As demonstrated by the presence of multiple transcripts (here labeled Dup2, wt, and Del2), U7-ACCA treatment is able to force skipping of one or both copies of exon 2 in all muscles tested. (TA: tibialis anterior; Gas: gastrocnemius; ♥: heart; Tri: triceps; dia: diaphragm) (b) Western blot performed on 5 different muscles one month after injection demonstrates the presence of dystrophin in all tested muscles. (c) Immunostaining of dystrophin on the same samples confirms dystrophin expression and its proper localization at the sarcolemma. (d) Evaluation of both forelimb and hindlimb grip strength demonstrates a complete correction of grip strength in Dup2 animals treated with AAV9.U7-ACCA. (e) Normalized specific and total forces following tetanic contraction show improvement in muscle force in comparison to untreated Dup2 animals. (f) Cardiac papillary muscles demonstrate improvements in length-dependent force generation in treated animals.

FIG. 18. (a) IM study design. Escalating doses of the AAV9.U7snRNA-ACCA vector were delivered to the tibialis anterior muscle at 2 months, and muscle analyzed at 3 months by mRNA, protein, and electrophysiology studies. (b) Quantification of mRNA by RT-PCR at ascending dose levels of IM injection. Transcripts contain either two (Dup2), one (WT), or zero copies ($\Delta$2) of exon 2. Expression of the N-truncated dystrophin following ascending dose levels of IM injection. Protein expression by (c) immunofluorescence or (d) immunoblot demonstrates a dose response. (e) Quantification of the immunoblot suggests maximal protein expression at 3.1E11 vg. Amelioration of deficits in absolute force (f), specific force (g), in response to eccentric contraction following IM injection into the tibialis anterior muscle of 3.1E11 vg.

FIG. 19. (a) IV study design. Escalating doses of the AAV9.U7snRNA-ACCA vector were delivered systemically at 2 months, and muscle analyzed at 3 months by mRNA, protein, and electrophysiology studies. (b) Quantification of mRNA by RT-PCR at ascending dose levels of IV injection. Transcripts contain either two (Dup2), one (WT), or zero copies ($\Delta$2) of no exon 2. (c) Quantification of dystrophin by immunoblot following IV injection. Expression follows a dose response, with expression in triceps lagging that in heart and diaphragm. (d) Immunostaining of dystrophin from Bl6 and Dup2. (e) expression following IV injection. A dose response is seen, with significant dystrophin expression in the heart and diaphragm at higher doses.

Figure 20:
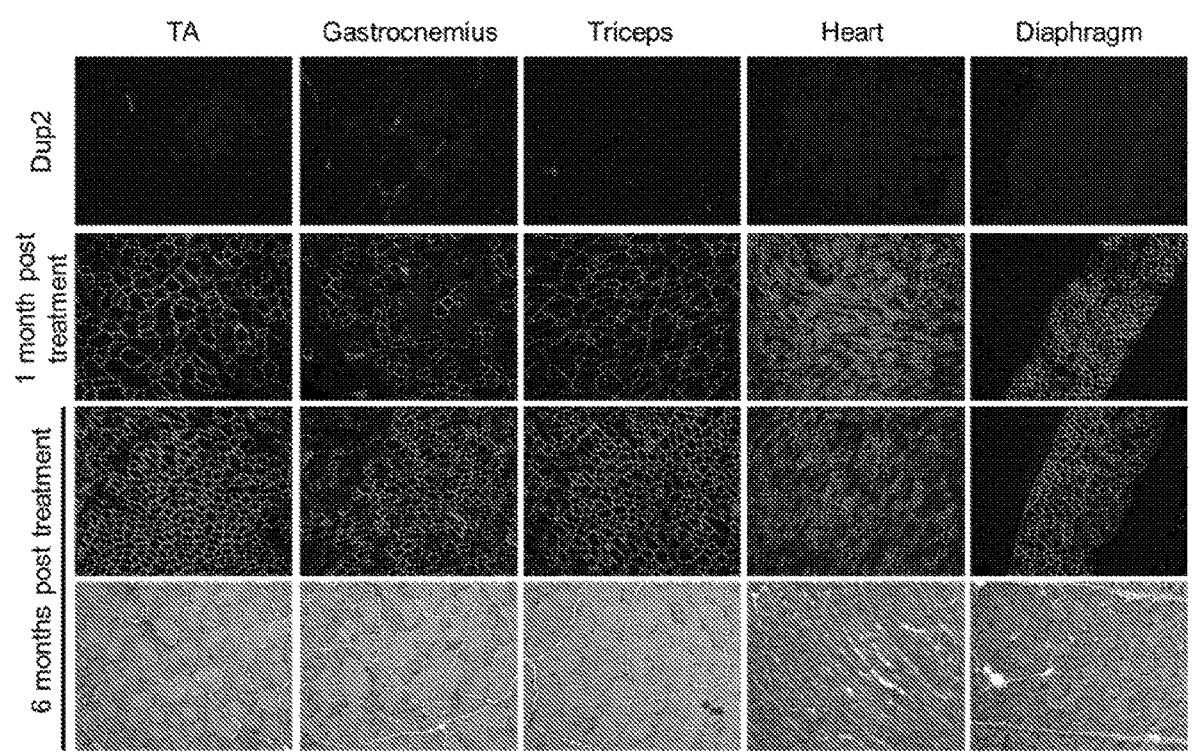

FIG. 20. Early injection of AAV9.U7-ACCA prevents the muscle pathology in the Dup2 mouse. Immunostaining of dystrophin demonstrates production and localization of N-terminally truncated dystrophin at the plasma membrane. No centronucleation was observed following hematoxylin and eosin staining. By 6 months of age, untreated Dup2 mice typically demonstrate 60% of their fibers with central nuclei (data not shown).

Figure 21:
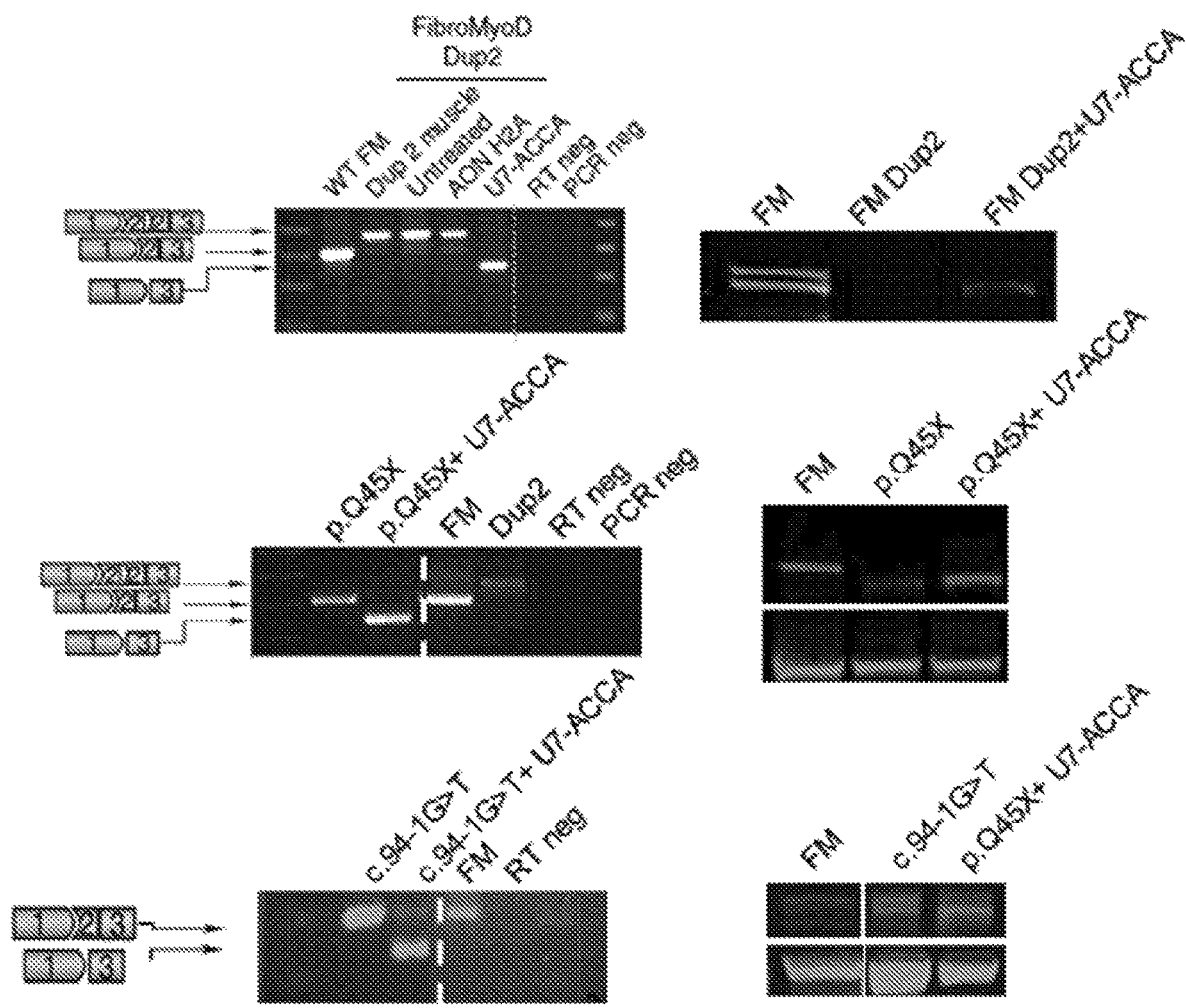

FIG. 21. Generation of alternative N-terminally truncated dystrophins in human cell lines derived from patients carrying mutations within the first nine exons. RT-PCR results after skipping of exon 2 using either AAV1.U7-ACCA vector (1×10E11 vector genomes) or H2A antisense oligonucleotide (AON H2A) in various patient cell lines carrying mutation within exon 1 to 4. This results in approximately 90% of transcript lacking exon 2 (quantification not shown). FM=FibroMyoD cells derived from healthy human subject. Immunoblot performed 14 d after infection of FibroMyod cells with AAV1.U7-ACCA shows expression of the N-terminally truncated dystrophin protein. A smaller band of approximately 390 kDa is detected in every lane but is nonspecific (as seen in the untreated sample) and does not correspond to the IRES-driven isoform. (The image was assembled for clarity, with wild-type contrast altered to clearly show bands.)

FIG. 22. Expression of the N-truncated dystrophin following treatment with PPMO antisense oligonucleotide. (a) transfection in C2C12 mouse myoblasts or (b) intramuscular injection into Dup2 mouse tibialis anterior muscles of AL-PPMO. RT-PCR results from treated cells or muscles demonstrate an efficient skipping of exon 2. (c) immunofluorescence of dystrophin shows expression of a plasma membrane protein following intramuscular injection of AL-PPMO antisense oligonucleotide.

DESCRIPTION

As noted above, the present disclosure contemplates methods and products for preventing, delaying the progression of, and/or treating patients with one or more 5' mutations of the DMD gene that are based on the activation of a glucocorticoid-inducible IRES in exon 5 of the DMD gene. The activation of the inducible IRES in exon 5 of the DMD gene generates a functional N-terminally truncated dystrophin isoform.

As used herein, a "5' mutation of the DMD gene" is a mutation within or affecting exon 1, 2, 3 or 4 of the DMD gene. In the methods of the invention, the patients treated do not have a DMD exon 2 duplication, but a "mutation affecting exon 1, 2, 3 or 4" as contemplated herein can be a duplication other than a DMD exon 2 duplication.

In one aspect, the methods involve using an "DMD exon 5 IRES-activating oligomer construct." As used herein, a DMD exon 5 IRES-activating oligomer construct targets exon 2 to induce altered splicing that results in the exclusion of exon 2 from the mature RNA causing a frameshift in the DMD gene reading frame and inducing utilization of the IRES in exon 5 for translational initiation.

In some embodiments, the DMD exon 5 IRES-activating oligomer construct targets one of the following portions (shown 5' to 3') of exon 2 of the DMD gene.

```
                                          (SEQ ID NO: 1)
B:  TCAAAAGAAAACATTCACAAAATGGGTA  (+17 + 44)

(SEQ ID NO: 2)
C:  GCACAATTTTCTAAGGTAAGAAT  (+48 - 8)

(SEQ ID NO: 3)
AL: TAGATGAAAGAGAAGATGTTCAAAAGAAAAC  (-3 + 28)

(SEQ ID NO: 4)
AS: TAGATGAAAGAGAAGATGTTC  (-3 + 18)
```

In some embodiments, a rAAV is used to deliver a U7 small nuclear RNA polynucleotide construct that is targeted to DMD exon 2 by an antisense polynucleotide. In some embodiments, the U7 small nuclear RNA is a human U7 small nuclear RNA. In some embodiments, the polynucleotide construct is inserted in the genome of a rAAV9, the genome of a rAAV6 or the genome of a rAAVrh74. In some embodiments, the U7 small nucleotide RNA construct comprises exemplary targeting antisense polynucleotides including, but not limited to the following where, for example, the "U7-AL antisense polynucleotide" is respectively complementary to and targets the "AL" exon 2 sequence in the preceding paragraph.

```
U7-B antisense polynucleotide:
TACCCATTTTGCGAATGTTTTCTTTTGA      (SEQ ID NO: 5)

U7-C antisense polynucleotide:
ATTCTTACCTTAGAAAATTGTGC           (SEQ ID NO: 6)

U7-AL antisense polynucleotide:
GTTTTCTTTTGAAGATCTTCTCTTTCATCTA   (SEQ ID NO: 7)

U7-AS antisense polynucleotide:
GAAGATCTTCTCTTTCATCTA             (SEQ ID NO: 8)
```

In some embodiments, the DMD exon 5 IRES-activating oligomer construct is an exon 2-targeting antisense oligomer. In some embodiments, the antisense oligomers are contemplated to include modifications compared to the native phosphodiester oligodeoxynucleotide polymer to limit their nuclease sensitivity. Contemplated modifications include, but are not limited to, phosphorodiamidate morpholino oligomers (PPOs), cell penetrating peptide-conjugated PMOs (PPMOs), PMO internalizing peptides (PIP) [(Betts et al., Sci. Rep., 5: 8986 (2015)], tricyclo-DNA (tcDNA) [Goyenvalle et al., Nat. Med., 21: 270-275 (2015)] and 2'O-methyl-phosphorothioate modifications. Exemplary DMD exon 5 IRES-activating oligomer constructs that are exon 2-targeting antisense oligomers include, but are not limited to, the following antisense oligomers (shown 5' to 3') where, for example, the "B antisense oligomer" respectively targets the "B" exon 2 target in paragraph [0032].

```
B antisense oligomer:
UACCCAUUUUGCGAAUGUUUUCUUUUGA      (SEQ ID NO: 9)

C antisense oligomer:
AUUCUUACCUUAGAAAAUUGUGC           (SEQ ID NO: 10)

AL antisense oligomer:
GUUUUCUUUUGAACAUCUUCUCUUUCAUCUA   (SEQ ID NO: 11)

AS antisense oligomer:
GAACAUCUUCUCUUUCAUCUA             (SEQ ID NO: 12)

H2A (+12 + 41):
CCAUUUUGUGAAUGUUUUCUUUUGAACAUC    (SEQ ID NO: 13)
```

In another aspect, a method of ameliorating a muscular dystrophy (such as DMD or BMD) in a patient with a 5' mutation of the DMD gene is provided. In some embodiments, the method comprises the step of administering a rAAV to the patient, wherein the genome of the rAAV comprises a DMD exon 5 IRES-activating oligomer construct. In some embodiments, the method comprises the step of administering a DMD exon 5 IRES-activating oligomer construct that is an exon 2-targeting antisense oligomer. In some embodiments, the patient is also treated with a glucocorticoid.

In yet another aspect, the invention provides a method of inhibiting the progression of dystrophic pathology associated with a muscular dystrophy (such as DMD or BMD). In some embodiments, the method comprises the step of administering a rAAV to a patient with a 5' mutation of the DMD gene, wherein the genome of the rAAV comprises a DMD exon 5 IRES-activating oligomer construct. In some embodiments, the method comprises the step of administering a DMD exon 5 IRES-activating oligomer construct that is an exon 2-targeting antisense oligomer. In some embodiments, the patient is also treated with a glucocorticoid.

In still another aspect, a method of improving muscle function in a patient with a 5' mutation of the DMD gene is provided. In some embodiments, the method comprises the step of administering a rAAV to the patient, wherein the genome of the rAAV comprises a DMD exon 5 IRES-activating oligomer construct. In some embodiments, the method comprises the step of administering a DMD exon 5 IRES-activating oligomer construct that is an exon 2-targeting antisense oligomer. In some embodiments, the improvement in muscle function is an improvement in muscle strength. The improvement in muscle strength is determined by techniques known in the art such as the maximal voluntary isometric contraction testing (MVICT). In some instances, the improvement in muscle function is an improvement in stability in standing and walking. The improvement in stability strength is determined by techniques known in the art such as the 6-minute walk test (6MWT) or timed stair climb. In some embodiments, the patient is also treated with a glucocorticoid.

In another aspect, the invention provides a method of delivering a DMD exon 5 IRES-activating oligomer construct to an animal (including, but not limited to, a human) with a 5' mutation of the DMD gene. In some embodiments, the method comprises the step of a rAAV to the patient, wherein the genome of the rAAV comprises a DMD exon 5 IRES-activating oligomer construct. In some embodiments, the method comprises the step of administering a DMD exon 5 IRES-activating oligomer construct that is an exon 2-targeting antisense oligomer. In some embodiments, the animal is also treated with a glucocorticoid.

Cell transduction efficiencies of the methods of the invention described herein may be at least about 60, about 65, about 70, about 75, about 80, about 85, about 90 or about 95 percent.

In some embodiments of the foregoing methods of the invention, the virus genome is a self-complementary genome. In some embodiments of the methods, the genome of the rAAV lacks AAV rep and cap DNA. In some embodiments of the methods, the rAAV is a SC rAAV U7_ACCA comprising the exemplary genome set out in FIG. 15. In some embodiments, the rAAV is a rAAV6. In some embodiments, the rAAV is a rAAV9. In some embodiments the rAAV is a rAAV rh74 (FIG. 13).

In yet another aspect, the invention provides a rAAV comprising the AAV rAAV9 capsid and a genome comprising the exemplary DMD exon 5 IRES-activating U7 snRNA polynucleotide construct U7_ACCA. In some embodiments, the genome of the rAAV lacks AAV rep and cap DNA. In some embodiments, the rAAV comprises a self-complementary genome. In some embodiments of the methods, the rAAV is a SC rAAV U7_ACCA comprising the exemplary genome is set out in FIG. 15. In some embodiments, the rAAV is a rAAV6. In some embodiments, the rAAV is a rAAV9. In some embodiments the rAAV is a rAAV rh74 (FIG. 13).

Recombinant AAV genomes of the invention comprise one or more AAV ITRs flanking at least one DMD exon 5 IRES-activating U7 snRNA polynucleotide construct. Genomes with DMD exon 5 IRES-activating U7 snRNA polynucleotide constructs comprising each of the targeting antisense sequences set out in paragraph [0033] are specifically contemplated, as well as genomes with DMD exon 5 IRES-activating U7 snRNA polynucleotide constructs comprising each possible combination of two or more of the targeting antisense sequences set out in paragraph [0033]. In some embodiments, including the exemplified embodiments, the U7 snRNA polynucleotide includes its own promoter. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10, AAV-11 and AAV rh.74. As noted in the Background section above, the nucleotide sequences of the genomes of various AAV serotypes are known in the art. In some embodiments of the invention, the promoter DNAs are muscle-specific control elements, including, but not limited to, those derived from the actin and myosin gene families, such as from the myoD gene family [See Weintraub et al., Science, 251: 761-766 (1991)], the myocyte-specific enhancer binding factor MEF-2 [Cserjesi and Olson, Mol. Cell. Biol., 11: 4854-4862 (1991)], control elements derived from the human skeletal actin gene [Muscat et al., Mol. Cell. Biol., 7: 4089-4099 (1987)], the cardiac actin gene, muscle creatine kinase sequence elements [Johnson et al., Mol. Cell. Biol., 9:3393-3399 (1989)] and the murine creatine kinase enhancer (MCK) element, desmin promoter, control elements derived from the skeletal fast-twitch troponin C gene, the slow-twitch cardiac troponin C gene and the slow-twitch troponin I gene: hypoxia-inducible nuclear factors [Semenza et al., Proc. Natl. Acad. Sci. USA, 88: 5680-5684 (1991)], steroid-inducible elements and promoters including the glucocorticoid response element (GRE) [See Mader and White, Proc. Natl. Acad. Sci. USA, 90: 5603-5607 (1993)], and other control elements.

DNA plasmids of the invention comprise rAAV genomes of the invention. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11 and AAV rh74. Use of cognate components is specifically contemplated. Production of pseudotyped rAAV is disclosed in, for example, WO 01/83692 which is incorporated by reference herein in its entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing [Samulski et al., *Proc. Natl. Acad. S6. USA*, 79:2077-2081 (1982)], addition of synthetic linkers containing restriction endonuclease cleavage sites [Laughlin et al., *Gene*, 23:65-73 (1983)] or by direct, blunt-end ligation [Senapathy & Carter, *J. Biol. Chem.*, 259:4661-4666 (1984)]. The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, *Current Opinions in Biotechnology*, 1533-1539 (1992); and Muzyczka, *Curr. Topics in Microbial. and Immunol.*, 158:97-129 (1992). Various approaches are described in Ratschin et al., *Mol. Cell. Biol.*, 4:2072 (1984); Hermonat et al., *Proc. Natl. Acad. Sci. USA*, 81:6466 (1984); Tratschin et al., *Mol. Cell. Biol.* 5:3251 (1985); McLaughlin et al., *J. Virol.*, 62:1963 (1988); and Lebkowski et al., *Mol. Cell. Biol.*, 7:349 (1988). Samulski et al., *J. Virol.*, 63:3822-3828 (1989); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al., *Vaccine*, 13:1244-1250 (1995); Paul et al., *Human Gene Therapy*, 4:609-615 (1993); Clark et al., *Gene Therapy*, 3:1124-1132 (1996); U.S. Pat. Nos. 5,786,211; 5,871,982; and 6,258,595. The foregoing documents are hereby incorporated by reference in their entirety herein, with particular emphasis on those sections of the documents relating to rAAV production.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

The rAAV may be purified by methods standard in the art such as by column chromatography or cesium chloride gradients. Methods for purifying rAAV vectors from helper virus are known in the art and include methods disclosed in, for example, Clark et al., *Hum. Gene Ther.*, 10(6): 1031-1039 (1999); Schenpp and Clark, *Methods Mol. Med.*, 69:427-443 (2002); U.S. Pat. No. 6,566,118 and WO 98/09657.

In another embodiment, the invention contemplates compositions comprising a DMD exon 5 IRES-activating oligomer construct of the present invention in a viral delivery vector or other delivery vehicle. Compositions of the invention comprise a pharmaceutically acceptable carrier. The compositions may also comprise other ingredients such as diluents. Acceptable carriers and diluents are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

Sterile injectable solutions are prepared by incorporating the active ingredient in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about $1 \times 10^6$, about $1 \times 10^7$, about $1 \times 10^8$, about $1 \times 10^9$, about $1 \times 10^{10}$, about $1 \times 10^{11}$, about $1 \times 10^{12}$, about $1 \times 10^{13}$ to about $1 \times 10^{14}$ or more DNase resistant particles (DRP) per ml. Dosages may also be expressed in units of viral genomes (vg) (i.e., $1 \times 10^7$ vg, $1 \times 10^8$ vg, $1 \times 10^9$ vg, $1 \times 1010$ vg, $1 \times 10^{11}$ vg, $1 \times 10^{1}2$ vg, $1 \times 10^{13}$ vg, $1 \times 10^{14}$ vg, respectively).

Methods of transducing a target cell (e.g., a skeletal muscle) of a patient with a 5' mutation of the DMD gene with a rAAV of the invention, in vivo or in vitro, are contemplated herein. The methods comprise the step of administering an effective dose, or effective multiple doses, of a composition comprising a rAAV of the invention to an animal (including a human being) with a 5' mutation of the DMD gene. If the dose is administered prior to development of DMD, the administration is prophylactic. If the dose is administered after the development of DMD, the administration is therapeutic. In embodiments of the invention, an "effective dose" is a dose that alleviates (eliminates or reduces) at least one symptom associated with DMD being treated, that slows or prevents progression to DMD, that slows or prevents progression of a disorder/disease state, that diminishes the extent of disease, that results in remission (partial or total) of disease, and/or that prolongs survival.

Administration of an effective dose of the compositions may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of rAAV (in particular, the AAV ITRs and capsid protein) of the invention may be chosen and/or matched by those skilled in the art taking into account the infection and/or disease state being treated and the target cells/tissue(s). In some embodiments, the route of administration is intramuscular. In some embodiments, the route of administration is intravenous.

Combination therapies are also contemplated by the invention. Combination therapy as used herein includes simultaneous treatment or sequential treatments. Combinations of methods of the invention with standard medical treatments (e.g., corticosteroids and/or immunosuppressive drugs) are specifically contemplated, as are combinations with other therapies such as those mentioned in the Background section above. In some embodiments, the corticosteroid is a glucocorticoid such as prednisone, deflazacort or Medrol (6-methyl-prednisolone; PDN).

EXAMPLES

Aspects and embodiments of the invention are illustrated by the following examples.

Most mutations that truncate the reading frame of the DMD gene cause loss of dystrophin expression and lead to DMD. However, amelioration of disease severity can result from alternate translation initiation beginning in DMD exon 6 that leads to expression of a highly functional N-truncated dystrophin. This novel isoform results from usage of an IRES within exon 5 that is glucocorticoid-inducible. IRES activity was confirmed in patient muscle by both peptide sequencing and ribosome profiling as described below. Generation of a truncated reading frame upstream of the IRES by exon skipping led to synthesis of a functional N-truncated isoform in both patient-derived cell lines and in a DMD mouse model, where expression protects muscle from contraction-induced injury and corrects muscle force to the same level as control mice. These results support a novel therapeutic approach for patients with mutations within the 5' exons of the DMD gene. See also, Wein et al., *Abstracts/Neuromuscular Disorders*, 23: 738-852 (2013).

Example 1

Evidence for IRES-Induced Translation from Human Muscle Samples

We previously published that nonsense and frameshifting mutations leading to a stop codon within at least the first two DMD exons should result in the mild BMD phenotype via exon 6 translation initiation [Gurvich et al., *Human Mutation*, 30: 633-640 (2009)]. However, duplication of exon 2—which is the most common single exon duplication and results in a premature stop codon within the duplicated exon 2 sequence—would seem to be an exception to this prediction, as it is usually associated with DMD [White et al., *Human Mutation*, 27: 938-945 (2006)]. However, a deletion of exon 2, which also results in a premature stop codon, has not been described, either in our large cohort [Flanigan et al., *Human Mutation*, 30: 1657-1666 (2009)] or in other large publicly available catalogues (www.dmd.nl). We interpreted this lack of reported cases to mean that the clinical features in patients with exon 2 deletions are either asymptomatic or exceedingly mild due to expression of the N-truncated isoform.

Figure 1A:
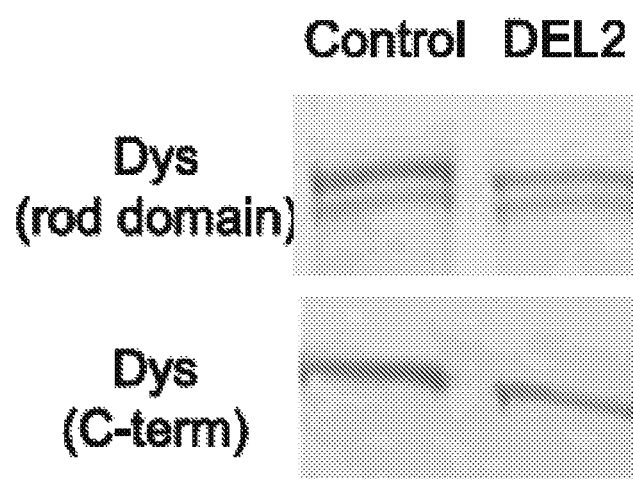
Figure 7A:
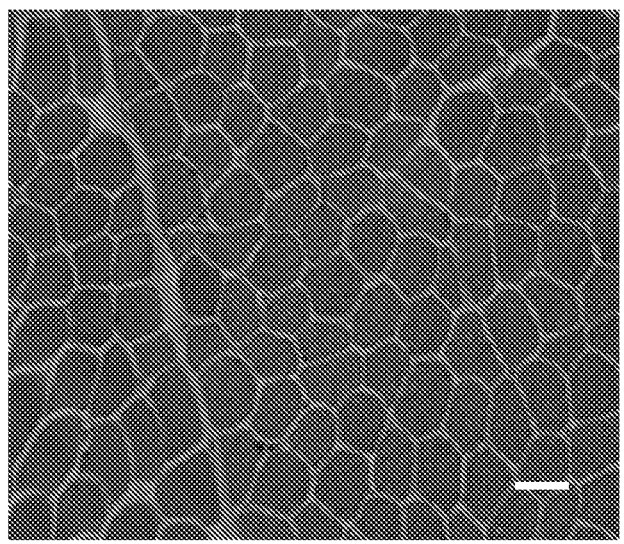
FIG. 7. Mutational analysis in the deletion exon 2 asymptomatic boy. (a) H&E-stained muscle section from the patient with deletion of exon 2 (DEL2) reveals an absence of dystrophic features. (b) Immunohistochemical staining of muscle sections from the same patient using NCL-DYS3 antibody (exons 10-12). Manex1A staining (exon 1 specific) was not performed at that time, and tissue is no longer available. (c) CGH profile of the genomic context (top panel) and of the entire X chromosome (bottom panel) of the 12.983 bp deletion including exon 2 (shown in the overlay track at the bottom of the top panel). (d) Alignment of the sequenced junction with the reference genome sequence (NCBI hg18) (SEQ ID NOs: 31-33, respectively). Proximal and distal reference sequences are colored differently and the junction is in black. Vertical bars between the sequences represent sequence homology. A microhomology of 5 bp (CTGTG, shown a box) is found at the junction between the distal and proximal sequences, characteristic for non-homologous end joining. (e) Genomic sequences of the breakpoint with the microhomology sequence underlined in blue (SEQ ID NO: 34). (f,g) RT-PCR and sequencing results confirm the deletion of exon 2 at RNA level.
Figure 7B:
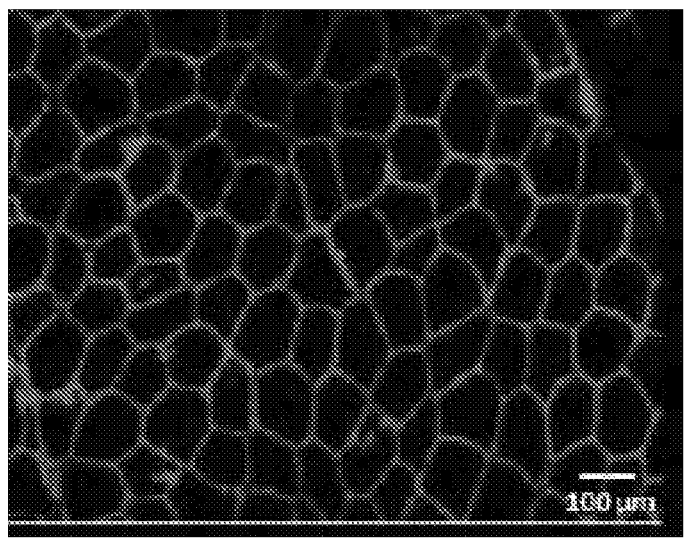

This interpretation was confirmed by the detection of a deletion of exon 2 (DEL2) in an Italian boy who first presented at age 6 years for evaluation of an incidentally detected elevation of serum creatine kinase (550 iu/I; normal value <200 iu/I). Normal early motor milestones were reported and no muscle dystrophy was ever reported in the family. His neurological examination was entirely normal at 15 years of age. Muscle biopsy showed slight fiber size variability (FIG. 7a), and in some sections an increased number of central nuclei along with some densely stained hypercontracted fibers. Immunofluorescent analysis using a C-terminal antibody showed the presence of dystrophin at the membrane (FIG. 7b). Interestingly, western blot revealed that the detected dystrophin had a smaller molecular weight (~410 kDa) (FIG. 1a), and mutational analysis revealed a deletion of exon 2 (FIG. 7c-g). Subsequent peptide sequencing using tandem mass spectrometry (LC-MS/MS)[20] confirmed the absence of any residues encoded by exons 1 through 5 among the 99 unique peptides detected and matched to dystrophin, consistent with translation initiation within exon 6 (FIG. 1b and Table 1).

TABLE 1

Peptide spectrum match in human muscle. Dystrophin peptides encoded in exons 1-10. (N) represents the number of times a peptide sequence was detected in normal control muscle or in muscle from the patient with a deletion of exon 2.

| | | | Dystrophin Peptide Spectrum Match (N) | | |
|---|---|---|---|---|---|
| Peptide sequence | MW [Da] | Exon | Normal control muscle | Del2 Muscle | SEQ ID NO |
| WVNAQFSK | 979,5009 | 2 | 1 | 0 | 16 |
| QHIENLFSDLQDGR | 1671,8084 | 3 | 1 | 0 | 17 |
| LLDLLEGLTGQK | 1299,7520 | 4 | 1 | 0 | 18 |
| VLQNNNVDLVNIGSTDIVDGNHK | 2478,2521 | 4-5 | 2 | 0 | 19 |
| NLMAGLQQTNSEK | 1449,6990 | 6 | 3 | 0 | 20 |
| LEHAFNIAR | 1070,5737 | 7 | 1 | 0 | 21 |
| YQLGIEK | 850,4665 | 7 | 1 | 1 | 22 |
| LLDPEDVDTTYPDKK | 1748,8606 | 7-8 | 2 | 3 | 23 |
| SYAYTQAAYVTTSDPTR | 1894,8820 | 9 | 3 | 2 | 24 |
| SPFPSQHLEAPEDK | 1581,7538 | 9-10 | 3 | 1 | 25 |

Figure 1C:
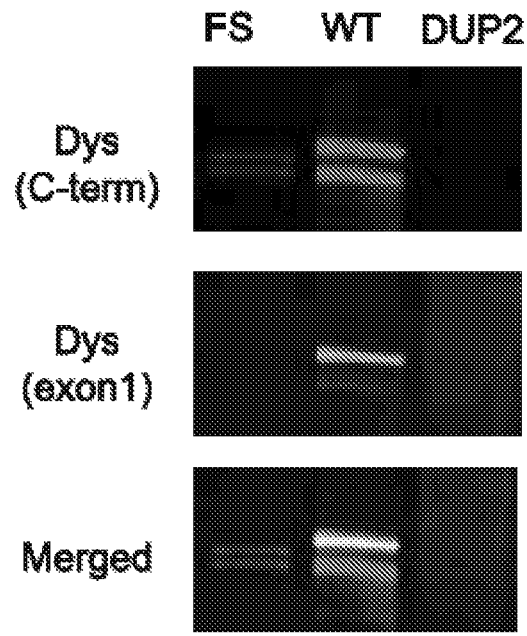
Figure 1D:
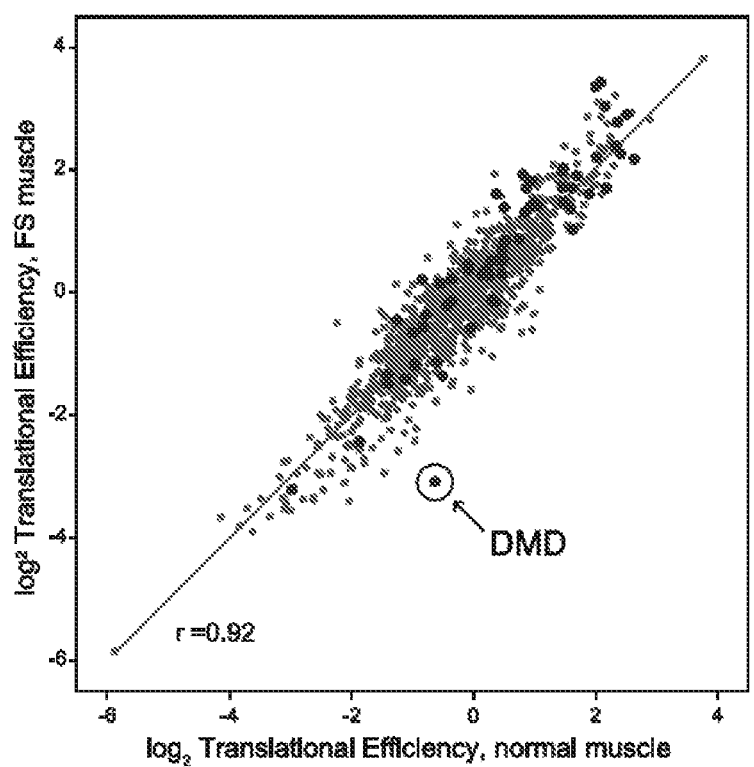
Figure 8A:
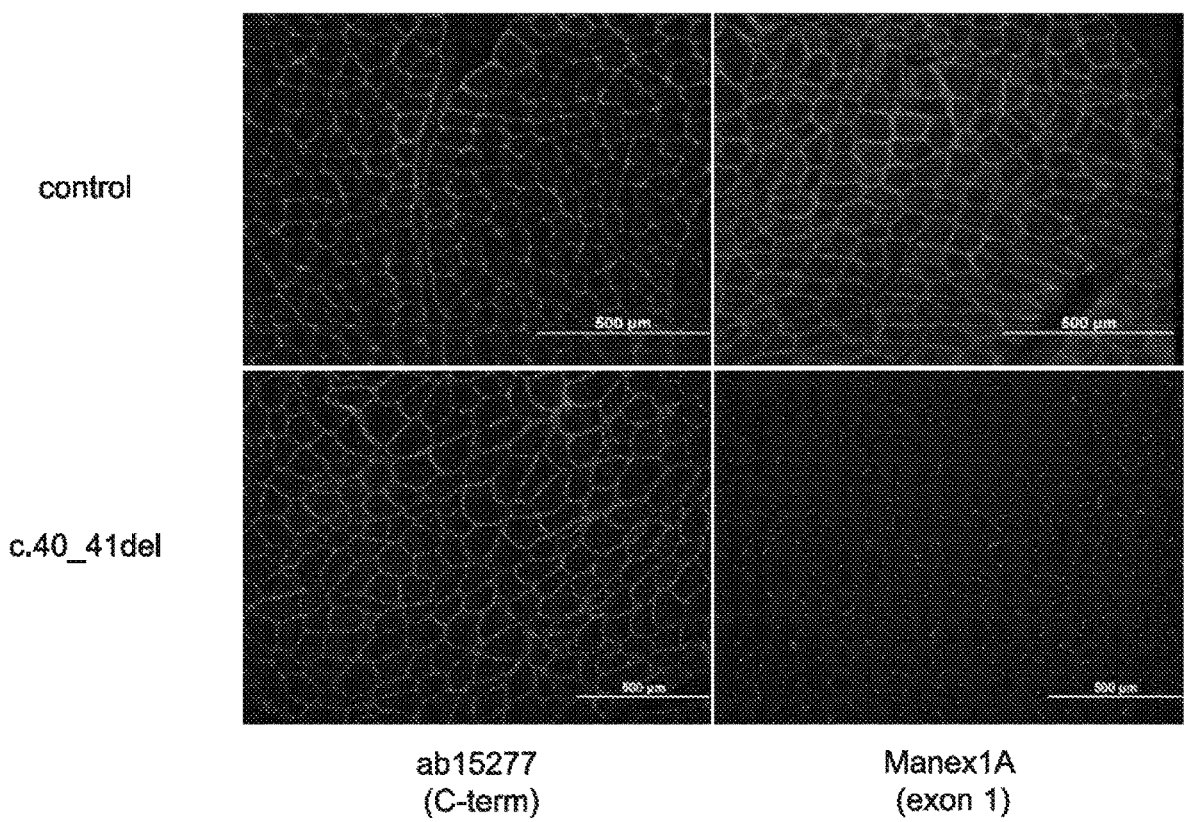
FIG. 8. Immunofluorescent analysis of muscle from the frameshift (c.40_41del) patient. (a) Immunostaining using a dystrophin antibody (Abcam 15277, C-terminal) shows dystrophin at the sarcolemmal membrane in both control and patient muscle biopsies whereas Manex1A staining is absent in the patient sample, confirming the lack of expression of the epitope encoded by exon 1. (b) Ribosome Profiling of the DMD muscle-isoform transcript. The normalized average reads (read depth per nt. versus the average read depth on NM_004006) for RNA-Seq reads are plotted every 25 nucleotides using an averaged normalized average read depth per nucleotide calculated from a 500 bp. sliding window. Reads from patient FS(c.40_41del) are shown in red and from control muscle in grey, with regression lines shown for each set of averages. (c) as in (b) except using RPF-Seq reads, with the linear regression line calculated for the CDS region only. (d) The exon structure of the NM_004006 transcript is drawn to the same scale as the x-axis from (b) and (c). The arrow indicates the location of the alternate translation initiation sites in exon 6. Since the experiment used total RNA, the RNA-Seq reads mapping to NM_004006 are derived from both nascent and mature transcripts. The 5' to 3' gradient of RNA-Seq reads shown in (b) agrees with an original estimate from human skeletal muscle of the relative excess of 5' exons in nascent RNA due to the transit time (~16 hrs.) for RNA polymerase to transcribe across the ~2.2 Mb of chr. X region containing the 79 DMD exons of the muscle isoform. Regression analysis of the RPF-Seq reads does not indicate a 5' to 3' gradient, inferring that ribosomes are equally distributed across the length of the mature transcript.

In a complementary approach, we examined DMD translation efficiency, promoter usage, and alternate splicing using muscle RNA isolated from a mild BMD patient with an exon 2 frameshift mutation (c.40_41del [p.Glu14ArgfsX17], referred to as FS) whose western blot also revealed expression of the same smaller molecular weight dystrophin (~410 kDa) which lacked the N-terminal epitope (FIG. 1c; FIG. 8a). To confirm our western blot results, muscle homogenate from the same FS patient was used to construct RNA-Seq libraries for ribosome-protected fragments (i.e., ribosome footprints isolated after RNase digestion) and for total RNA. We compared the mRNA translation efficiency in normal versus patient muscle using the ratio of reads from ribosome-protected fragments (RPFs) to reads from RNA-Seq. Among the top 1000 most abundant muscle mRNAs, DMD displayed the greatest change in translation efficiency (FIG. 1d), indicating a ~5-fold reduction in the amount of ribosomes translating the DMD muscle transcript in the frameshifted patient FS. This decreased amount of translation is consistent with both the expected reduction in dystrophin level given the patient's mild BMD phenotype, and with the amount of dystrophin seen in p.Trp3X patients[4] and other 5' mutation alleles (FIG. 1c).

Figure 1E:
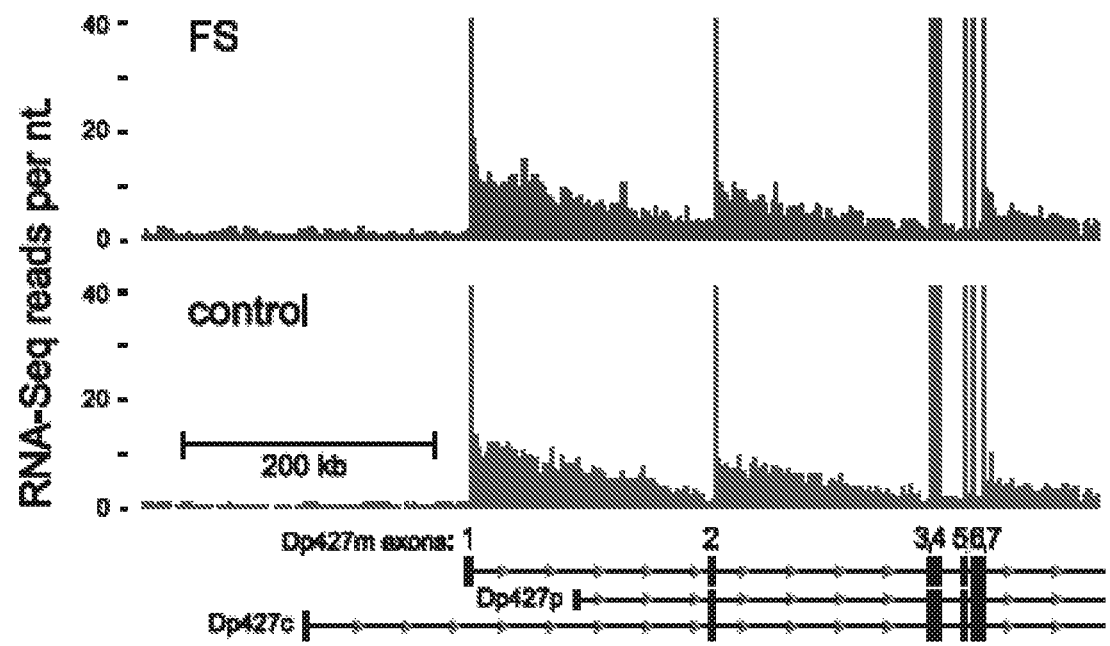
Figure 1F:
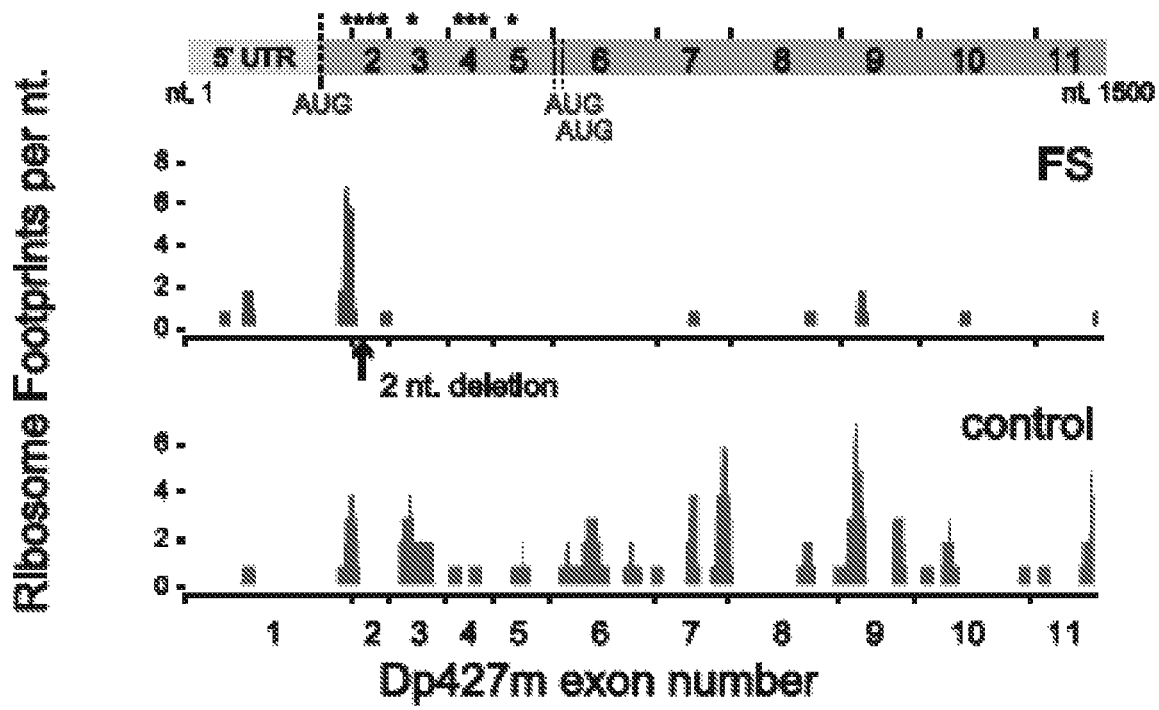
Figure 8B:
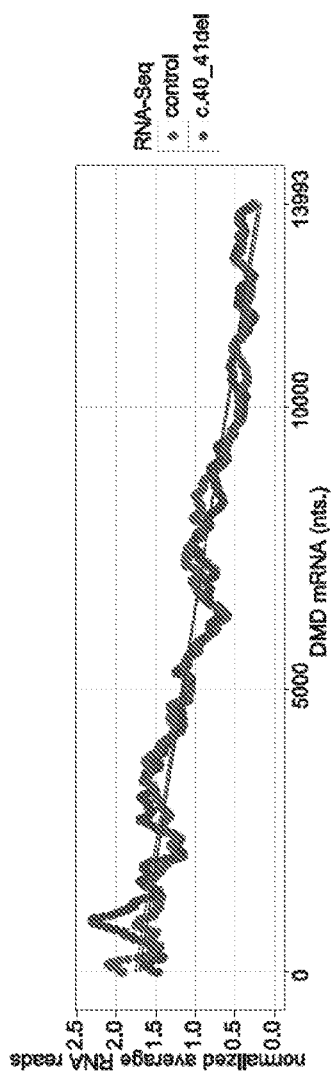
Figure 8C:
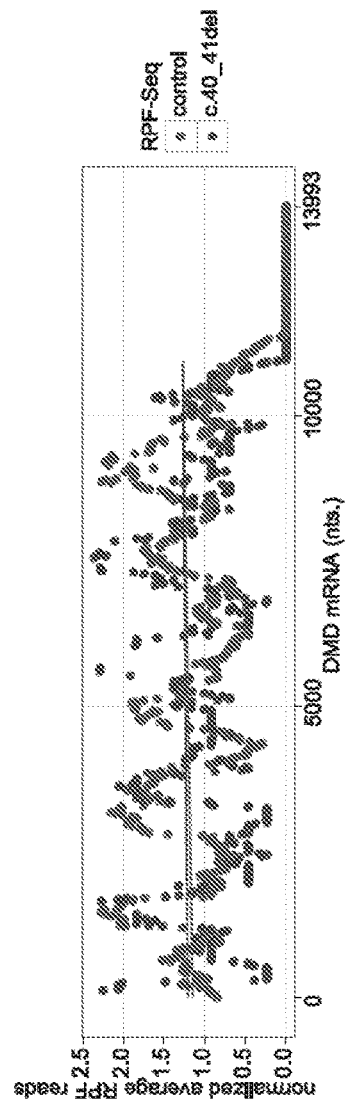
Figure 8D:
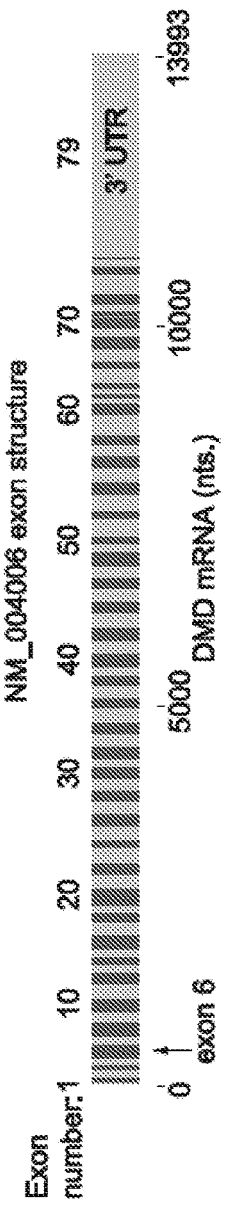

The saw-tooth RNA-Seq pattern observed in DMD introns 1 through 8 (FIG. 1e) confirmed that the major transcription start was located at the dystrophin muscle-specific promoter (Dp427m) and that DMD exons 1 through 7 underwent efficient co-transcriptional splicing [Ameur et al., Nature Structural & Molecular Biology, 18: 1435-1440 (2011)] in both the control and FS patient samples. Two alternate 427 kD isoforms of dystrophin (Dp427p and Dp427c) are expressed primarily in the central nervous system, and differ from Dp427m only in the use of alternate exon 1 sequences. The lack of a strong nascent RNA signal from either the Dp427p or Dp427c promoters confirmed that up-regulation of alternate promoters does not contribute to alternate AUG usage in exon 6 (FIG. 1e). In both samples, RNA-Seq reads spanning exon-exon junctions mapped exclusively to the known junctions between Dp427m exon 1 and exon 11, indicating that splicing of novel 5' UTRs from alternate promoters did not contribute to exon 6 AUG usage. The distribution of ribosome footprints mapped on Dp427m exons 1 through 11 revealed normal levels of exon 1 AUG initiation, followed by premature termination in exon 2 and resumption of translation following the exon 6 in-frame AUG codons (FIG. 1f) that continued into the body of the DMD transcript (FIGS. 8b, c and d), consistent with efficient alternate translation initiation.

Example 2

In Vitro Transcription/Translation Studies

Figure 2A:
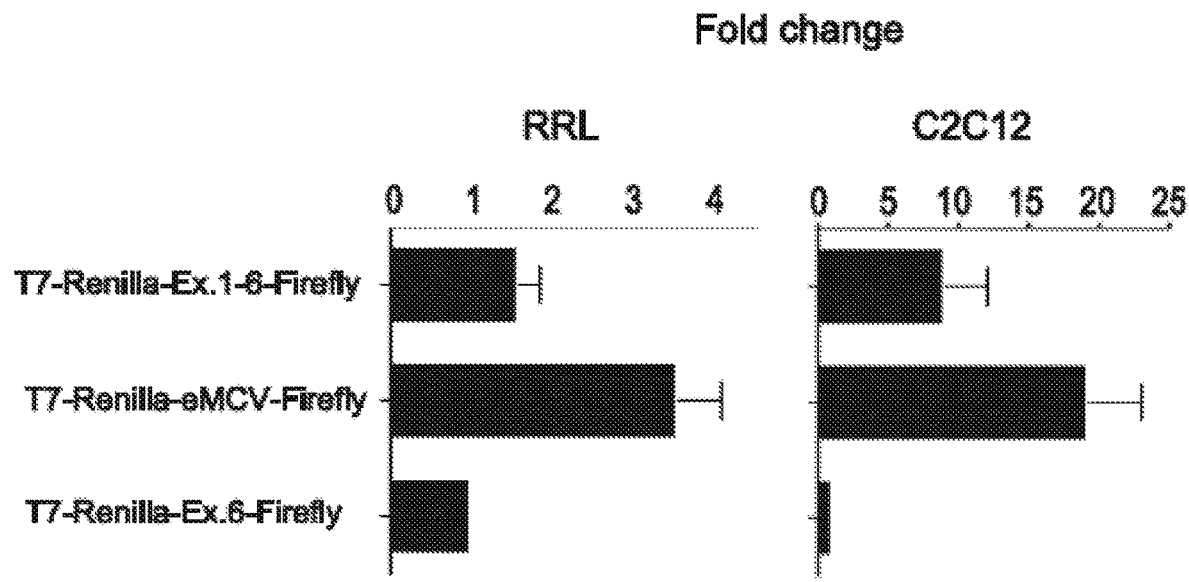
FIG. 2. Dystrophin exon 5 can induce cap-independent translation. (a) Induction of translation of the downstream (FLuc) cistron in an in vitro transcription/translation system (rabbit reticulocyte lysate [RRL], left) and following transfection into C2C12 cells (right) in a dicistronic dual luciferase reporter. Results are expressed as the ratio of Firefly: Renilla luciferase (F/L), and normalized to the empty vector (set as 1). (b) Formaldehyde electrophoresis of the T7 transcription products used in the RRL assay confirms RNA integrity. (c) Mapping of the exon 5 IRES: dicistronic mapping constructs (left) used to map cap-independent translation activity. In each case, numbering is based upon the Dp427m cDNA sequence; the full-length construct pRdEF+4+369 (exon 1 to 6) begins at the +4 position to exclude the native AUG initiation codon. Exon 6 was preserved, and AUG2 (M124) and AUG3 (M128) were cloned in-frame with the downstream FLuc reporter. FLuc luminescence (cap-independent) is expressed as a percentage of RLuc luminescence (cap-dependent) after transfection of the dicistronic constructs in C2C12 cells (right). All results were normalized to the exon 6 alone vector, the FLuc:RLuc ratio of which was set at a value of 1. Statistical analysis was performed using a Kruskal-Wallis test, comparing the results for each construct versus the exon 6 alone vector, which resulted in levels of expression comparable to an entirely empty vector (p>0.99). Significantly increased translation of the downstream reporter was demonstrated with the exon 1 to 6 (p<0.0001), exon 2 to 6 (p=0.0175), exon 3 to 6 (p=0.0009), exon 3* to 6 (p=0.0078), exon 4 to 6 (p=0.0078), or exon 5 to 6 (p=0.0019). In contrast, deletion of exon 5 (either in whole or in part) resulted in no significant difference for all three in comparison to exon 6 alone. (d) RT-PCR products amplified from RNA derived from transfected C2C12 cells, using primers located as depicted as arrows on the scheme in panel (c), shows no evidence of altered splicing. (e) Northern blot analysis of C2C12 transfected cells using a $P^{32}$ radiolabeled probe targeting the FLuc cistron shows no evidence of RNA strand breakage to explain the increased signal in the presence of dystrophin exons 1-5. (A non-specific band of approximately 3 kb is detected in every transfection condition, including the empty vector, and is therefore unrelated to the increase in FLuc or EMCV signals compared to empty vector. (f) IRES activity is abrogated by the presence of a duplicated exon 2, but not by a deletion of exon 2. Error bars represent s.d.
Figure 2B:
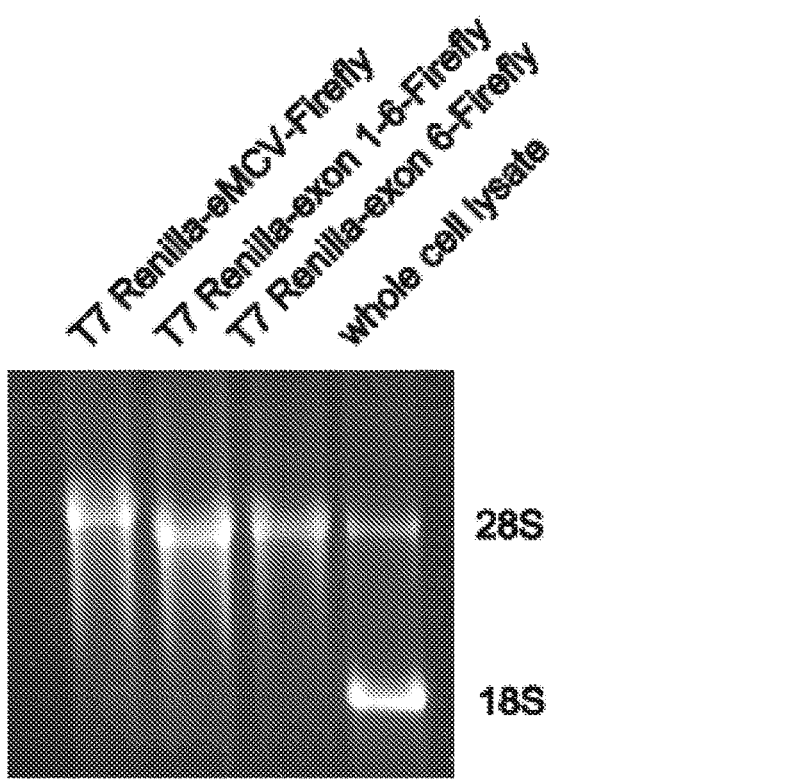
Figure 2C:
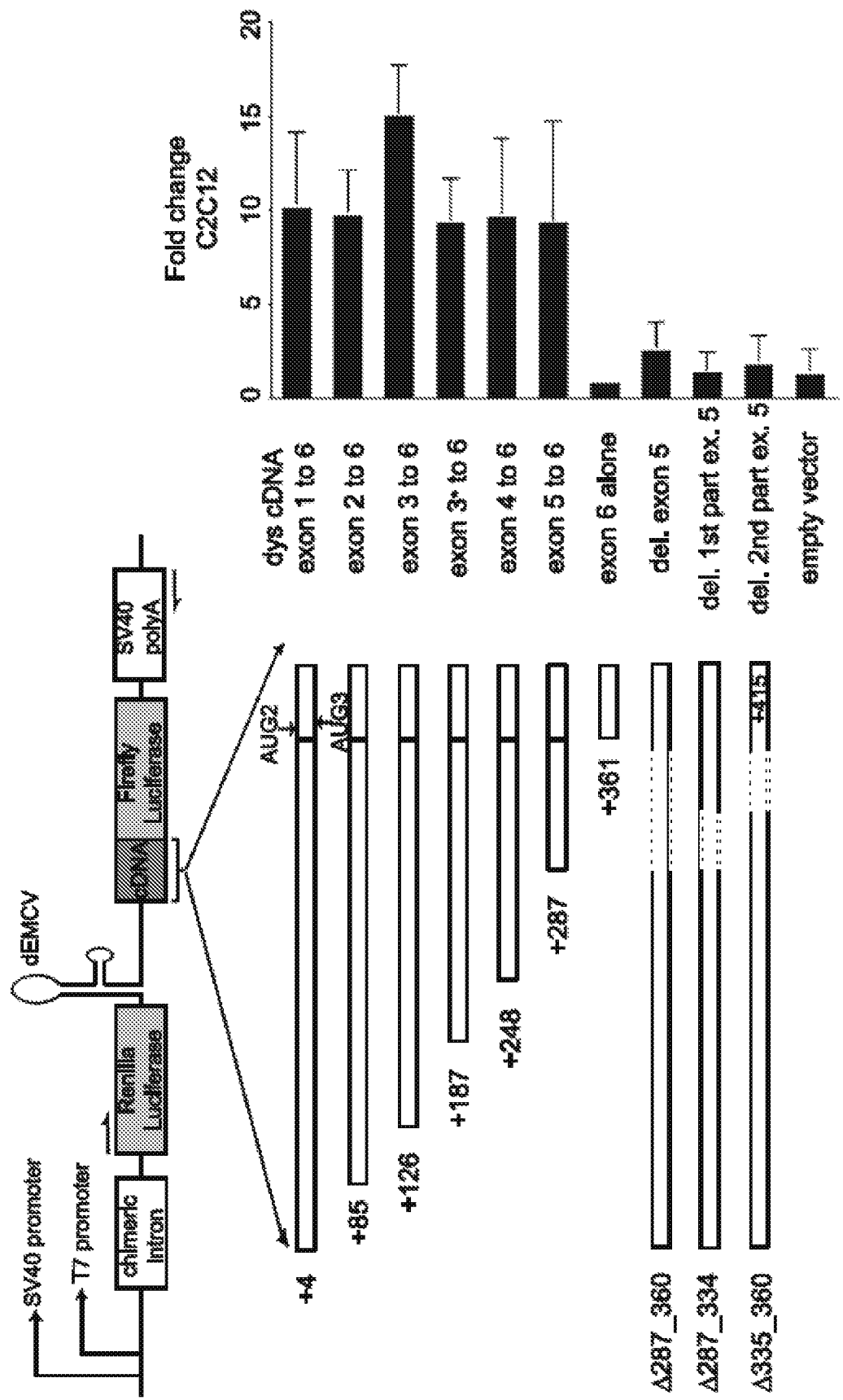

Having demonstrated new evidence for efficient alternate translation initiation using both ribosome profiling and protein analysis directly in patient muscle, we sought to characterize the elements contributing to the high translation efficiency. To determine whether exons 1 through 5 of DMD contain an IRES, we cloned the 5' portion of the cDNA encompassing exons 1 through part of exon 6, beginning at the +4 position to exclude the native AUG initiation codon (c.4_c.369, referred as exon 1 to 6), into the dicistronic dual luciferase reporter vector pRDEF. This vector contains an upstream cap-dependent *renilla* luciferase (RLuc) open reading frame (ORF) under control of an SV40 promoter and a downstream cap-independent firefly luciferase (FLuc) ORF under the control of the sequences of interest, with the two ORFs separated by a secondary structure element (dEMCV) that prevents ribosomal scanning (FIG. 2c). We used the EMCV IRES sequence as a positive control, and normalized all values to the empty vector. In each case we included 49 nucleotides from exon 6 that placed the exon 6 AUGs in-frame with the downstream FLuc reporter. This sequence corresponds to the first 39 nt, inclusive of the two in-frame AUGs (M124 and M128), and 10 additional nucleotides used for cloning purposes. T7 mediated RNA were generated from the different constructs and were used to perform rabbit reticulocyte lysate (RRL) translation assays (FIG. 2a, left panel). Size and integrity of the corresponding RNAs were checked using a formaldehyde agarose gel (FIG. 2b). Cap-independent translation activity (represented as the ratio of downstream FLuc to the RLuc luminescence) of the exons 1-5 of DMD results in a 1.5-1.7 fold increase in FLuc signal, less than the 3.4-3.8 increase seen with the control EMCV IRES but consistent with IRES activity (FIG. 2a, left panel).

Example 3

IRES Activity in Cell Cultures

Figure 9A:
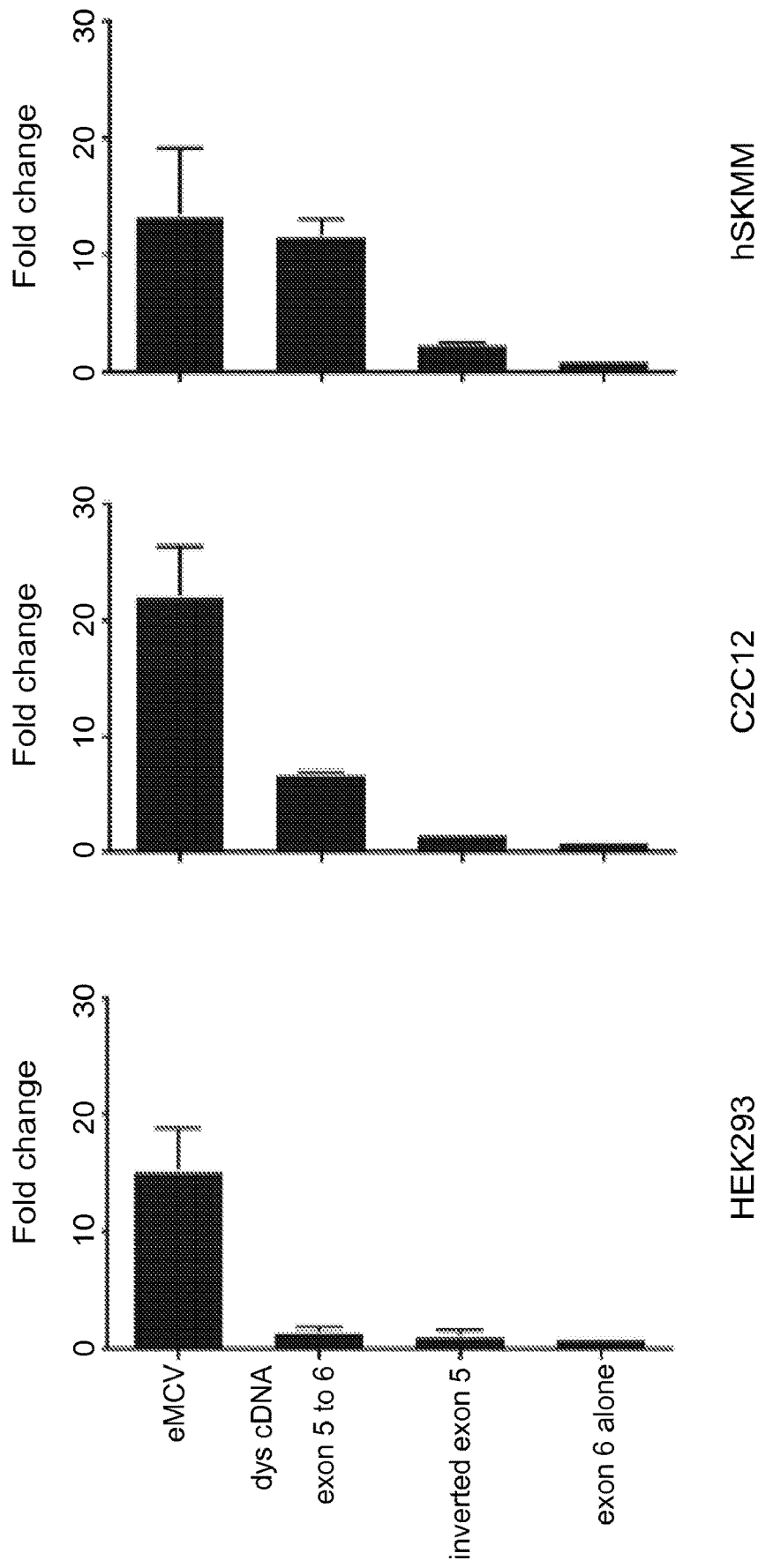
FIG. 9. The dystrophin IRES is not ubiquitously active. (a) Dual luciferase assays demonstrate activation in two myogenic cell lines (C2C12, and a commercial human skeletal muscle myoblast line [hSKMM]), but not in HEK209K cells, suggesting preferential activation in cells of a myogenic lineage. (b) Northern blot from transfected C2C12 and 293k using a probe against Firefly luciferase demonstrates the presence of the transcript as well as the previously described (FIG. 2) nonspecific band. Notably, this band is present in all conditions, including following transfection with the exon 6 alone construct, and therefore is unrelated to the fold change seen with exon 5 containing constructs. (c) RT-PCR products amplified from RNA derived from transfected 293k cells shows no evidence of altered splicing. Error bars represent s.d.

RRL-based translation may underestimate IRES activity of either viral or eukaryotic cellular IRESs, possibly due to the limiting amounts of RNA binding proteins in this specialized extract or due to the lack of tissue-specific IRES trans-acting factors (ITAFs). Therefore, the assay was performed in C2C12 myoblasts which express dystrophin, and we observed that the presence of the exon 1 to 6 construct leads to ~8 fold higher FLuc expression relative to exon 6 alone vector (FIG. 2a, right panel). This represents ~50% of the activity of the control EMCV IRES, suggesting the presence of a relatively strong IRES within exons 1-5. To map the position of the IRES, deletion constructs consisting of the 5' portion of the DMD gene (exons 1-5) or appropriate controls were cloned into pRDEF (FIG. 2c). Deletion of the first 300 nucleotides (nt) of this sequence did not significantly change the FLuc expression, whereas removal or inversion of the last 71 nt (representing nearly all of exon 5) completely abrogates expression of the FLuc reporter, and further deletions within exon 5 result in greatly reduced FLuc expression. To test the hypothesis that the putative IRES required muscle specific factors, we repeated the experiments in HEK293K cells, which do not endogenously express dystrophin, and in a commercial human myoblast cell line (hSKMM). Unlike the ECMV IRES, the putative DMD IRES did not stimulate FLuc expression in 293K cells whereas the level of stimulation in hSKMM cells replicated the C2C12 results (FIG. 9a), suggesting that the IRES is preferentially active in muscle.

Figure 2D:
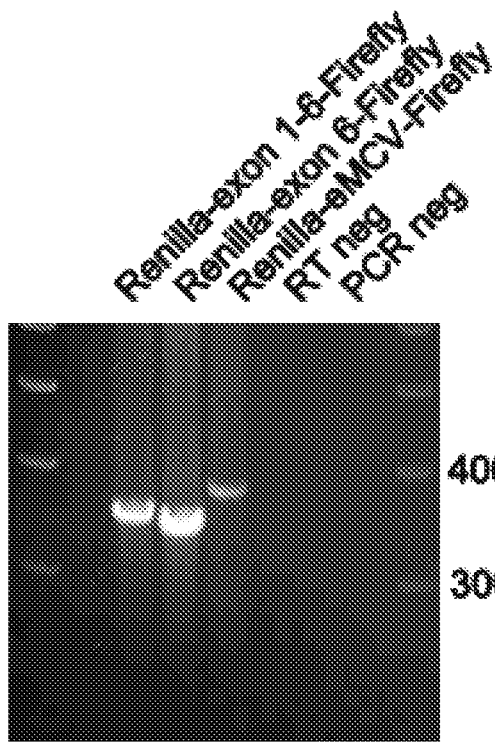
Figure 2E:
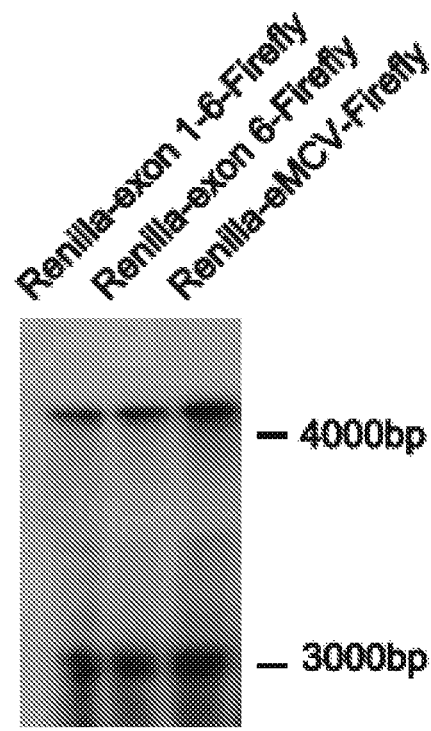
Figure 9B:
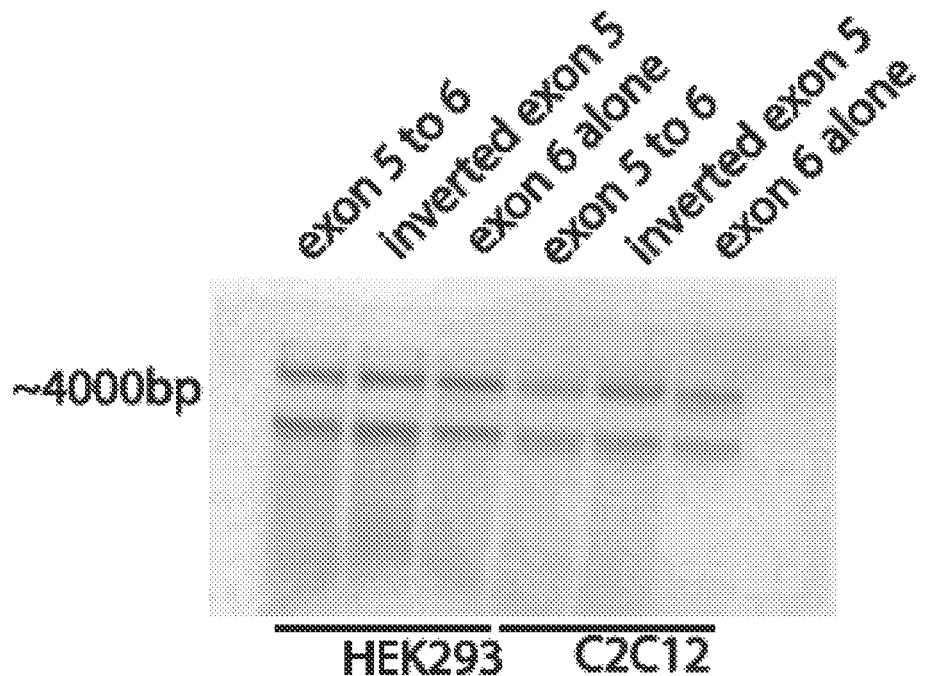
Figure 9C:
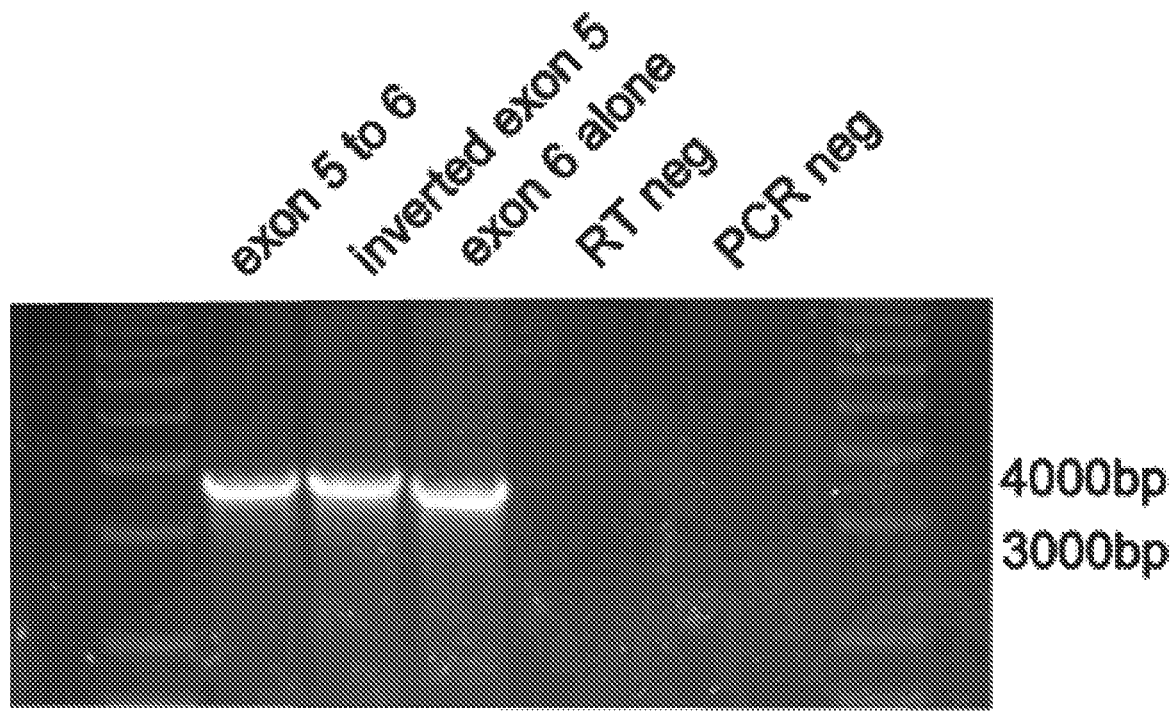

Control experiments were performed to exclude the possibility of aberrant splicing events, cryptic promoter activities, or other potential artifacts leading to misinterpretation of the dicistronic assay. We removed the upstream SV40 promoter to generate a promoterless version of the pRDEF vector containing the exon 1 to 6 (c.4_c.369) DMD sequence. Transfection of this construct into C2C12 myoblasts showed only minimal background luminescence from both RLuc and FLuc, strongly arguing against any cryptic promoter activity in the DMD coding sequence (data not shown). No aberrant splicing was detected by RT-PCR (FIGS. 2d and 9c), and RNA integrity was confirmed by a northern blot (FIGS. 2e and 9b).

Figure 2F:
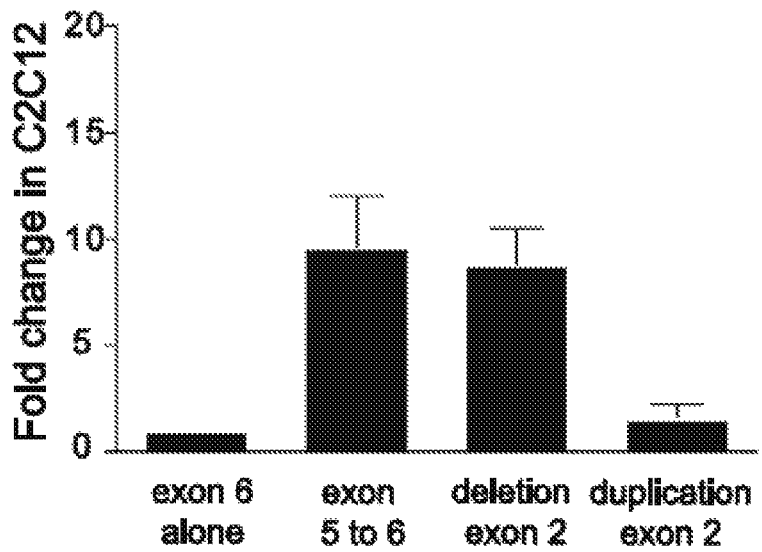

Notably, although either duplication or deletion of exon 2 results in an interrupted reading frame, the disparate associated clinical phenotypes led to the hypothesis that IRES activity may be diminished in the presence of an exon 2 duplication. We tested this hypothesis in C2C12 cells and showed that IRES activation was equivalent between the full length (exons 1-6) and deletion 2 cDNAs, but was markedly reduced in the presence of an exon 2 duplication (FIG. 2f) confirming that duplication but not deletion of exon 2 ablates IRES activity.

Example 4

Figure 3A:
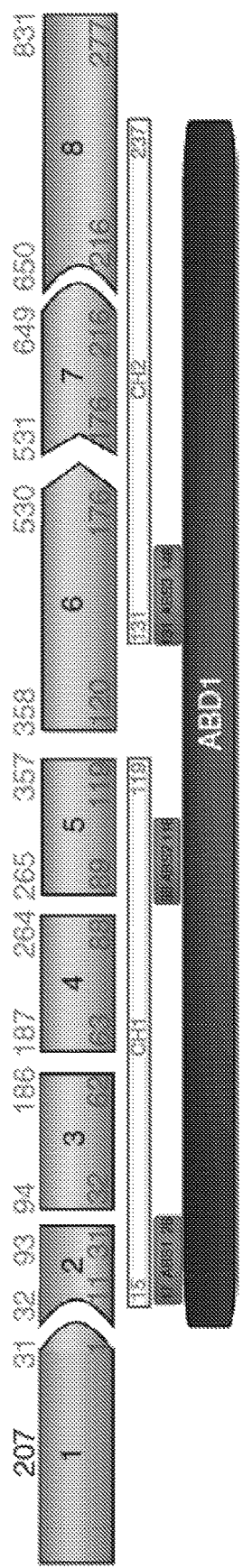
FIG. 3. Out-of-frame exon-skipping stimulates IRES activity in patient-derived cell lines. (a) Schematic representation of the human DMD exon 1-10 reading frame (blue) and 5'UTR (red). Blue numbers above each exon indicate cDNA positions; red numbers at the base of each exon indicate the amino acid position. The canonical actin binding domain 1 is represented, along with the predicted (via ScanProsite) CH and ABS domains. (b) Schematic representation of exon 2 (SEQ ID NO: 30). The selected targeted sequences are indicated below, affecting either splice acceptor (S.A.), splice donor (S.D.), or exon splice enhancer (E.S.E.) sequences (as predicted using Human Splicing Finder or ESE finder 3.0). (c) Two copies each of U7-C and U7-AL were cloned into the same AAV plasmid, as they were the most efficient in skipping exon 2 (see FIG. 10). The resulting construct is referred to as U7-ACCA. RT-PCR results after infection of U7-ACCA vector (1E11 vg) or H2A antisense oligonucleotide (AON H2A) into either wt or duplicated exon 2 FibroMyoD (FM) cells. These are derived from patient fibroblast lines stably infected with hTERT and a tet-inducible MyoD lentivirus; treatment with doxycycline results in transdifferentiation into a myogenic lineage, with subsequent dystrophin mRNA expression. (d) Immunoblot performed 14 days after infection of FM cells with U7-ACCA shows expression of the smaller N-truncated dystrophin protein (arrow). Antibody: C-terminal dystrophin (PA1-21011, Thermo, Inc.). A smaller band of approximately 390 kDa is detected in every lane, but is non-specific (as seen in the untreated sample) and does not correspond to the IRES-driven isoform. (The image was assembled for clarity; complete images are included as FIG. 11).
Figure 3B:
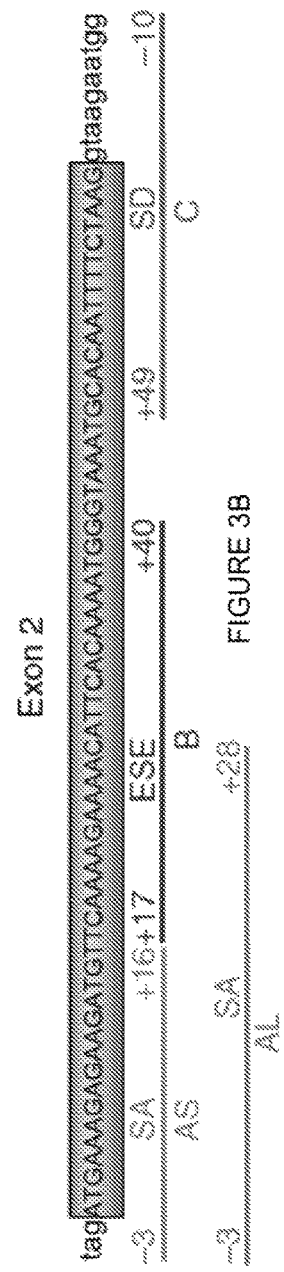
Figure 3C:
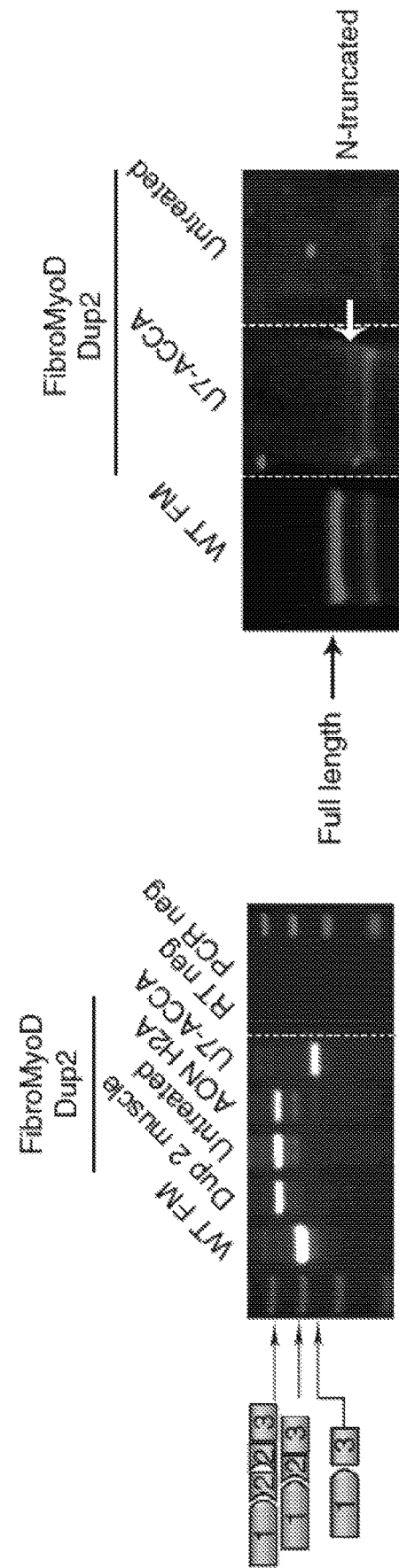
Figure 3D:
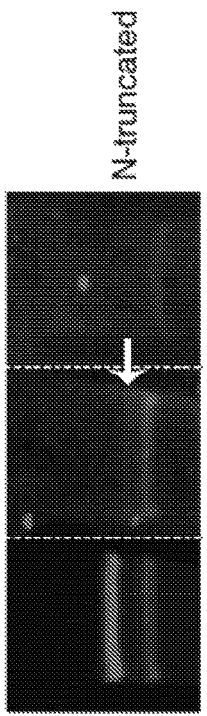
Figure 10A:
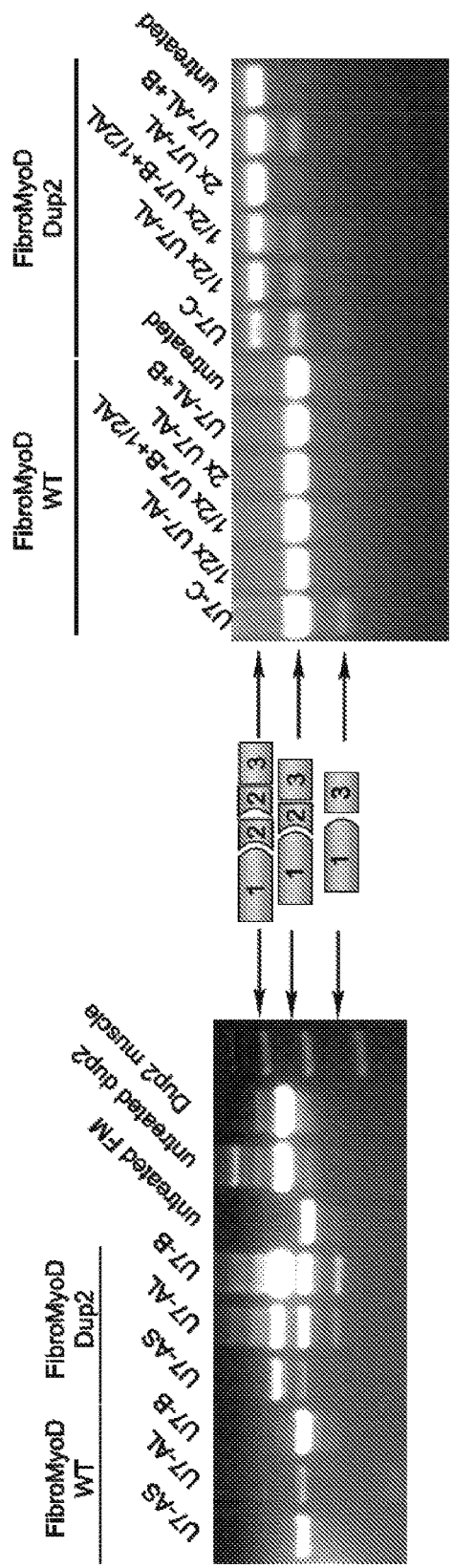
FIG. 10. Optimization of AAV mediated U7 exon-skipping. (a) Four different target sequences (AS, AL, B or C) were cloned into AAV under the control of U7. Infection of these AAV either alone (a) or in combination (b) were performed in both control and duplicated exon 2 patient derived-FibroMyoD. 3 days post AAV infection, RT-PCR results demonstrated that in U7-C is able to induce exon-skipping in both control and duplicated exon 2 patient FibroMyoD whereas U7-AL is only able to induce skipping in the patient cell lines. Two copies constructs U7-C and U7-AL were cloned into a same AAV plasmid (U7-ACCA). (c) Transfection of a Dup2 patient's cultured MyoD transformed fibroblasts and primary myoblasts, using an AON (AONH2A) which targets an internal exon 2 sequence, gave similar results, but at lower efficiency than U7-mediated skipping.
Figure 10B:
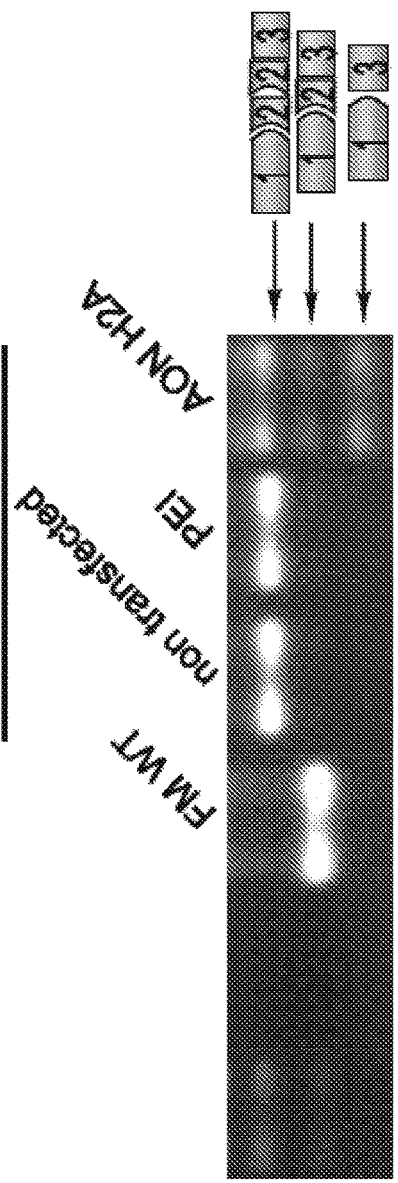
Figure 11A:
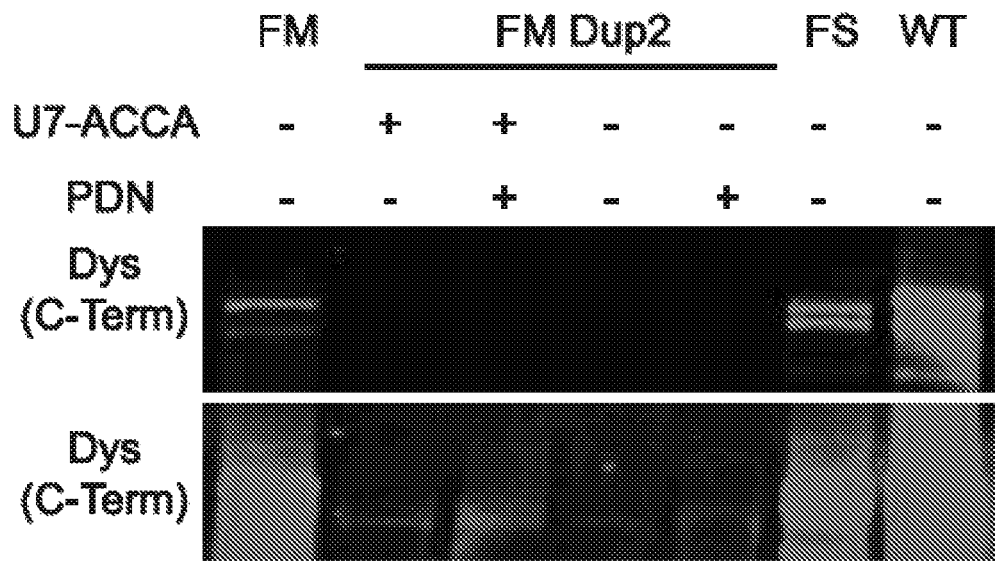
FIG. 11. Western blot from patient-derived cell lines. (a) The original western blot from FIG. 3d seen in two different imaging intensities, low (upper panel) and high (lower panel). Lane 1 from the upper panel and lanes 2 and 4 from the lower panel were used to assemble FIG. 3d. FM=FibroMyoD derived control cell lines; FM Dup2=FibroMyoD patient-derived cell lines from an exon 2 duplicated patient; FS=protein from muscle biopsy of c.40_41del. (b) Coomassie staining of the same samples as seen in FIG. 4c demonstrates no significant difference in migration behavior.
Figure 11B:
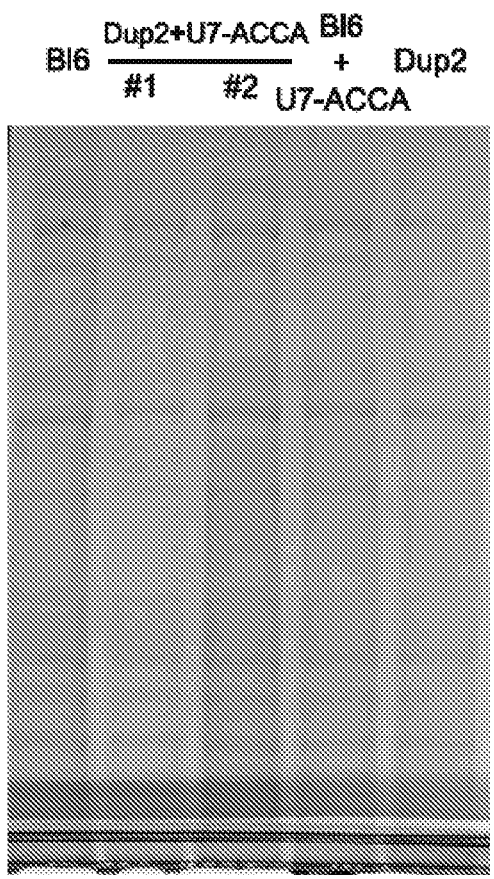
Figure 12A:
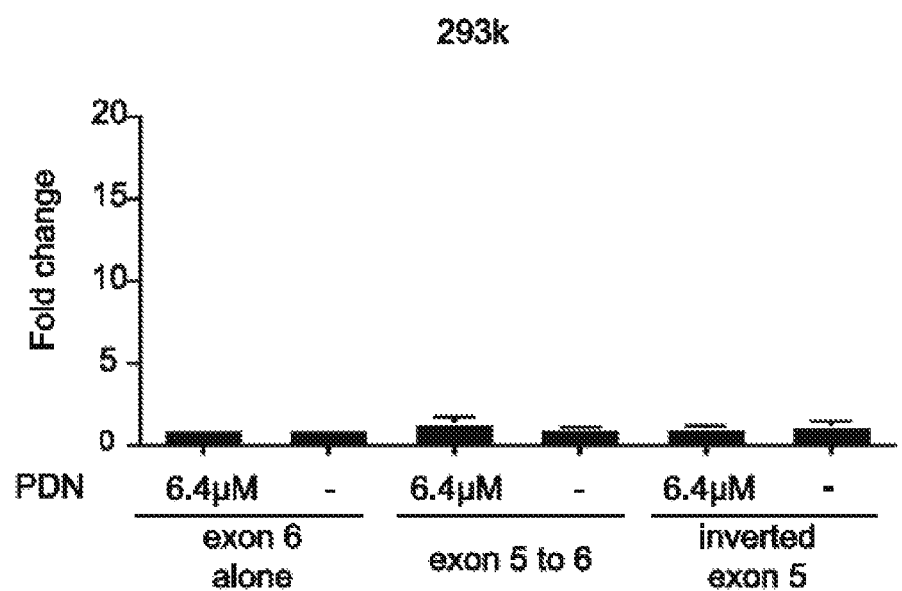
FIG. 12. Glucocorticoid increases IRES activity but cannot force its activation. (a) Dual luciferase assay results after transfection of 3 constructs in 293k treated with glucocorticoid demonstrate that IRES activity cannot be induced by this compound. Error bars represent s.d. (b) Genomic qPCR of AAV copy number confirm that increase of dystrophin level detected by western blot in PDN treated mice is not due an increased number of AAV vector in the PDN treated animals. N=4 animals per group. Error bars represent s.d.
Figure 12B:
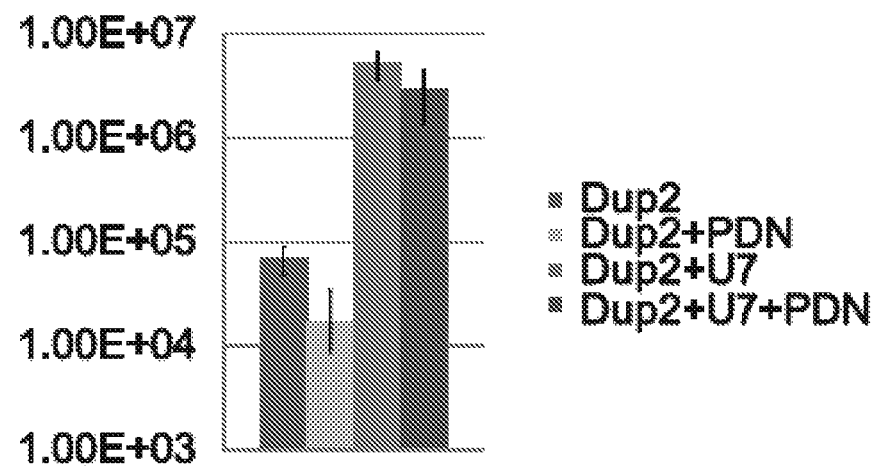
Figure 14:
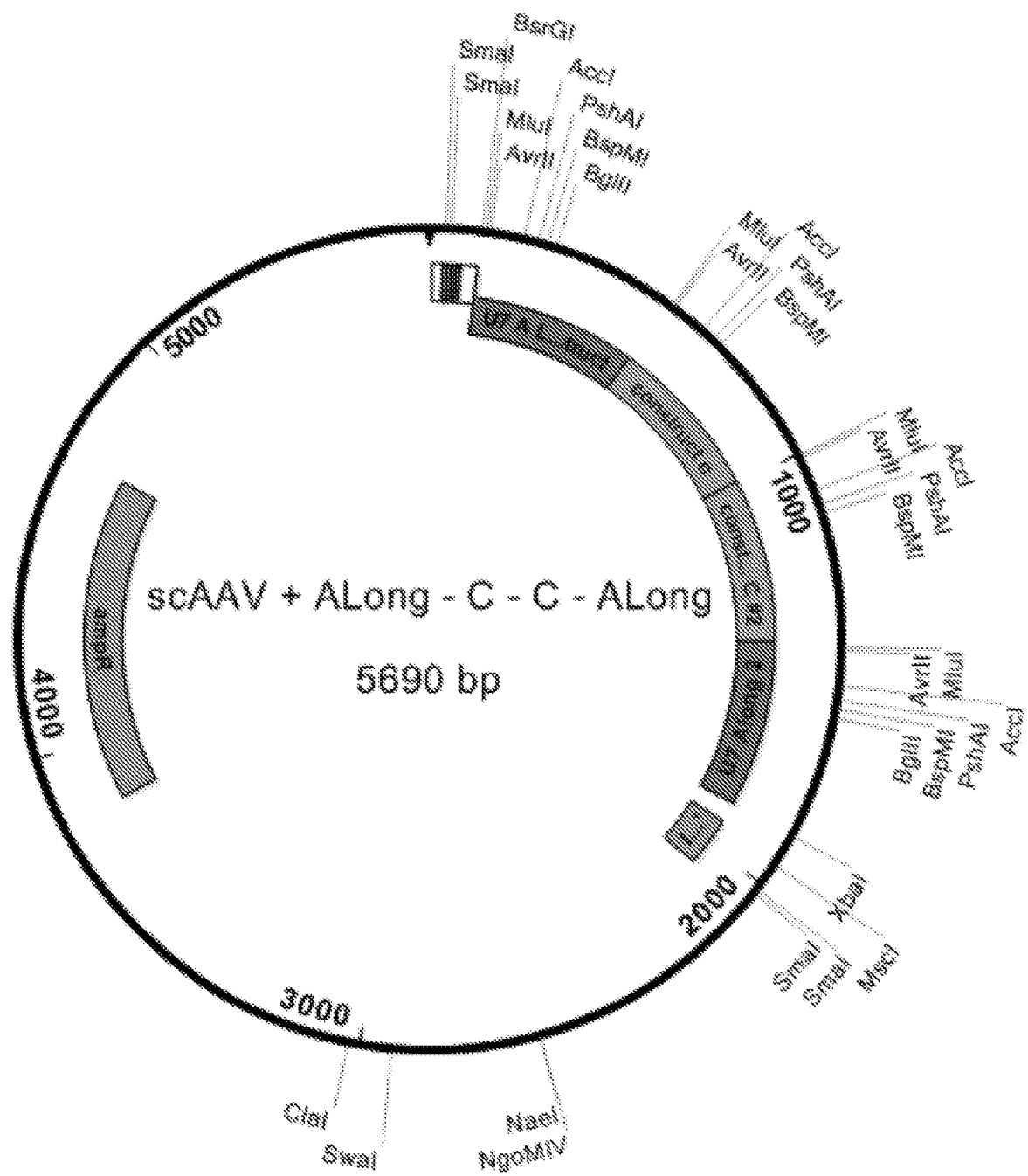
FIG. 14 shows a map of a plasmid with an AAV genome insert of an exemplary exon 2-targeted U7snRNA.
Figure 15B:
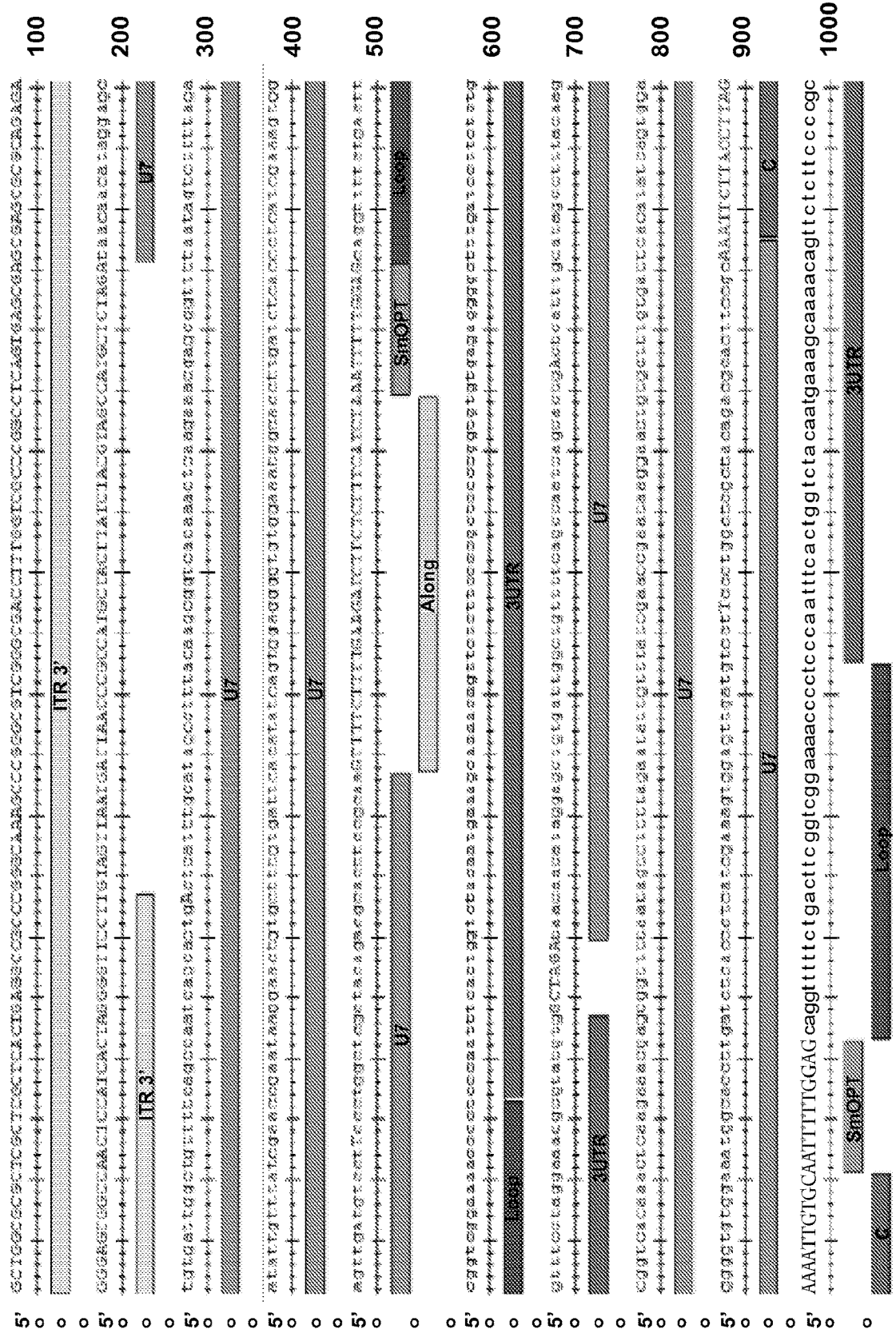
FIG. 15 (a) shows the AAV genome insert (3' to 5') (SEQ ID NO: 15 is the same sequence in the 5' to 3' direction) of the plasmid of FIG. 14.
Figure 15B:
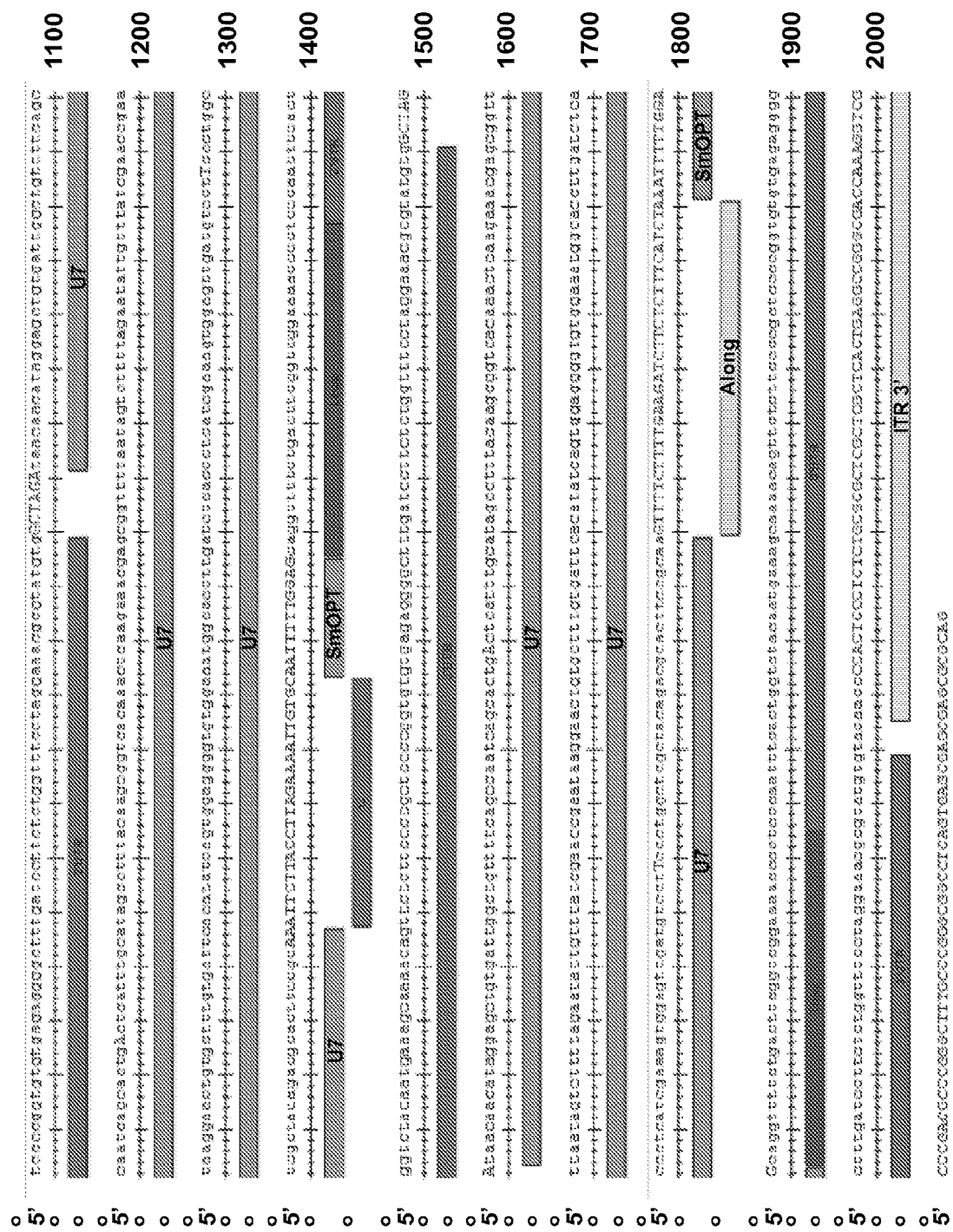

Out-of-Frame Exon-Skipping is Able to Drive an IRES Mediated Dystrophin In Vitro In considering skipping of exons prior to the exon 5 IRES, only the removal of exon 2 will disrupt the reading frame and result in a premature stop codon (FIG. 3a). We contemplated that deletion of this exon could be used therapeutically to increase activation of the IRES, whether by use of antisense oligonucleotides (AONs) [Wood et al., *Brain: A Journal of Neurology*, 133: 957-972 (2010); van Deutekom et al., *New England Journal of Medicine*, 357: 2677-2686 (2007) and Kinali et al., *Lancet Neurology*, 8: 918-928 (2009)] or by use of AAV-U7 mediated antisense delivery [Goyenvalle et al., *Science*, 306: 1796-1799 (2004) and Vulin et al., *Molecular Therapy: Journal of the American Society of Gene Therapy*, 20: 2120-2133 (2012)]. We selected four different sequences (respectively labeled "B", "AL", "AS" and "C" in FIG. 3b) for U7snRNA targeting and cloned each into AAV1 to assess exon-skipping efficiency in myoblasts generated from either a wild type or an exon 2 duplication fibroblast cell lines that expresses a doxycycline-inducible MyoD (referred as FibroMyoD) [Chaouch et al., *Human Gene Therapy*, 20: 784-790 (2009)]. All constructs were able to skip either one or two copies of exon 2 (FIG. 10). Subsequently, in order to increase skipping efficiency, two copies of each of the U7-C and U7-AL targeting antisense sequences were cloned into the single self-complementary (sc) AAV1 vector (and designated AAV1.U7-ACCA), the genome of which is shown in FIG. 15 in the 3' to 5' orientation. U7-C and U7-AL were used to avoid any possible overlap in the antisense sequence between AL and B. A known antisense sequence (AON H2A) was used as a positive control of skipping [Tennyson and Worton, *Nucleic Acids Res.*, 24: 3059-3064 (1996)]. Infection of FibroMyoD cells resulted in 88.6% of the DMD transcript with complete skipping of exon 2 leading to the production of N-terminally truncated dystrophin (FIGS. 3c, 3d and 12a).

Example 5

IRES Driven N-Truncated Dystrophin is Expressed after Out-of-Frame Exon-Skipping in a Novel Mouse Model Harboring a Duplication of Exon 2

Figure 4A:
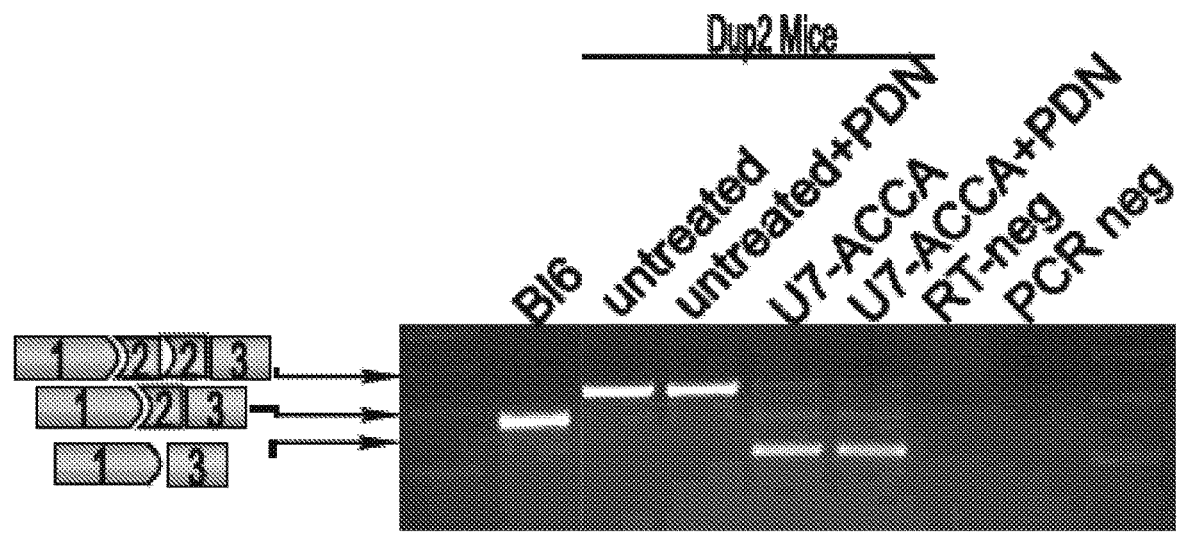
FIG. 4. Intramuscular delivery of U7-ACCA results in significant N-truncated dystrophin expression in Dup2 mice, restoring localization of dystrophin-associated proteins. (a, b) RT-PCR results performed 4 weeks after TA intramuscular injection of 1e11vg U7-ACCA show nearly complete skipping of both copies of exon 2 in both (a) Dup2 and (b) control Bl6 mice (PDN: methylprednisolone 1 mg/kg/day intraperitoneal). In Dup2 animals (a), quantification revealed the Dup2 transcript to be 5.1% of total, whereas the wild type was 8.6% and the Del2 transcript was 86.3%. In wild type Bl6 animals (b), the wild type transcript was 14.2% and Del2 transcript was 85.8%. (c) RNA-Seq read depth using a tibialis anterior muscle total RNA library from Dup2 U7-ACCA treated (upper) and Dup2 untreated (lower) mice, mapped to the 5' region of the mouse Dmd gene (mm9, chrX:80,150,000-81,050,000). (d) Immunoblot performed a month after infection shows significant expression of the N-truncated isoform (asterisk) in both Dup2 and control Bl6 mice. The protein induced in Bl6 males injected with U7-ACCA is of the same size as that expressed in the Dup2 treated animals, confirming the size difference between this protein and the full-length isoform. (C-terminal antibody: PA1-21011, Thermo, Inc). Coomassie staining of the same samples demonstrates no difference in migration behavior. (e) Immunofluorescent staining of dystrophin (C-terminal antibody: PA1-21011, Thermo, Inc), β-dystroglycan (Beta-DG; MANDAG2); and neuronal nitric oxide synthetase (nNOS; sc-648; Santa Cruz). (f) Evans blue (EBD) protection assay in Dup2 mice one month after intramuscular injection with 1e11vg shows stabilization of muscle membranes. Evans blue uptake (red) is seen only in fibers without positive dystrophin expression (green, C-terminal antibody: PA1-21011, Thermo, Inc). (Dup2 mice used for these panel; n=5)
Figure 4B:
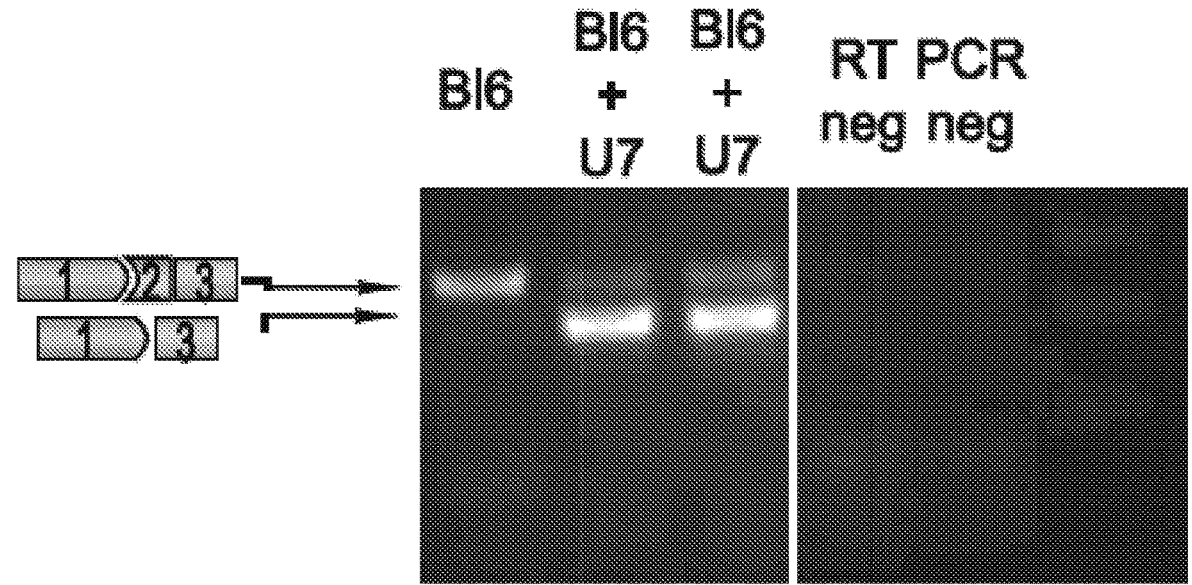
Figure 4C:
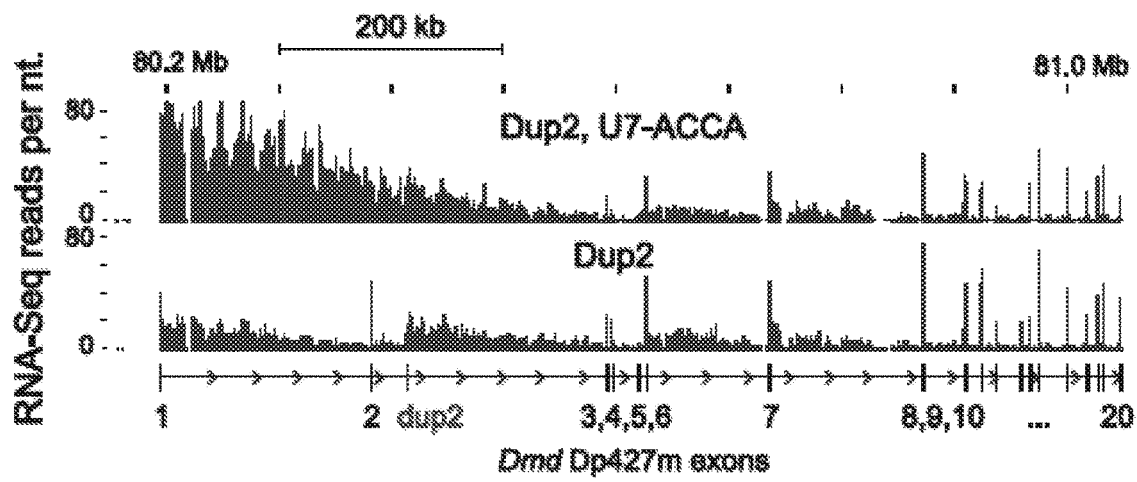
Figure 4D:
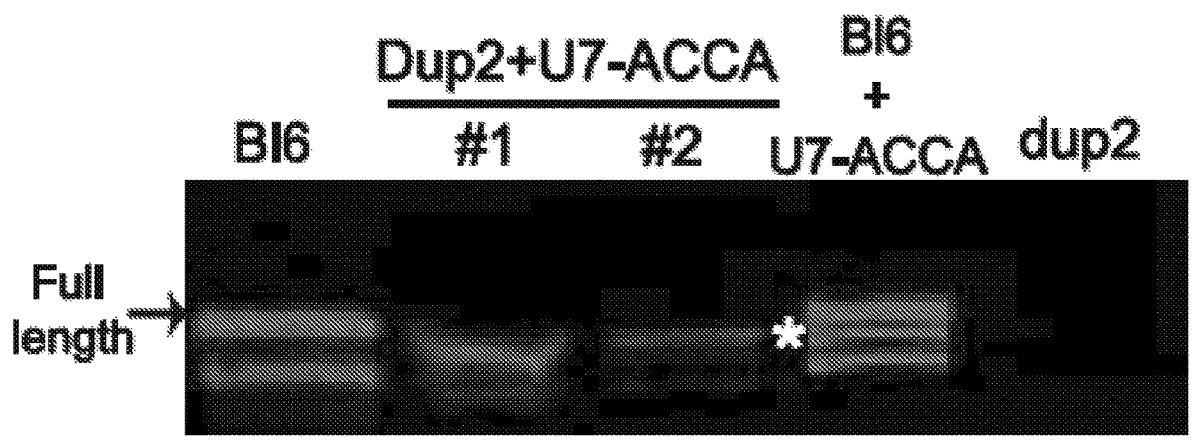
Figure 4E:
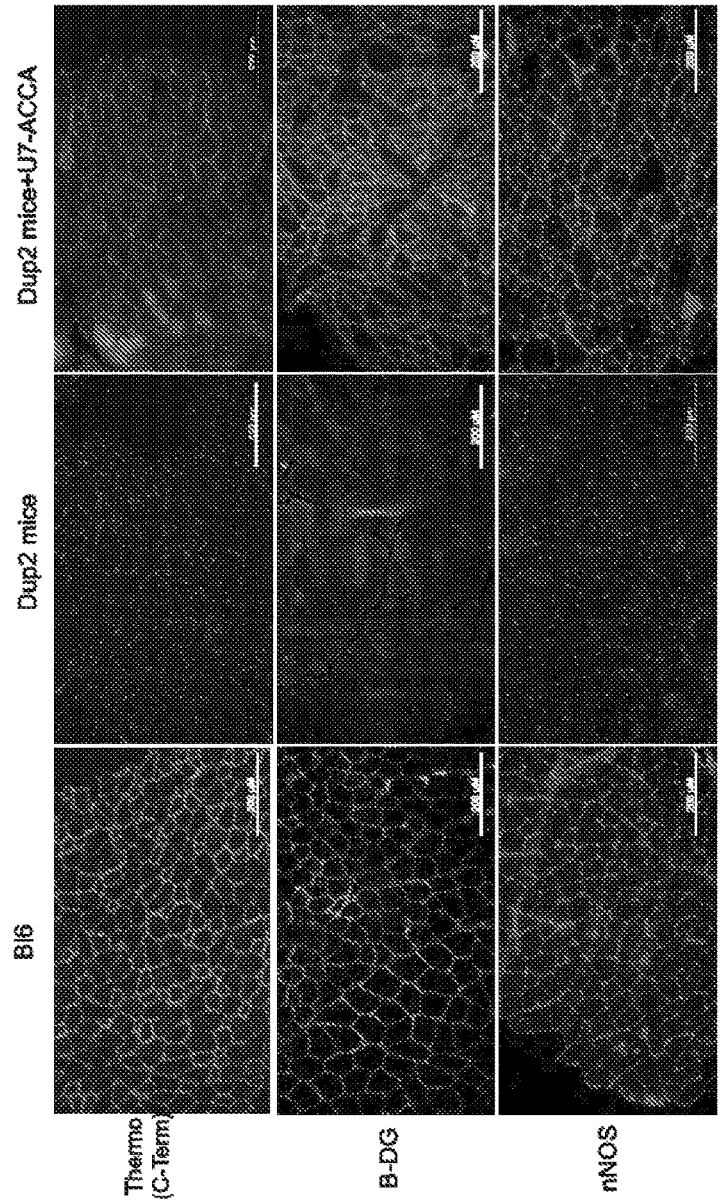

We tested the ability of the U7-ACCA vector to skip exon 2 in vivo in a mouse model carrying a duplication of exon 2 on a C57BL/6 background (the Dup2 mouse; described in Example 8 below). The resulting DMD mRNA contains two copies of exon 2, disrupting the reading frame and resulting in nearly complete absence of dystrophin expression. AAV1.U7-ACCA (1e11vg) was injected directly into the tibialis anterior muscle in six to eight week-old Dup2 mice (n=5) or Bl6 control mice. Four weeks later, RT-PCR analysis from injected muscles demonstrates nearly complete exon-skipping of exon 2 in Dup2 or Bl6 (FIG. 4a, 4b). Consistent with the RT-PCR results, the saw-tooth RNA-Seq pattern observed in Dmd introns 1 and 2 confirmed the suppression of co-transcriptional splicing of the duplicated exon 2 as well as the high-efficiency of co-transcriptional splicing of exon 1 to exon 3 in the treated mice (FIG. 4c). Western blot and immunostaining demonstrate expression of the N-truncated protein. Sarcolemmal staining is restored for β-dystroglycan and nNOS (FIG. 4d, 4e), suggesting the presence of a functional dystroglycan complex.

Figure 18D:
Figure 18E:
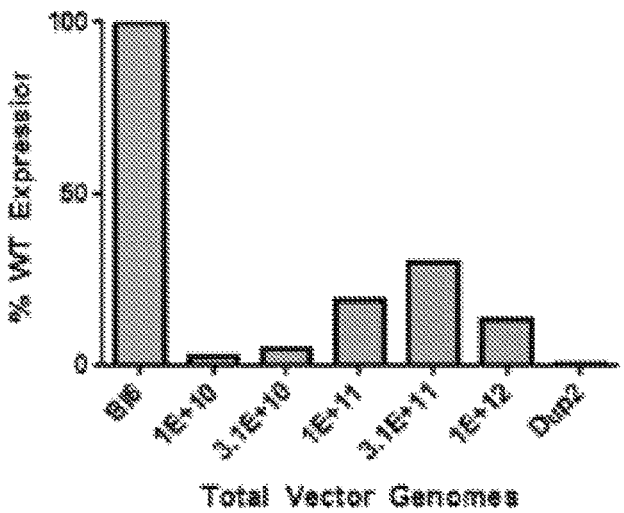
Figure 18F:
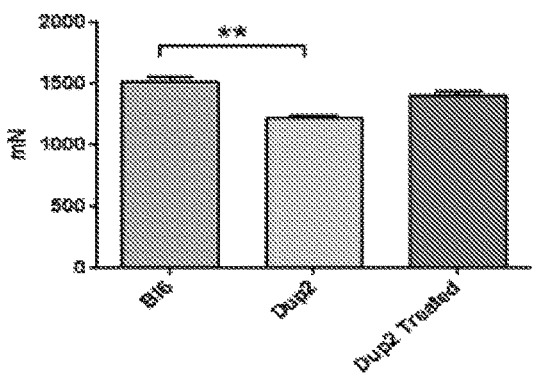
Figure 18G:
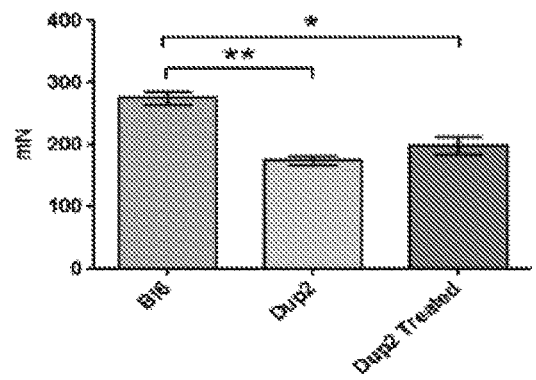

We also performed a dose escalation study using intramuscular injection (IM) into the tibialis anterior (TA) of Dup2 mice in order to assess the degree of dose response for exon skipping and protein expression. IM escalating doses are set out in FIG. 18a. As seen in FIG. 18b, the degree of skipped transcript shows an expected dose response. FIG. 18b shows a similar expected dose response in protein expression, maximal at 3.1E11 vg per injection, with significant correction of physiologic force defects (FIG. 18c).

Example 6

Glucocorticoid Increases Activation of the Dystrophin IRES

Figure 5A:
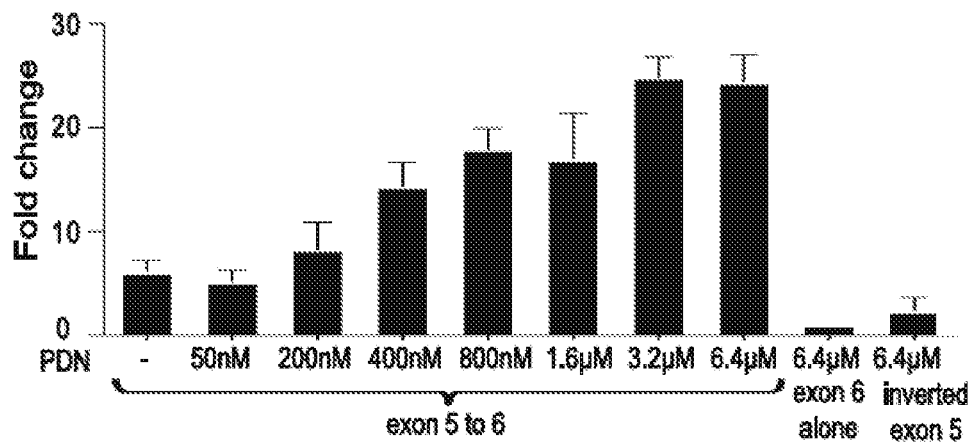
FIG. 5. Glucorticoid activation of the dystrophin IRES. (a) Dual luciferase assay performed on lysates from C2C12 cells transfected with the pRDEF vector carrying the exon 5-6 IRES construct. Methylprednisolone (PDN) increases IRES activity in a dose-dependent fashion. Error bars representate s.d. (b) Dup2 FM cells treated with both U7-ACCA and PDN (6.4 µM) show increased dystrophin expression. The image intensity for the wild-type lane was lowered to allow identification of bands. MHC=myosin heavy chain (loading control). (c) Representative immunoblot demonstrates increased expression of dystrophin in Dup2 mice injected with 1e11vg U7-ACCA after treatment with PDN (1 mg/kg/day). % Dys: intensity ratio of dystrophin:α-actinin, normalized to control muscle. (d) Quantification of the dystrophin/α-actinin signal in U7-ACCA treated muscles in the presence or absence of PDN. Five animals treated with U7-ACCA in the tibialis anterior muscles were injected with either PBS or PDN (1 mg/kg/day). Immunoblot was performed on each muscle in duplicate, and the signals for both dystrophin and α-actinin from the resulting 5 lanes were quantified using ImageJ. Significantly more dystrophin was present in muscles from PDN-treated animals (P=0.0159, two tailed Mann-Whitney test, error bars represent s.d.). (e) Representative western blot demonstrates an increased level of utrophin in Dup2 compared to Bl6 mouse. Treatment with PDN (1 mg/kg/day) does not increase expression of utrophin. (f) Quantification of the utrophin/α-actinin signal in treated muscles in the presence or absence of U7-ACCA and PDN. Five animals treated with U7-ACCA in the tibialis anterior muscles were injected with either PBS or PDN (1 mg/kg/day). The signals for both utrophin and α-actinin from the resulting 5 lanes were quantified using ImageJ. No significance was detected between the four (Kruskal-Wallis, error bars represent s.d.).
Figure 5B:
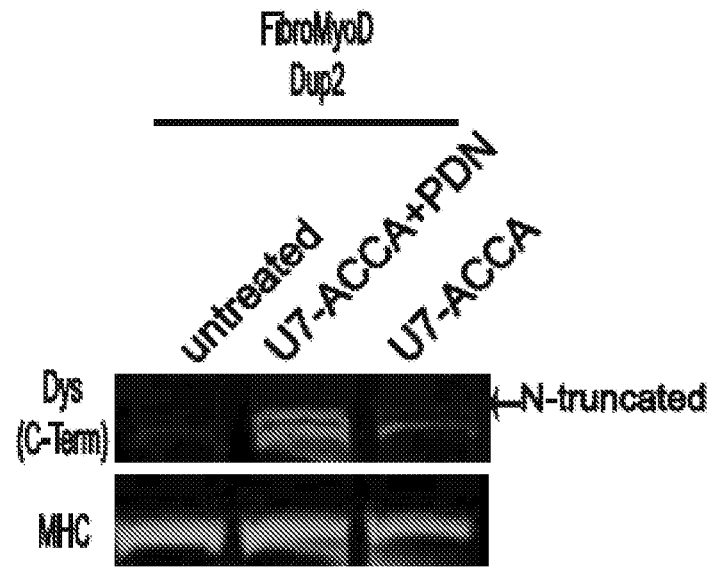
Figure 5C:
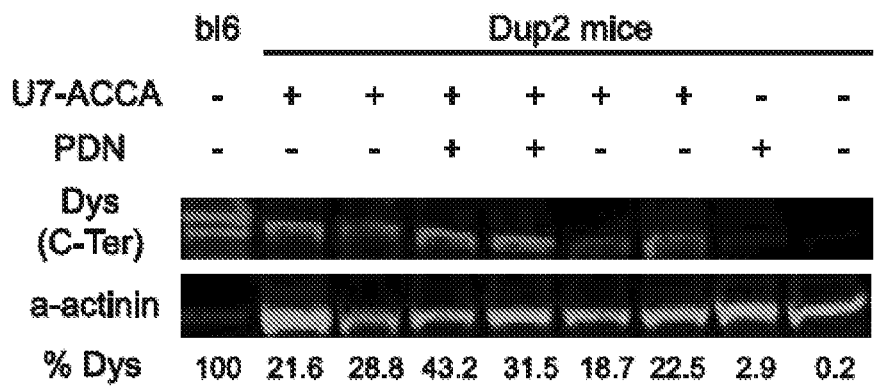
Figure 5D:
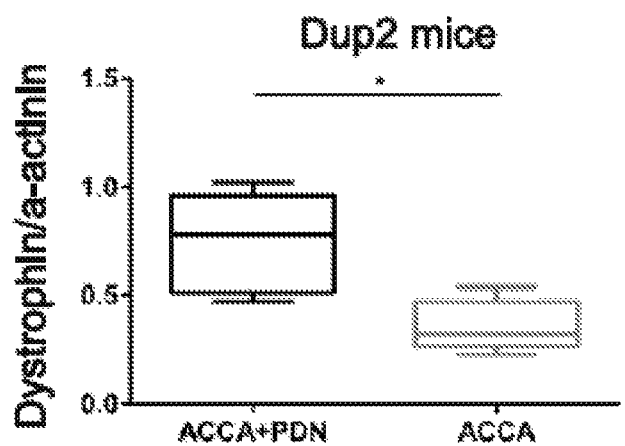
Figure 5E:
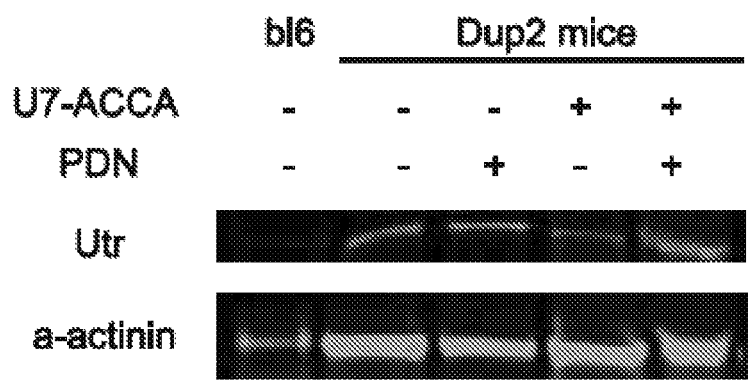
Figure 5F:
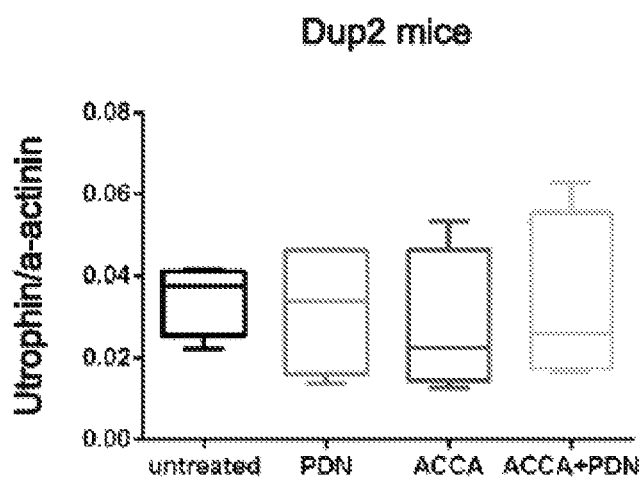

We examined the effect of glucocorticoid exposure on IRES activity as a muscle-specific IRES found in the 5' UTR of utrophin, an analog of dystrophin, was found to be glucocorticoid-activated [Miura et al., *PloS One*, 3: e2309 (2008)]. Furthermore, treatment with the glucocorticoids prednisone and deflazacort are standard treatment for DMD. We assayed exon 5 IRES activity using the exon 5 to 6 construct in C2C12 cells in the presence of increasing concentrations of 6-methyl-prednisolone (PDN) and found that downstream FLuc activity increased in a dose-dependent fashion from around 7 fold change in the absence of PDN to over 20 fold at 6.4 µM PDN (FIG. 5a). This glucocorticoid activation was not seen after transfection of the exon 6 alone or the inverted exon 5 control constructs or in 293K (FIGS. 5a and S5a). An increase in dystrophin expression was seen in Dup2 FibroMyoD cells treated with 6.4 µM PDN (FIG. 5b) and co-treatment of Dup2 mice (n=5) with both U7-ACCA and PDN resulted in an increase in dystrophin expression over U7-ACCA alone (FIG. 5c-d), consistent with glucocorticoid inducibility. An increase to less than 3% compared to untreated Dup2 was seen with PDN alone in rare samples (represented in FIG. 5c), suggesting some leakiness of the IRES in the Dup2 model. In all cases, this increase of dystrophin expression was not due to a difference in the AAV vector genome copy number (data not shown). Because utrophin translation may be regulated by corticosteroids and overexpression can compensate for absent dystrophin, we assessed utrophin levels in the same injected muscles (FIG. 5e). In untreated Dup2 animals, utrophin levels were increased in comparison to Bl6, similar to what has been reported in mdx, the standard dystrophinopathy mouse model. Comparison of the four groups reveals no statistically significant difference in utrophin levels between PDN treated and untreated animals (FIG. 5f), excluding utrophin upregulation as a cause of functional rescue following PDN treatment.

Example 7

Figure 4F:
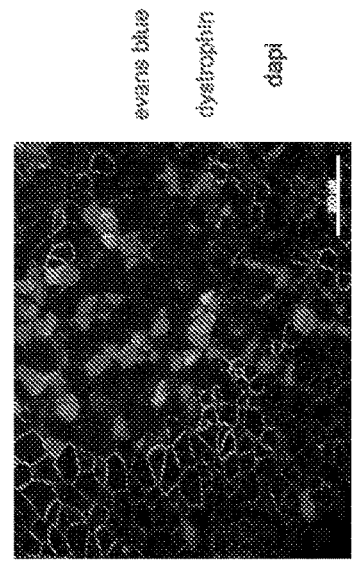
Figure 6A:
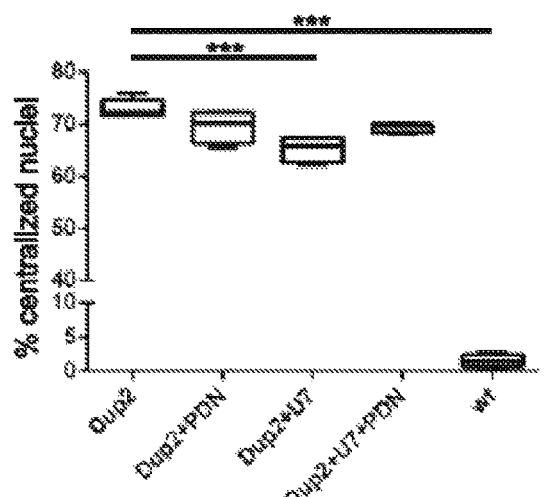
FIG. 6. Expression of the IRES-driven isoform improves muscle membrane integrity and protects Dup2 muscle from contraction-induced damage. Dup2 tibialis anterior muscles were treated by intramuscular injection of 5e11vg U7-ACCA alone or with methylprednisolone (PDN: 1 mg/kg/day intraperitoneal) and analyzed at 4 weeks post-injection. (a) Central nucleation in untreated Dup2 animals (73.0±1.6% of myofibers) was significantly reduced by treatment with U7-ACCA alone (65.2±2.2%, ***p=0.0002). No significant difference was observed between Dup2 and Dup2+PDN. (b) The percentage of Evans blue dye (EBD)-positive fibers in untreated Dup2 muscle (14.7±6.6%; one outlier is represented as a dot) is reduced by treatment with U7-ACCA alone (2.8±1.8%, *p=0.0310) or in combination with prednisone (0.65±0.5%, *p=0.0005). No significant difference was observed between Dup2 and Dup2+PDN. EBD-positive fibers were quantified as a percent out of a total of 5,000 fibers counted per animal. (c) Normalized maximum hindlimb (Norm max HL) grip strength in untreated Dup2 mice (2.22±0.26 kg force/kg mass of animal, or kgf/kg) is significantly lower than Bl6 (3.36±0.37 kgf/kg, *p<0.0001). Significantly improved strength follows treatment with either U7-ACCA alone (3.35±0.32 kgf/kg, * p<0.0001) or in combination with prednisone (3.17±0.28 kgf/kg, *p=0.0002), both of which restore strength to a level not significantly different from that seen in Bl6. No significant difference was observed between Dup2 and Dup2+PDN. (d) Normalized specific force following tetanic contraction in untreated Dup2 animals (170.9±14.3 mN/mm$^2$) is significantly less than in Bl6 (274.0±12.1 mN/mm$^2$,** p=0.0061). Significantly increased force follows treatment with U7-ACCA alone (236.04±19.4 mN/mm$^2$, *p=0.0350) or with prednisone (251.2±10.4 mN/mm$^2$, **p=0.0025), both of which restore specific force to a level not significantly different from that seen in Bl6. No significant difference was observed between Dup2 and Dup2+PDN. (e) Treatment significantly protects Dup2 muscle from loss of force following repetitive eccentric contractions. Two-way analysis of variance demonstrates significant improvement in decay curves versus untreated Dup2 (*p<0.05 and *** p<0.001), and Bonferroni post-hoc analysis demonstrates that the combination of both treatment showed no significant difference from control Bl6 in force retention following contractions #3 to #10 (*p<0.05 and ***p<0.001). No significant difference was observed between Dup2 and Dup2+PDN (p<0.99). Two way ANOVA demonstrates significant difference between Dup2+U7 and Dup2+U7+PDN (*p<0.05) (a, b, c) n=4 animals studied for each condition and when applied 2000 fibers count/mouse, two tailed Kruskal-Wallis, error bar as s.d.); (d,e) n=5 muscles from at least 3 animals, error bar as s.e.m.
Figure 6B:
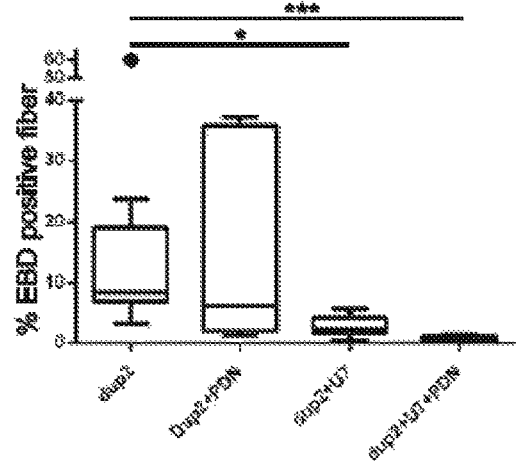
Figure 6C:
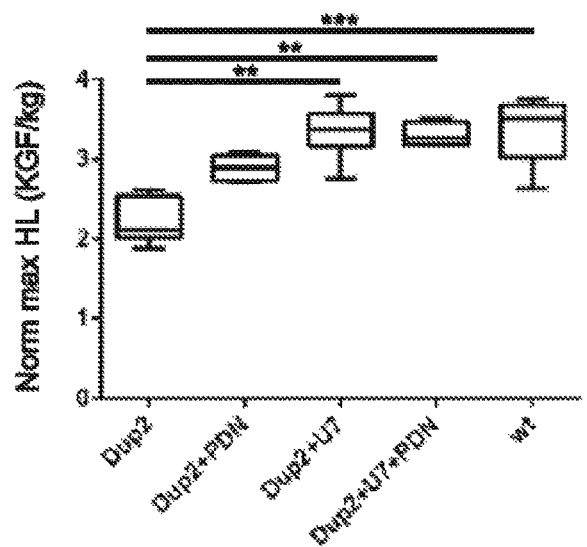
Figure 6D:
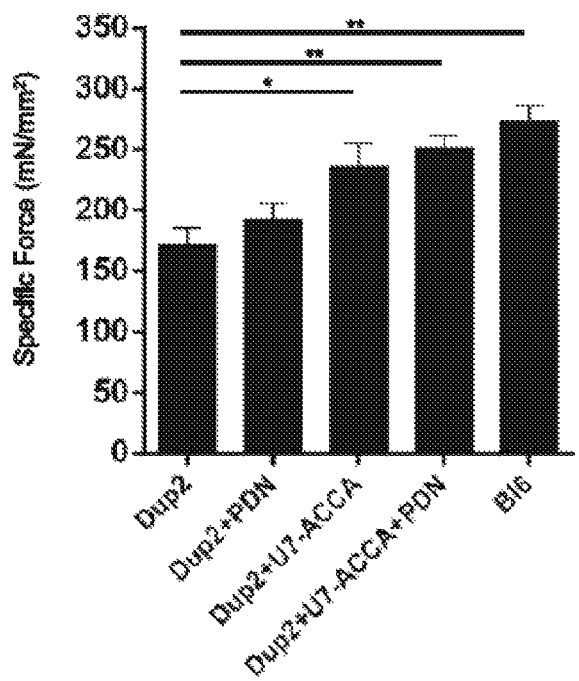
Figure 6E:
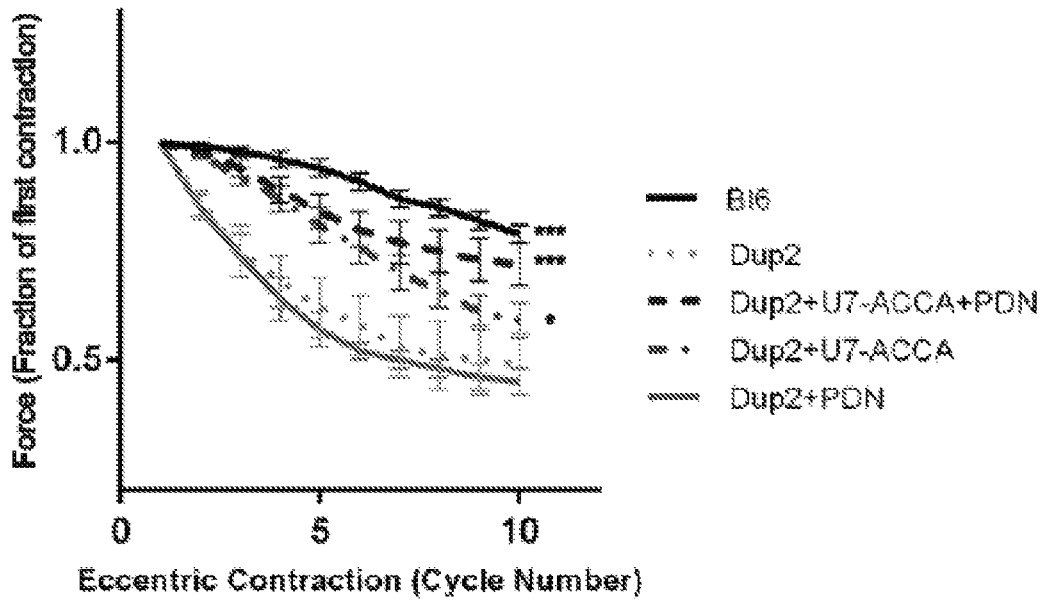

Local IRES Driven N-Truncated Dystrophin Expression Stabilizes Muscle Membrane and Corrects Force Deficits in Dup2 Mouse Muscle We examined whether expression of the IRES-driven isoform improved muscle integrity and physiology in the Dup2 mouse. Similar to the case in mdx mice, dystrophic changes in Dup2 mice are quantifiable at 4 weeks of age as widespread muscle regeneration characterized by centralized nuclei (Vulin et al., manuscript in press). One month after intramuscular injection of AAV1.U7-ACCA into the tibialis anterior muscle of 4-week old Dup2 mice, expression of the IRES driven isoform results in a significant reduction of centralized nuclei (FIG. 6a). To demonstrate that this isoform restores membrane integrity, treated and untreated Dup2 mice were subjected to a downhill running protocol and injected with Evans blue dye (EBD), which enters skeletal muscle fibers that have been permeabilized by membrane damage. Following intraperitoneal injection of EBD, uptake is found only in fibers without dystrophin staining, suggesting the N-truncated protein stabilizes the sarcolemma and provides further evidence for the functionality of this protein in vivo (FIG. 4f). Quantification of the number of EBD positive fiber confirms that expression of the IRES driven isoform results in protection of muscle fibers in these mice (FIG. 6b). Importantly, this membrane protection is associated with restoration of hindlimb grip strength (FIG. 6c) and muscle specific force (FIG. 6d) to the levels seen in Bl6 control mice. Dup2 muscles injected with U7-ACCA with or without prednisone were significantly more resistant to contraction-induced injury than untreated Dup2 muscle, and the combination of both treatments showed no significant difference from Bl6 controls (FIG. 6e), Despite the minimal (<3%) expression of dystrophin seen in some Dup2 muscles by PDN (FIG. 5c), treatment of the Dup2 muscles by PDN alone does not result in a significant amelioration of the muscle physiology (FIG. 6).

Example 8

DMD Models

Examples of models of the DMD exon 2 duplication include in vivo and in vitro models as follows.

Mdxdup$^2$ Mouse Model

Mice carrying a duplication of exon 2 within the DMD locus were developed. The exon 2 duplication mutation is the most common human duplication mutation and results in relatively severe DMD.

A map of the insertion vector is shown in Figure D. In the map, the numbers indicate the relative positions of cloning sites and exons and restriction sites. The neo cassette is in the same direction of the gene and the insertion point is precisely at 32207/32208 bp in the intron2. At least 150 bp extra intronic sequences are kept on each side of inserted exon 2, E2 region is 1775-2195 bp. Sizes of exon 2 and intron 2 are 62 bp and 209572 bp respectively.

Male C57BL/6 ES cells were transfected with the vector (Figure D) carrying an exon2 construct and then insertion was checked by PCR. One good clone was found, amplified and injected in dozens of albino BL/6 blastocysts. Injected blastocysts were implanted into recipient mice. The dystrophin gene from chimeric males was checked by PCR and then by RT-PCR. The colony was expanded and includes some female mice bred to homozygosity. Dystrophin expression in muscles from a 4 week old hemizygous mdxdup2 mouse was essentially absent.

Immortalized and Conditionally Inducible fibroMyoD Cell Lines

Expression of the MyoD gene in mammalian fibroblasts results in transdifferentiation of cells into the myogenic lineage. Such cells can be further differentiated into myotubes, and they express muscle genes, including the DMD gene.

Immortalized cell lines that conditionally express MyoD under the control of a tetracycline-inducible promoter were generated. This is achieved by stable transfection of the primary fibroblast lines of a lentivirus the tet-inducible MyoD and containing the human telomerase gene (TER). The resultant stable line allows MyoD expression to be initiated by treatment with doxycycline. Such cell lines were generated from patients with DMD who carry a duplication of exon 2.

Using the line, duplication skipping using 2'-O-methyl antisense oligomers (AONs) provided by Dr. Steve Wilton (Perth, Australia) was demonstrated. Multiple cell lines were tested.

Transiently MyoD-Transfected Primary Cell Lines

Proof-of-principle experiments using primary fibroblast lines transiently transfected with adenovirus-MyoD were conducted. The adenovirus constructs were not integrated in the cell genomes, yet MyoD was transiently expressed. The resulting DMD expression was sufficient to perform exon skipping experiments (although reproducibility favors the stably transfected lines.)

Example 9

Intravenous Injection of AAV9-U7_ACCA in the Dup2 Mouse Model Results in Significant Expression of the N-Truncated Isoform and Correction of Strength Deficit.

We tested the ability of an AAV9-U7-ACCA genome to skip exon 2 in vivo in Dup2 mice upon intravenous injection. The U7-ACCA genome was cloned into a rAAV9 vector (designated AAV9-U7_ACCA herein) for administration to the mice. AAV9-U7_ACCA was injected into the tail vein (3.3E12 vg/kg) of five Dup2 mice. One month after injection, treated animals were examined.

Results of the experiment are shown in FIG. 17.

Figures 19A, 19B:
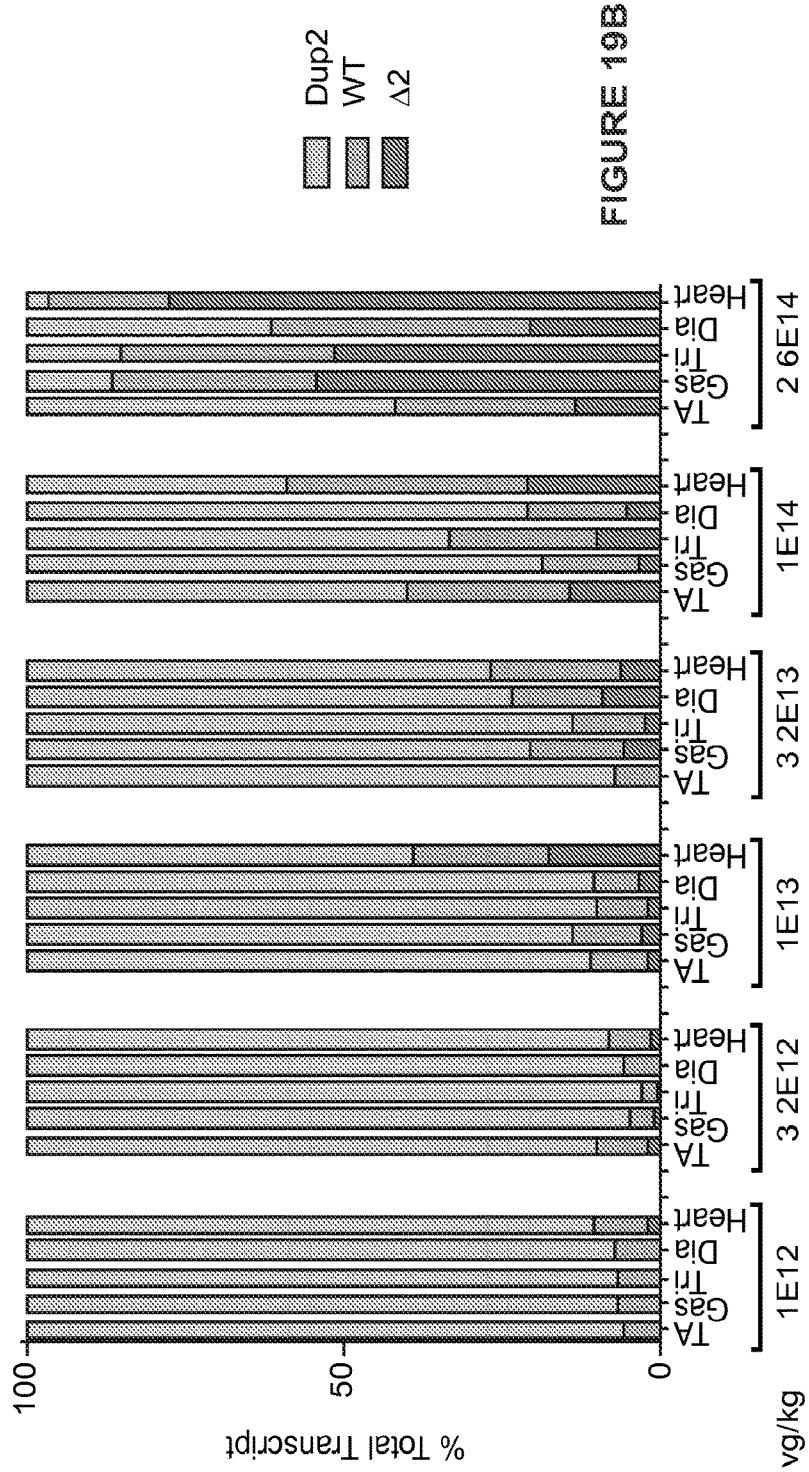
Figure 19C:
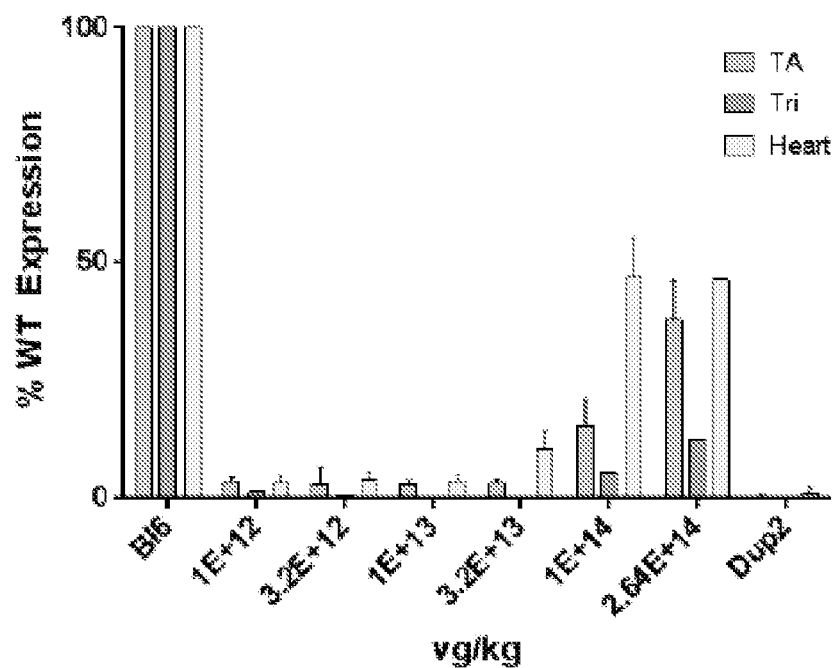
Figure 19D:
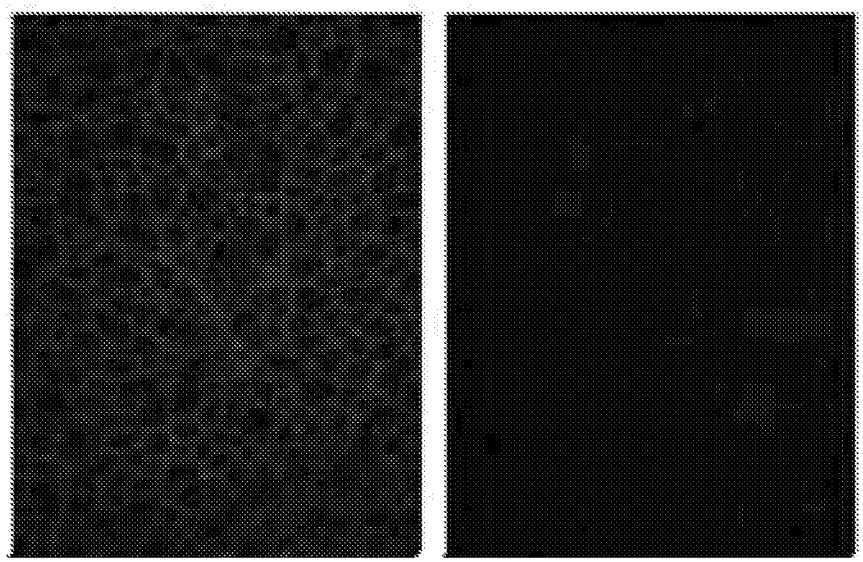
Figure 19E:
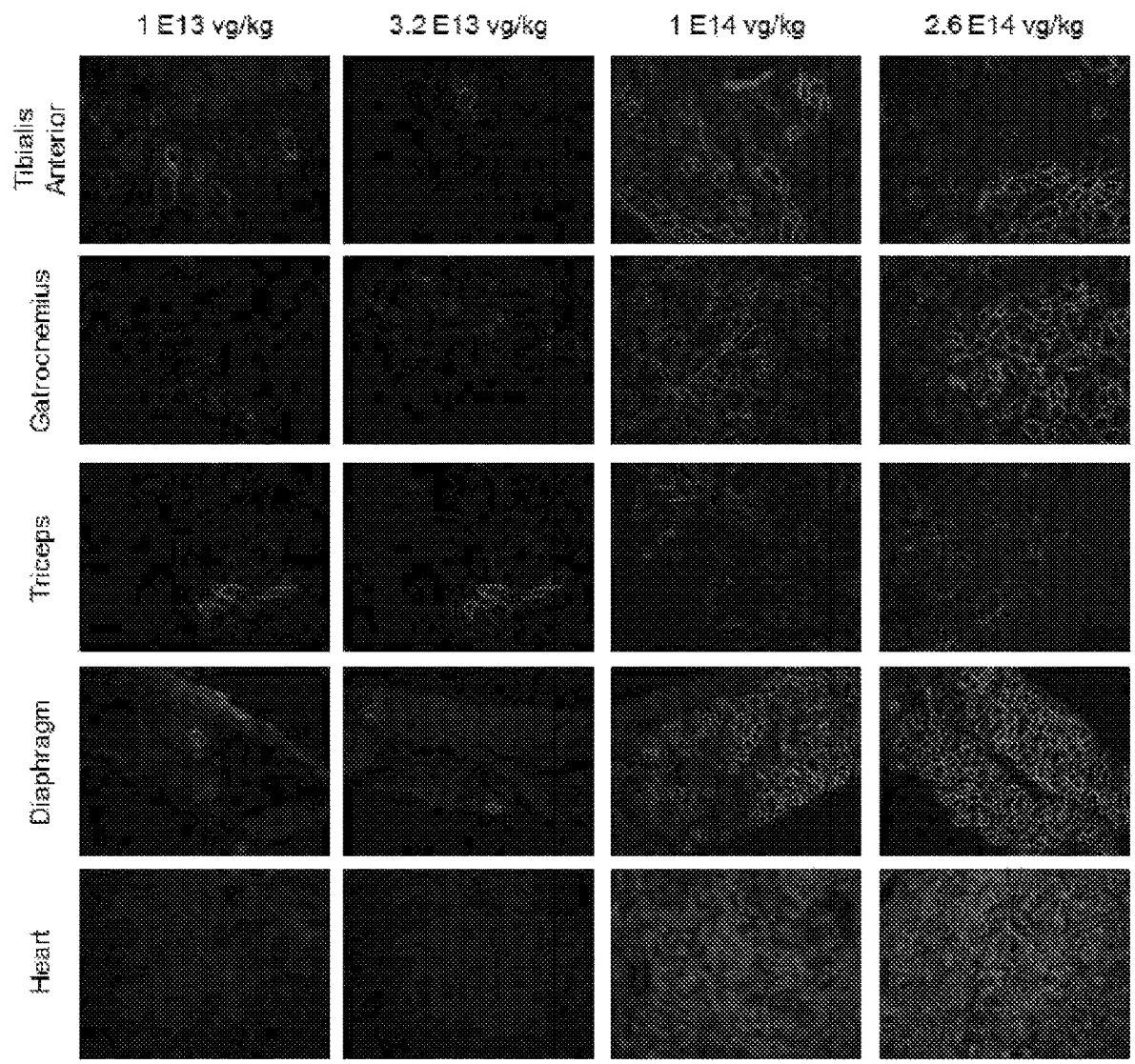

We also carried out dose escalation studies of intravenous dosing (FIG. 19*a*). As seen in FIG. 19*b*, the degree of skipped transcript shows an expected dose response, as was seen in the IM studies. At the highest level, the majority of transcript consists of either wild-type transcript, which is translated into full-length dystrophin, or exon 2-deleted transcript, which is translated into the N-truncated isoform; importantly, either isoform provides a functional benefit to the mouse (as to humans). FIG. 19*c* shows a similar expected dose response in protein expression. Quite importantly, in terms of clinical utility, at the higher doses there is unquestionable and abundant expression of dystrophin in the diaphragm and heart muscles. Quantification of protein expression on immunoblot (FIG. 19*d*) confirms the dose escalation response.

Newborn screening (NBS) for DMD in human newborns is now feasible, therefore we tested the benefits of early expression of the N-truncated isoform by delivery of AAV9.U7-ACCA vector ($8 \times 10^{11}$ vg) results at postnatal day 1 (P1) in Dup2 mice. This single injection results in widespread expression of the N-truncated isoform in all muscles, with sustained protection of muscle fibers through one and six months post treatment (FIG. 20).

Example 10

PPMOs having following sequences (shown 5' to 3') are administered to Dup2 mice.

```
C antisense oligomer:
AUUCUUACCUUAGAAAAUUGUGC           (SEQ ID NO: 10)

AL antisense oligomer:
GUUUUCUUUUGAACAUCUUCUCUUUCAUCUA   (SEQ ID NO: 11)
```

We transfected the AL-PPMO into wild type C2C12 mouse myoblasts (FIG. 22). Three days following transfection, an RT-PCR was performed and demonstrated an efficient exon 2 skipping (FIG. 22*a*). A similar experiment was performed in the Dup2 mouse model. Intramuscular injection of the AL-PPMO into the tibialis anterior (TA) of Dup2 mice was performed in order to assess the degree of exon 2 skipping and protein expression. As seen in FIG. 22*b*, exon 2 skipping was achieved efficiently. FIG. 22*c* was obtained using the same treated TA muscles. Immunostaining of dystrophin was carried out and of dystophrin the results demonstrated efficient production and localization to the plasma membrane protein.

In another experiment, systemic injections are given in the tail vein of another cohort of mice of three doses weekly at 12 mg/kg. We will evaluate skipping and dystrophin restoration at 4 weeks after the first injection.

Example 11

Patients harboring a nonsense mutation within exon 1 or 2 still express the highly functional N-terminally truncated dystrophin isoform. This is due to the presence of IRES in exon 5 that allow re-entry of the ribosome and translation from exon 6. Therefore we hypothesize that creation of a nonsense mutation should force activation of the IRES in human patient cell lines carrying either missense mutation or in frame deletion duplication, within exon 1 to 4. Only removal of exon 2 generates a stop codon in exon 3. Therefore complete skipping of exon 2 in patient carrying the above mentioned mutation, would induce a stop codon in exon 3, and thereby production of the IRES-mediated N-terminally truncated isoform.

We collected cells from human patients carrying mutation in these exons. The cells were then infected with a lentivirus expressing an inducible MyoD that forces conversion of fibroblasts to myoblasts which can then be further differentiated into myotubes, the cell type that expresses dystrophin (referred to hereafter as "myofibroblasts"). Despite aiming to collect cells from patients harboring missense mutation or in frame deletion or duplication within exon 1 to 4, only cells from patient carrying a nonsense mutation were available. These cells were derived from BMD patients, and as they carry a nonsense mutation they already naturally expressed the N-terminally truncated dystrophin isoform. However, treatment with AAV1.U7-ACCA at differentiation resulted in higher expression of the IRES-initiated isoform by day 14 (FIG. 21).

DISCUSSION OF RESULTS IN THE EXAMPLES

We have demonstrated the presence of a glucocorticoid-responsive IRES within DMD exon 5 that can drive the expression of an N-truncated but functional dystrophin. Ribosome profiling from a BMD patient with an exon 2 frameshifting mutation demonstrated a mild reduction in dystrophin translation efficiency and a ribosome footprint pattern consistent with ribosome loading beginning in exons 5 and 6. The relevance of this IRES-induced isoform to the amelioration of disease severity, which we first described in patients with exon 1 nonsense mutations [Flanigan et al., *Neuromuscular Disorders: NMD*, 19: 743-748 (2009)], is also confirmed by the mass spectrometric data from the first ever reported case of an exon 2 deletion, found in an entirely asymptomatic subject. Finally, in a novel therapeutic approach, we have induced out-of-frame exon-skipping to generate a premature stop codon and consequently force activation of the IRES in both patient-derived cell lines and in a novel DMD mouse model, in which we restored components of the dystrophin complex and corrected the pathologic and physiologic features of muscle injury.

Most eukaryotic mRNAs are monocistronic and possess a specialized cap structure at their 5' terminus, which is required for translation initiation as this is where scanning by the 40S ribosomal subunit begins. Despite clear evidence for the cap-dependent 5'→3' scanning model of initiation, bioinformatic analysis has suggested that ~50% of human transcripts contain 5'UTR short upstream open reading frames (uORFs) that may mediate transcript-specific translation efficiency and control. uORFs may function by modulating either leaky scanning or termination-dependent reinitiation, although uORFs can also dynamically regulate access to IRES elements as shown for the mammalian cationic amino acid transporter 1 gene, CAT1/SLC7A1. Recognizing the cautions raised regarding IRES identification via reporter assays, all control experiments performed in this study—including assessment of RNA integrity by RT-PCR and Northern blot, use of a promoterless plasmid, and use of an appropriate positive IRES control—were consistent with cap-independent initiation due to IRES activity. We mapped a minimal region harboring a DMD IRES activity to 71 nt, of a small length compared to EMCV (588 nt) but similar in size to that identified in the c-myc 5'UTR (50 nt). This is an important feature as such small IRESs can be used in dicistronic vectors, where space is limited when packaged into viral vectors such as AAV.

Although the precise molecular mechanism by which cellular IRESs modulate translation has not been defined in the literature, the requirement of ITAFs has been strongly suggested. These cellular proteins act in trans to augment IRES activity. Almost all ITAFs have been shown to harbor RNA binding domains and have been hypothesized to act as RNA chaperones, helping the IRES primary sequence attain appropriate conformational state intrinsic to its activity. This is likely relevant to the loss of dystrophin IRES activity in the presence of an exon 2 duplication, which may ablate IRES function by formation of a complex secondary structure or cause the formation of an inhibitory uORF that interferes with ITAF access to the exon 5 IRES.

Our results provide a molecular explanation for the rescue of 5' truncating mutations via a heretofore undescribed mechanism of post-transcriptional regulation of dystrophin expression. The identification of this new cellular IRES and the resultant dystrophin isoform has significant implications for understanding the basic biology of muscle and dystrophin. We note that exon 5 of DMD is highly conserved, with 87% identity to human found in the dog, mouse, horse, and chicken DMD genes, and 67% among 39 species including *D. rerio* and *X. tropicalis*. The presence of an IRES within such a highly conserved region strongly suggests selective pressure favoring a programmed role for alternate translation initiation. The role of the IRES under normal conditions is unclear, but ongoing efforts to understand the relevant cell lineage-specific and/or conditional activation signals will shed light on underlying mechanisms of IRES control and elucidate potentially novel functions of dystrophin.

An intriguing question is how the N-truncated isoform remains functional. A key cellular role for dystrophin is presumed to be transmitting the force of contraction across the sarcolemma to extracellular structures by serving as an important architectural bridge role between the F-actin cytoskeleton and the muscle plasma membrane. Two regions within dystrophin are responsible for F-actin binding: ABD1 (actin binding domain, spanning residues 15-237) and ABD2 (spanning residues 1468-2208). A number of studies have shown a lack of stability of dystrophin in the setting of deletions within the ABD1 domain. However, we note that most of these studies were performed with microdystrophin constructs lacking the ABD2 domain, which has been shown to enhance the interaction between ABD1 and actin. Such miniproteins bind actin and modify actin dynamics in a different manner compared to the full length version. Although results with such constructs show that absence of ABD2 does not completely abrogate binding of dystrophin to actin, it is unlikely that absence of ABD1 completely disrupts the interaction between dystrophin and actin. Expression of transgenes deleted for ABD1 lessens the mdx phenotype and restores the costameric pattern of the M band and Z lines, suggesting that the link between dystrophin and the subsarcolemmal cytoskeleton involves more than an interaction with ABD1. In agreement with this, other members of the cytoskeleton have been shown to interact with the dystrophin spectrin-repeat.

Although some series suggest that BMD due to mutations affecting ABD1 is more severe [Beggs et al., American Journal of Human Genetics, 49: 54-67 (1991)], our clinical and experimental observations—as well reports of other BMD patients lacking part or all of the ABD1 domain [Winnard et al., *Human Molecular Genetics*, 2: 737-744 (1993); Winnard et al., *American Journal of Human Genetics*, 56: 158-166 (1995) and Heald et al., *Neurology*, 44: 2388-2390 (1994)]—clearly indicate the significant functionality of the IRES-driven N-truncated isoform despite lacking the first half of the canonical ABD1 (FIG. 3a). This is of particular interest since forcing expression of this isoform by generating an out-of-frame transcript in order to induce IRES activity holds substantial therapeutic potential. This novel out-of-frame strategy could be combined with glucocorticoid treatment, a drug already used in DMD/BMD patients, which should increase IRES activation. Significantly, rather than being a personalized exon-skipping approach for patients with exon 2 duplications (who represent nearly 2% of DMD patients in one large series), out-of-frame skipping of exon 2 to induce expression of such a protein is contemplated for treatment of all patients who harbor mutations at the 5' end of the DMD gene (up to 6% in the same cohort) [Flanigan et al., *Neuromuscular Disorders: NMD*, 19: 743-748 (2009)].

While the present invention has been described in terms of specific embodiments, it is understood that variations and modifications will occur to those skilled in the art. Accordingly, only such limitations as appear in the claims should be placed on the invention.

All documents referred to in this application are hereby incorporated by reference in their entirety with particular attention to the content for which they are referred.

We claim:

1. A method of ameliorating Duchenne Muscular Dystrophy or Becker Muscular Dystrophy in a patient with a 5' mutation in a DMD gene but without a DMD exon 2 duplication, the method comprising the step of administering to the patient a recombinant adeno-associated virus (rAAV) comprising a DMD exon 5 internal ribosome entry site (IRES)-activating oligomer construct comprising
   (a) the nucleotide sequence set forth in SEQ ID NO: 6 or
   (b) a nucleotide sequence that expresses an RNA transcript comprising the nucleotide sequence set forth in SEQ ID NO: 10.

2. The method of claim 1 wherein the progression of a dystrophic pathology is inhibited in the patient.

3. The method of claim 1 wherein muscle function is improved in the patient.

4. The method of claim 3 wherein the improvement in muscle function is an improvement in muscle strength.

5. The method of claim 3 wherein the improvement in muscle function is an improvement in stability in standing and walking.

6. The method of claim 1 wherein the genome of the rAAV lacks adeno-associated virus rep and cap DNA.

7. The method of claim 1 wherein the genome of the rAAV is a self-complementary genome and/or single-stranded genome.

8. The method of claim 1, wherein the rAAV is r-AAV1, r-AAV2, r-AAV3, r-AAV4, r-AAV5, r-AAV6, r-AAV7, r-AAV8, r-AAV9, r-AAV10, r-AAV11, or r-AAVrh74.

9. The method of claim 1, wherein the DMD exon 5 internal ribosome entry site (IRES)-activating oligomer construct further comprises the nucleotide sequence set forth in SEQ ID NO: 5.

10. The method of claim 1, wherein the DMD exon 5 internal ribosome entry site (IRES)-activating oligomer construct comprises the nucleotide sequence set forth in SEQ ID NO: 6.

11. The method of claim 1, wherein the DMD exon 5 internal ribosome entry site (IRES)-activating oligomer construct further comprises the nucleotide sequence set forth in SEQ ID NO: 7.

12. The method of claim 1, wherein the DMD exon 5 internal ribosome entry site (IRES)-activating oligomer construct further comprises the nucleotide sequence set forth in SEQ ID NO: 8.

13. The method of claim 1, wherein the DMD exon 5 internal ribosome entry site (IRES)-activating oligomer construct further comprises the nucleotide sequence that expresses an RNA comprising the nucleotide sequence set forth in SEQ ID NO: 9.

14. The method of claim 1, wherein the DMD exon 5 internal ribosome entry site (IRES)-activating oligomer construct comprises the nucleotide sequence that expresses an RNA comprising the nucleotide sequence set forth in SEQ ID NO: 10.

15. The method of claim 1, wherein the DMD exon 5 internal ribosome entry site (IRES)-activating oligomer construct further comprises the nucleotide sequence that expresses an RNA comprising the nucleotide sequence set forth in SEQ ID NO: 11.

16. The method of claim 1, wherein the DMD exon 5 internal ribosome entry site (IRES)-activating oligomer construct further comprises the nucleotide sequence that expresses an RNA comprising the nucleotide sequence set forth in SEQ ID NO: 12.

17. The method of claim 1, wherein the DMD exon 5 internal ribosome entry site (IRES)-activating oligomer construct comprises two or more copies of the nucleotide sequence set forth in SEQ ID NO: 6.

18. The method of claim 1, wherein the DMD exon 5 internal ribosome entry site (IRES)-activating oligomer construct further comprises two or more copies of the nucleotide sequence set forth in SEQ ID NO: 7.

19. The method of claim 1, wherein the DMD exon 5 internal ribosome entry site (IRES)-activating oligomer construct comprises at least two copies of the polynucleotide comprising the sequence set forth in SEQ ID NO: 6 and at least two copies of the polynucleotide comprising the sequence set forth in SEQ ID NO: 7.

20. The method of claim 1, wherein the DMD exon 5 internal ribosome entry site (IRES)-activating oligomer construct comprises two copies of the polynucleotide comprising the sequence set forth in SEQ ID NO: 6 and two copies of the polynucleotide comprising the sequence set forth in SEQ ID NO: 7.

21. The method of claim 1, wherein the DMD exon 5 internal ribosome entry site (IRES)-activating oligomer construct comprises two or more copies of the nucleotide sequence that expresses an RNA transcript comprising the nucleotide sequence set forth in SEQ ID NO: 10.

22. The method of claim 1, wherein the DMD exon 5 internal ribosome entry site (IRES)-activating oligomer construct further comprises two or more copies of the nucleotide sequence that expresses an RNA transcript comprising the nucleotide sequence set forth in SEQ ID NO: 11.

23. The method of claim 1, wherein the DMD exon 5 internal ribosome entry site (IRES)-activating oligomer construct comprises at least two copies of the nucleotide sequence that expresses an RNA transcript comprising the nucleotide sequence set forth in SEQ ID NO: 10 and at least two copies of the nucleotide sequence that expresses an RNA transcript comprising the nucleotide sequence set forth in SEQ ID NO: 11.

24. The method of claim 1, wherein the DMD exon 5 internal ribosome entry site (IRES)-activating oligomer construct comprises two copies of the nucleotide sequence that expresses an RNA transcript comprising the nucleotide sequence set forth in SEQ ID NO: 10 and two copies of the nucleotide sequence that expresses an RNA transcript comprising the nucleotide sequence set forth in SEQ ID NO: 11.

25. The method of claim 1, wherein the DMD exon 5 internal ribosome entry site (IRES)-activating oligomer construct comprises two copies of the nucleotide sequence that expresses an RNA transcript comprising the nucleotide sequence set forth in SEQ ID NO: 10 and two copies of the nucleotide sequence that expresses an RNA transcript comprising the nucleotide sequence set forth in SEQ ID NO: 11.

26. The method of claim 8 wherein the rAAV is r-AAV1, r-AAV6, r-AAV8, r-AAV9, or r-AAV rh74.

27. The method of claim 1, 6, 7, or 26, further comprising administering a glucocorticoid to the patient.

* * * * *

SEQUENCE LISTING

```
<160> NUMBER OF SEQ ID NOS: 34

<210> SEQ ID NO 1
<211> LENGTH: 28
<212> TYPE: DNA
<213> ORGANISM: Homo sapiens

<400> SEQUENCE: 1
tcaaaagaaa acattcacaa aatgggta                                      28

<210> SEQ ID NO 2
<211> LENGTH: 23
<212> TYPE: DNA
<213> ORGANISM: Homo sapiens

<400> SEQUENCE: 2
gcacaatttt ctaaggtaag aat                                           23

<210> SEQ ID NO 3
<211> LENGTH: 31
<212> TYPE: DNA
<213> ORGANISM: Homo sapiens

<400> SEQUENCE: 3
tagatgaaag agaagatgtt caaaagaaaa c                                  31

<210> SEQ ID NO 4
<211> LENGTH: 21
<212> TYPE: DNA
<213> ORGANISM: Homo sapiens

<400> SEQUENCE: 4
tagatgaaag agaagatgtt c                                             21

<210> SEQ ID NO 5
<211> LENGTH: 28
<212> TYPE: DNA
<213> ORGANISM: Adeno-associated virus

<400> SEQUENCE: 5
tacccatttt gcgaatgttt tcttttga                                      28

<210> SEQ ID NO 6
<211> LENGTH: 23
<212> TYPE: DNA
<213> ORGANISM: Adeno-associated virus

<400> SEQUENCE: 6
```

-continued

```
attcttacct tagaaaattg tgc                                          23

<210> SEQ ID NO 7
<211> LENGTH: 31
<212> TYPE: DNA
<213> ORGANISM: Adeno-associated virus

<400> SEQUENCE: 7
gttttctttt gaagatcttc tctttcatct a                                 31

<210> SEQ ID NO 8
<211> LENGTH: 21
<212> TYPE: DNA
<213> ORGANISM: Adeno-associated virus

<400> SEQUENCE: 8
gaagatcttc tctttcatct a                                            21

<210> SEQ ID NO 9
<211> LENGTH: 28
<212> TYPE: RNA
<213> ORGANISM: Homo sapiens

<400> SEQUENCE: 9
uacccauuuu gcgaauguuu ucuuuuga                                     28

<210> SEQ ID NO 10
<211> LENGTH: 23
<212> TYPE: RNA
<213> ORGANISM: Homo sapiens

<400> SEQUENCE: 10
auucuuaccu uagaaaauug ugc                                          23

<210> SEQ ID NO 11
<211> LENGTH: 31
<212> TYPE: RNA
<213> ORGANISM: Homo sapiens

<400> SEQUENCE: 11 guuucuuuu gaacaucuuc ucuuucaucu a                                  31

<210> SEQ ID NO 12
<211> LENGTH: 21
<212> TYPE: RNA
<213> ORGANISM: Homo sapiens

<400> SEQUENCE: 12
gaacaucuuc ucuuucaucu a                                            21

<210> SEQ ID NO 13
<211> LENGTH: 30
<212> TYPE: RNA
<213> ORGANISM: Homo sapiens

<400> SEQUENCE: 13
ccauuuugug aauguuuucu uugaacauc                                    30

<210> SEQ ID NO 14
<211> LENGTH: 4472
<212> TYPE: DNA
<213> ORGANISM: Adeno-associated virus rh74
```

<400> SEQUENCE: 14

```
ctccatcact agggtaacc gcgaagcgcc tcccacgctg ccgcgtcagc gctgacgtaa      60
attacgtcat aggggagtgg tcctgtatta gctgtcacgt gagtgctttt gcgacatttt     120
gcgacaccac gtggccattc atggtatata tggccgagtg agcgagcagg atctccattt     180
tgaccgcgaa atttgaacga gcagcagcca tgccgggctt ctacgagatc gtgcttaagg     240
tgccgagcga cctggacgag cacctgccgg gcatttctga ctcgtttgtg aactgggtgg     300
cagagaagga atgggagctg ccccggatt ctgacatgga tcggaatctg attgagcagg      360
caccctgac cgtggccgag aagctacagc gcgacttcct ggtccaatgg cgccgcgtga      420
gtaaggcccc ggaggccctc ttctttgttc agttcgagaa gggcgagtcc tacttccacc     480
tccatattct ggtagagacc acggggtca atccatggt gctgggccgc ttcctgagtc       540
agattcggga caagctggtg cagaccatct accgcgggat cgagccgacc ctgcccaact     600
ggttcgcggt gacaaagacg cgtaatggcg ccggaggggg gaacaaggtg gtggacgagt     660
gctacatccc caactacctg ctgcccaaga ctcagcccga gctgcagtgg gcgtggacta     720
acatggagga gtatataagc gcgtgcttga acctggccga gcgcaaacgg ctcgtggcgc     780
agcacctgac ccacgtcagc cagacccagg agcagaacaa ggagaatctg aacccgaatt     840
ctgacgcgcc tgtcatccgg tcaaaaacct ccgcgcgcta catggagctg gtcgggtggc     900
tggtggaccg gggcatcacc tccgagaagc agtggatcca ggaggaccag gcctcgtaca     960
tctccttcaa cgccgcctcc aactcgcggt ctcagatcaa ggccgcgctg acaatgccg     1020
gcaagatcat ggcgctgacc aaatccgcgc ccgactacct ggtaggcccc gctctgcccg    1080
cggacattaa atccaaccgc atctaccgca tcctggagct gaatggctac gaccctgcct    1140
acgccggttc cgtctttctc ggctgggccc agaaaaagtt tggcaaaagg aacaccatct    1200
ggctgtttgg gccggccacc acgggcaaga ccaacatcgc ggaagccatc gcccacgccg    1260
tgcccttcta cggctgcgtc aactggacca atgagaactt tcccttcaac gattgcgtcg    1320
acaagatggt gatctggtgg gaggagggca agatgacggc caaggtcgtg gagtccgcca    1380
aggccattct cggcggcagc aaggtgcgcg tggaccaaaa gtgcaagtcg tccgcccaga    1440
tcgatcccac ccccgtgatc gtcacctcca acaccaacat gtgcgccgtg attgacggga    1500
acagcaccac cttcgagcac cagcagccgt tgcaggaccg gatgttcaaa tttgaactta    1560
cccgccgtct ggagcacgac tttggcaagg tgacaaagca ggaagtcaaa gagttcttcc    1620
gctgggcgca ggatcacgtg accgaggtgg cgcatgagtt ctacgtcaga aagggtggag    1680
ctaacaaaag acccgccccc gatgacgcgg atataagcga gcccaagcgg gcctgcccct    1740
cagtcgcgga tccatcgacg tcagacgcgg aaggagctcc ggtggacttt gccgacaggt    1800
accaaaacaa atgttctcgt cacgcgggca tgcttcagat gctgtttccc tgcaaaacat    1860
gcgagagaat gaatcagaat ttcaacattt gcttcacgca cgggaccaga gactgttcag    1920
aatgtttccc tggcgtgtca gaatctcaac cggtcgtcag aaaaaagacg tatcggaaac    1980
tctgtgcgat tcatcatctg ctggggcggg cacccgagat tgcttgctcg gcctgcgacc    2040
tggtcaacgt ggacctggat gactgtgttt ctgagcaata aatgacttaa accaggtatg    2100
gctgccgatg gttatcttcc agattggctc gaggacaacc tctctgaggg cattcgcgag    2160
tggtgggacc tgaaacctgg agccccgaaa cccaaagcca accagcaaaa gcaggacaac    2220
ggccggggtc tggtgcttcc tggctacaag tacctcggac ccttcaacgg actcgacaag    2280
ggggagcccg tcaacgcggc ggacgcagcg gccctcgagc acgacaaggc ctacgaccag    2340
```

```
cagctccaag cgggtgacaa tccgtacctg cggtataatc acgccgacgc cgagtttcag    2400
gagcgtctgc aagaagatac gtcttttggg ggcaacctcg ggcgcgcagt cttccaggcc    2460
aaaaagcggg ttctcgaacc tctgggcctg gttgaatcgc cggttaagac ggctcctgga    2520
aagaagagac cggtagagcc atcacccag cgctctccag actcctctac gggcatcggc     2580
aagaaaggcc agcagcccgc aaaaaagaga ctcaattttg gcagactgg cgactcagag     2640 tcagtccccg accctcaacc aatcggaaa ccaccagcag gccctctgg tctgggatct      2700 ggtacaatgg ctgcaggcgg tggcgctcca atggcagaca taacgaagg cgccgacgga     2760 gtgggtagtt cctcaggaaa ttggcattgc gattccacat ggctgggcga cagagtcatc    2820
accaccagca cccgcacctg ggccctgccc acctacaaca accacctcta caagcaaatc    2880
tccaacggga cctcgggagg aagcaccaac gacaacacct acttcggcta cagcaccccc    2940
tgggggtatt ttgacttcaa cagattccac tgccactttt caccacgtga ctggcagcga    3000
ctcatcaaca caactggggg attccggccc aagaggctca acttcaagct cttcaacatc    3060
caagtcaagg aggtcacgca gaatgaaggc accaagacca tcgccaataa ccttaccagc    3120
acgattcagg tctttacgga ctcggaatac cagctcccgt acgtgctcgg tcggcgcac    3180 cagggctgcc tgcctccgtt cccggcggac gtcttcatga ttcctcagta cgggtacctg    3240
actctgaaca atggcagtca ggctgtgggc cggtcgtcct tctactgcct ggagtacttt    3300
ccttctcaaa tgctgagaac gggcaacaac tttgaattca gctacaactt cgaggacgtg    3360
cccttccaca gcagctacgc gcacagccag agcctggacc ggctgatgaa ccctctcatc    3420
gaccagtact tgtactacct gtcccggact caaagcacgg gcggtactgc aggaactcag    3480
cagttgctat tttctcaggc cgggcctaac aacatgtcgg ctcaggccaa gaactggcta    3540
cccggtccct gctaccggca gcaacgcgtc tccacgacac tgtcgcagaa caacaacagc    3600
aactttgcct ggacgggtgc caccaagtat catctgaatg gcagagactc tctggtgaat    3660
cctggcgttg ccatggctac ccacaaggac gacgaagagc gattttttcc atccagcgga    3720
gtcttaatgt ttgggaaaca gggagctgga aagacaacg tggactataq cagcgtgatg     3780 ctaaccagcg aggaagaaat aaagaccacc aacccagtgg ccacagaaca gtacggcgtg    3840
gtggccgata acctgcaaca gcaaaacgcc gctcctattg taggggccgt caatagtcaa    3900
ggagccttac ctgcatggt gtggcagaac cgggacgtgt acctgcaggg tcccatctgg    3960
gccaagattc ctcatacgga cggcaacttt catccctcgc cgctgatggg aggctttgga    4020
ctgaagcatc cgcctcctca gatcctgatt aaaaacacac tgttcccgc ggatcctccg    4080 accaccttca ctaaggccaa gctggcttct ttcatcacgc agtacagtac cggccaggtc    4140
agcgtggaga tcgagtggga gctgcagaag gagaacagca acgctggaa cccagagatt    4200 cagtacactt ccaactacta caaatctaca aatgtggact tgctgtcaa tactgagggt    4260 acttattccg agcctcgccc cattggcacc cgttacctca cccgtaatct gtaattacat    4320
gttaatcaat aaaccggtta attcgtttca gttgaacttt ggtctcctgt ccttcttatc    4380
ttatcggtta ccatagaaac tggttactta ttaactgctt ggtgcgcttc gcgataaaag    4440
acttacgtca tcgggttacc cctagtgatg ga                                   4472
```

<210> SEQ ID NO 15
<211> LENGTH: 2052
<212> TYPE: DNA
<213> ORGANISM: Adeno-associated virus

<400> SEQUENCE: 15

```
cgaccgcgcg agcgagcgag tgactccggc gggcccgttt cgggcccgca gcccgctgga      60
aaccagcggg ccggagtcac tcgctcgctc gcgcgtctct ccctcaccgg ttgaggtagt     120
gatccccaag gaacatcaat tactaattgg gcggtacgat gaatagatgc atcggtacga     180
gatctattgt tgtatcctcg acactaaccg acaaaagtcg gttagtcgtg actgagtaaa     240
cgtatcggaa atgttcgcca gtgtttgagt tctttgctcg ccaaaattat cagaaaatct     300
tataacaaat agcttggctt attccttgac acgaaacact aagtgtatag tcacctcccc     360
acacctttac cgtggaacta gagtgggagt agctttcacc tcaactacag gaagggaccg     420
agcgatgtct gcgtgaaggc gttcaaaaga aaacttctag aagagaaagt agatttaaaa     480
acctcgtcca aaagactgaa gccagccttt tggggagggt taaagtgacc agatgttact     540
ttcgttttgt caagagaagg ggcgaggggc cacacactct ccccgaaact aggaagagac     600
caaaggatcc tttgcgcata caccgatcta ttgttgtatc ctcgacacta accgacaaaa     660
gtcggttagt cgtgactgag taaacgtatc ggaaatgttc gccagtgttt gagttctttg     720
ctcgccaaaa ttatcagaaa atcttataac aaatagcttg gcttattcct tgacacgaaa     780
cactaagtgt atagtcacct ccccacacct ttaccgtgga actagagtgg gagtagcttt     840
cacctcaact acaggaaggg accgagcgat gtctgcgtga aggcgtttaa gaatggaatc     900
ttttaacacg ttaaaaacct cgtccaaaag actgaagcca ccttttggg gagggttaaa     960
gtgaccagat gttactttcg ttttgtcaag agaaggggcg aggggccaca cactctcccc    1020
gaaactagga agagaccaaa ggatcctttg cgcatacacc gatctattgt tgtatcctcg    1080
acactaaccg acaaaagtcg gttagtcgtg actgagtaaa cgtatcggaa atgttcgcca    1140
gtgtttgagt tctttgctcg ccaaaattat cagaaaatct tataacaaat agcttggctt    1200
attccttgac acgaaacact aagtgtatag tcacctcccc acacctttac cgtggaacta    1260
gagtgggagt agctttcacc tcaactacag gaagggaccg agcgatgtct gcgtgaaggc    1320
gtttaagaat ggaatctttt aacacgttaa aaacctcgtc caaaagactg aagccagcct    1380
tttggggagg gttaaagtga ccagatgtta ctttcgtttt gtcaagagaa ggggcgaggg    1440
gccacacact ctccccgaaa ctaggaagag accaaaggat cctttgcgca tacaccgatc    1500
tattgttgta tcctcgacac taaccgacaa aagtcggtta gtcgtgactg agtaaacgta    1560
tcggaaatgt tcgccagtgt ttgagttctt tgctcgccaa aattatcaga aaatcttata    1620
acaaatagct tggcttattc cttgacacga aacactaagt gtatagtcac ctccccacac    1680
ctttaccgtg gaactagagt gggagtagct ttcacctcaa ctacaggaag ggaccgagcg    1740
atgtctgcgt gaaggcgttc aaaagaaaac ttctagaaga gaaagtagat ttaaaaacct    1800
cgtccaaaag actgaagcca gccttttggg gagggttaaa gtgaccagat gttactttcg    1860
ttttgtcaag agaaggggcg aggggccaca cactctcccc gaaactagga agagaccaaa    1920
ggatcctttg cgcatacaca tgttgggtg agggagagac gcgcgagcga gcgagtgact    1980
ccggcccgct ggtttccagc gggctgcggg cccgaaacgg gcccgccgga gtcactcgct    2040
cgctcgcgcg tc                                                         2052
```

<210> SEQ ID NO 16
<211> LENGTH: 8
<212> TYPE: PRT
<213> ORGANISM: Homo sapiens

<400> SEQUENCE: 16

```
Trp Val Asn Ala Gln Phe Ser Lys
1               5

<210> SEQ ID NO 17
<211> LENGTH: 14
<212> TYPE: PRT
<213> ORGANISM: Homo sapiens

<400> SEQUENCE: 17

Gln His Ile Glu Asn Leu Phe Ser Asp Leu Gln Asp Gly Arg
1               5                   10

<210> SEQ ID NO 18
<211> LENGTH: 12
<212> TYPE: PRT
<213> ORGANISM: Homo sapiens

<400> SEQUENCE: 18

Leu Leu Asp Leu Leu Glu Gly Leu Thr Gly Gln Lys
1               5                   10

<210> SEQ ID NO 19
<211> LENGTH: 23
<212> TYPE: PRT
<213> ORGANISM: Homo sapiens

<400> SEQUENCE: 19

Val Leu Gln Asn Asn Asn Val Asp Leu Val Asn Ile Gly Ser Thr Asp
1               5                   10                  15

Ile Val Asp Gly Asn His Lys
            20

<210> SEQ ID NO 20
<211> LENGTH: 13
<212> TYPE: PRT
<213> ORGANISM: Homo sapiens

<400> SEQUENCE: 20

Asn Leu Met Ala Gly Leu Gln Gln Thr Asn Ser Glu Lys
1               5                   10

<210> SEQ ID NO 21
<211> LENGTH: 9
<212> TYPE: PRT
<213> ORGANISM: Homo sapiens

<400> SEQUENCE: 21

Leu Glu His Ala Phe Asn Ile Ala Arg
1               5

<210> SEQ ID NO 22
<211> LENGTH: 7
<212> TYPE: PRT
<213> ORGANISM: Homo sapiens

<400> SEQUENCE: 22

Tyr Gln Leu Gly Ile Glu Lys
1               5

<210> SEQ ID NO 23
<211> LENGTH: 15
<212> TYPE: PRT
<213> ORGANISM: Homo sapiens
```

<400> SEQUENCE: 23

Leu Leu Asp Pro Glu Asp Val Asp Thr Thr Tyr Pro Asp Lys Lys
1               5                   10                  15

<210> SEQ ID NO 24
<211> LENGTH: 17
<212> TYPE: PRT
<213> ORGANISM: Homo sapiens

<400> SEQUENCE: 24

Ser Tyr Ala Tyr Thr Gln Ala Ala Tyr Val Thr Thr Ser Asp Pro Thr
1               5                   10                  15

Arg

<210> SEQ ID NO 25
<211> LENGTH: 14
<212> TYPE: PRT
<213> ORGANISM: Homo sapiens

<400> SEQUENCE: 25

Ser Pro Phe Pro Ser Gln His Leu Glu Ala Pro Glu Asp Lys
1               5                   10

<210> SEQ ID NO 26
<211> LENGTH: 2052
<212> TYPE: DNA
<213> ORGANISM: Adeno-associated virus

<400> SEQUENCE: 26

```
gctggcgcgc tcgctcgctc actgaggccg cccgggcaaa gcccgggcgt cgggcgacct     60
ttggtcgccc ggcctcagtg agcgagcgag cgcgcagaga gggagtggcc aactccatca    120
ctaggggttc cttgtagtta atgattaacc cgccatgcta cttatctacg tagccatgct    180
ctagataaca acataggagc tgtgattggc tgttttcagc caatcagcac tgactcattt    240
gcatagcctt tacaagcggt cacaaactca agaaacgagc ggttttaata gtcttttaga    300
atattgttta tcgaaccgaa taaggaactg tgctttgtga ttcacatatc agtggagggg    360
tgtggaaatg gcaccttgat ctcaccctca tcgaaagtgg agttgatgtc cttccctggc    420
tcgctacaga cgcacttccg caagttttct tttgaagatc ttctctttca tctaaatttt    480
tggagcaggt tttctgactt cggtcggaaa acccctccca atttcactgg tctacaatga    540
aagcaaaaca gttctcttcc ccgctccccg gtgtgtgaga ggggctttga tccttctctg    600
gtttcctagg aaacgcgtat gtggctagat aacaacatag gagctgtgat tggctgtttt    660
cagccaatca gcactgactc atttgcatag cctttacaag cggtcacaaa ctcaagaaac    720
gagcggtttt aatagtcttt tagaatattg tttatcgaac cgaataagga actgtgcttt    780
gtgattcaca tatcagtgga ggggtgtgga atggcacct tgatctcacc ctcatcgaaa    840
gtggagttga tgtccttccc tggctcgcta cagacgcact tccgcaaatt cttaccttag    900
aaaattgtgc aattttttgga gcaggttttc tgacttcggt cggaaaaccc ctcccaattt    960
cactggtcta caatgaaagc aaaacagttc tcttccccgc tccccggtgt gtgagagggg   1020
ctttgatcct tctctggttt cctaggaaac gcgtatgtgg ctagataaca acataggagc   1080
tgtgattggc tgttttcagc caatcagcac tgactcattt gcatagcctt tacaagcggt   1140
cacaaactca agaaacgagc ggttttaata gtcttttaga atattgttta tcgaaccgaa   1200
taaggaactg tgctttgtga ttcacatatc agtggagggg tgtggaaatg gcaccttgat   1260
```

```
ctcaccctca tcgaaagtgg agttgatgtc cttccctggc tcgctacaga cgcacttccg    1320
caaattctta ccttagaaaa ttgtgcaatt tttggagcag ttttctgac ttcggtcgga     1380 aaacccctcc caatttcact ggtctacaat gaaagcaaaa cagttctctt ccccgctccc    1440
cggtgtgtga gaggggcttt gatccttctc tggtttccta ggaaacgcgt atgtggctag    1500
ataacaacat aggagctgtg attggctgtt ttcagccaat cagcactgac tcatttgcat    1560
agcctttaca agcggtcaca aactcaagaa acgagcggtt taatagtct tttagaatat     1620 tgtttatcga accgaataag gaactgtgct ttgtgattca catatcagtg gagggggtgtg   1680 gaaatggcac cttgatctca ccctcatcga aagtggagtt gatgtccttc cctggctcgc    1740
tacagacgca cttccgcaag ttttcttttg aagatcttct ctttcatcta aattttttgga  1800 gcaggttttc tgacttcggt cggaaaaccc ctcccaattt cactggtcta caatgaaagc   1860
aaaacagttc tcttccccgc tccccggtgt gtgagagggg ctttgatcct tctctggttt    1920
cctaggaaac gcgtatgtgt acaaccccac tccctctctg cgcgctcgct cgctcactga    1980
ggccgggcga ccaaaggtcg cccgacgccc gggctttgcc cgggcggcct cagtgagcga    2040
gcgagcgcgc ag                                                        2052
```

<210> SEQ ID NO 27
<211> LENGTH: 240
<212> TYPE: PRT
<213> ORGANISM: Homo sapiens
<300> PUBLICATION INFORMATION:
<308> DATABASE ACCESSION NUMBER: UniProtKB/Swiss-Prot: P11532.3
<309> DATABASE ENTRY DATE: 2015-07-22
<313> RELEVANT RESIDUES IN SEQ ID NO: (1)..(240)

<400> SEQUENCE: 27

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205
```

```
Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240
```

<210> SEQ ID NO 28
<211> LENGTH: 22
<212> TYPE: PRT
<213> ORGANISM: Homo sapiens

<400> SEQUENCE: 28

```
Tyr Gln Leu Gly Ile Glu Lys Leu Leu Asp Pro Glu Asp Val Asp Thr
1               5                   10                  15

Thr Tyr Pro Asp Lys Lys
            20
```

<210> SEQ ID NO 29
<211> LENGTH: 112
<212> TYPE: PRT
<213> ORGANISM: Homo sapiens

<400> SEQUENCE: 29

```
Trp Val Asn Ala Gln Phe Ser Lys Phe Gly Lys Gln His Ile Glu Asn
1               5                   10                  15

Leu Phe Ser Asp Leu Gln Asp Gly Arg Arg Leu Leu Asp Leu Leu Glu
            20                  25                  30

Gly Leu Thr Gly Gln Lys Val Leu Gln Asn Asn Asn Val Asp Leu Val
        35                  40                  45

Asn Ile Gly Ser Thr Asp Ile Val Asp Gly Asn His Lys Asn Ile Met
    50                  55                  60

Ala Gly Leu Gln Gln Thr Asn Ser Glu Lys Ile Leu Leu Glu His
65                  70                  75                  80

Ala Phe Asn Ile Ala Arg Tyr Gln Leu Gly Ile Glu Lys Leu Leu Asp
                85                  90                  95

Pro Glu Asp Val Asp Thr Thr Tyr Pro Asp Lys Lys Ser Ile Leu Met
            100                 105                 110
```

<210> SEQ ID NO 30
<211> LENGTH: 75
<212> TYPE: DNA
<213> ORGANISM: Homo sapiens

<400> SEQUENCE: 30

```
tagatgaaag agaagatgtt caaagaaaa cattcacaaa atgggtaaat gcacaatttt      60
ctaaggtaag aatgg                                                      75
```

<210> SEQ ID NO 31
<211> LENGTH: 80
<212> TYPE: DNA
<213> ORGANISM: Homo sapiens

<400> SEQUENCE: 31

```
aactccattt atcaattaac caaaaactcc caaataactg tgtaggttcc atgagttcag      60
gagattccac ttcaactaat                                                 80
```

<210> SEQ ID NO 32
<211> LENGTH: 80
<212> TYPE: DNA
<213> ORGANISM: Homo sapiens

```
<400> SEQUENCE: 32
aactccattt atcaattaac caaaaactcc caaataactg tggtgtatat ttatctattt    60
ttatgggttg caaaatactt                                                80

<210> SEQ ID NO 33
<211> LENGTH: 80
<212> TYPE: DNA
<213> ORGANISM: Homo sapiens

<400> SEQUENCE: 33
caaattctcc cctgaaaatt taaaaaaata cattgttctg tggtgtatat ttatctattt    60
ttatgggttg caaaatactt                                                80

<210> SEQ ID NO 34
<211> LENGTH: 55
<212> TYPE: DNA
<213> ORGANISM: Homo sapiens

<400> SEQUENCE: 34
aattaaccaa aaactcccaa ataactgtgg tgtatattta tctatttta tgggt          55
```